US010466233B2

(12) United States Patent
Barros Olmedo et al.

(10) Patent No.: US 10,466,233 B2
(45) Date of Patent: Nov. 5, 2019

(54) GENETICALLY ENCODED PROBE FOR QUANTIFICATION OF LACTATE AND METHODS FOR QUANTIFYING METABOLIC RATES AND LACTATE TRANSPORT

(75) Inventors: Luis Felipe Barros Olmedo, Valdivia (CL); Alejandro San Martin, Valdivia (CL); Sebastian Ceballo Charpentier, Valdivia (CL); Wolf B. Frommer, Washington, DC (US)

(73) Assignees: CENTRO DE ESTUDIOS CIENTIFICOS DE VALDIVIA, Valdivia (CL); CARNEGIE INSTITUTION OF WASHINGTON, Washington, DC (US)

( * ) Notice: Subject to any disclaimer, the term of this patent is extended or adjusted under 35 U.S.C. 154(b) by 519 days.

(21) Appl. No.: 14/394,018

(22) PCT Filed: Apr. 13, 2012

(86) PCT No.: PCT/US2012/033639

§ 371 (c)(1), (2), (4) Date: Oct. 10, 2014

(87) PCT Pub. No.: WO2013/154587

PCT Pub. Date: Oct. 17, 2013

(65) Prior Publication Data

US 2015/0072375 A1 Mar. 12, 2015

(51) Int. Cl.

| | |
|---|---|
| ***G01N 33/542*** | (2006.01) |
| ***G01N 33/50*** | (2006.01) |
| ***C12N 15/85*** | (2006.01) |
| ***G01N 33/58*** | (2006.01) |

(52) U.S. Cl.

CPC ......... *G01N 33/5035* (2013.01); *C12N 15/85* (2013.01); *G01N 33/5038* (2013.01); *G01N 33/542* (2013.01); *G01N 33/582* (2013.01)

(58) Field of Classification Search

None

See application file for complete search history.

(56) References Cited

U.S. PATENT DOCUMENTS

| | | | | |
|---|---|---|---|---|
| 2003/0017538 | A1 | 1/2003 | Miyawaki et al. | |
| 2003/0100707 | A1 | 5/2003 | Hwang et al. | |
| 2006/0275827 | A1 | 12/2006 | Campbell et al. | |
| 2009/0188001 | A1* | 7/2009 | Frommer et al. | 800/18 |

OTHER PUBLICATIONS

Toyoda et al., Journal of Bacteriology, 2009, vol. 191, pp. 4251-4258.*

Aguilera et al., J Bacteriol, 2008, vol. 190(8) pp. 2997-3005.*

Kennedy et al., Future Oncology, 2010, vol. 6(1) pp. 1-32.*

Deuschle et al., Cytometry Part A, 2005, vol. 64a, pp. 3-9.*

International Search Report for International Patent Application No. PCT/US2012/033639 (dated Feb. 26, 2013).

Aguilera et al. "Dual Role of LIdR in Regulation of the IIPRD Operon, Involved in I-Lactate Metabolism in *Escherichia coli." J. of Bacteriology*. (2008) 190(8):2997-3005.

UniProt_PACL7 "Putative L-lactate dehydrogenase operon regulatory." retrieved Jul. 13, 2012—http://www.uniprot.org/uniprot/POACL7.

GenBank_HQ456316 "Tretroviral Tet-shRNA expression vector TRMPV-ns, complete sequence." Dec. 11, 2010. retrieved from http://www.ncbi.nim.nih.gov/nuccore/HQ456316.

Komatsu et al. "Development of an optimized backgone of FRET biosensors for kinases and GTPases." *Molecular Biology of the Cell*. (2011) 22:4647-4656.

Looger et al. "Computational design of receptor and sensor proteins with novel functions." *Nature*, (2003) 423:185-190.

Looger et al. "Genetically Encoded FRET Sensors for Visualizing Metabolites with Subcellular Resolution in Living Cells." *Plant Phys*. (2005) 138:555-557.

Okumoto et al. "Quantitative Imaging with Fluorescent Biosensors." *Annu. Rev. Plant Biol*. (2012) 63:663-706.

Philp et al. "Lactate—a signal coordinating cell and systemic function." *J. of Exp. Biol*. (2005) 208:4561-4575.

Rajamand Ekberg et al. "Analyte Flux at a Biomaterial-Tissue Interface over Time: Implications for Sensors for Type 1 and 2 Diabets Mellitus." *J. of Diabets Sci & Tech*. (2010) 4(5):1063-1072.

Scott et al. "Comparative Metabolic Flux Profiling of Melanoma Cell Lines." *J. of Biol. Chem*. (2011) 286(49):42626-42634.

* cited by examiner

*Primary Examiner* — Mindy G Brown

(74) *Attorney, Agent, or Firm* — Merchant & Gould P.C.

(57) ABSTRACT

A nanosensor for detecting and quantifying lactate in different types of samples, such as tissues, intra-cellular and subcellular compartments, with high spatial and temporal resolution is disclosed. Methods comprising use of the nanosensor for quantifying the activity of lactate transporters, rates of cellular lactate production and cellular lactate consumption, and rate of mitochondrial pyruvate consumption are also disclosed. Methods for quantifying the transformation in energy metabolism that characterizes cancer cells with single-cell resolution and for detecting interference of candidate drugs with mitochondrial energetics are additionally disclosed.

16 Claims, 22 Drawing Sheets

Specification includes a Sequence Listing.

Figure 2:
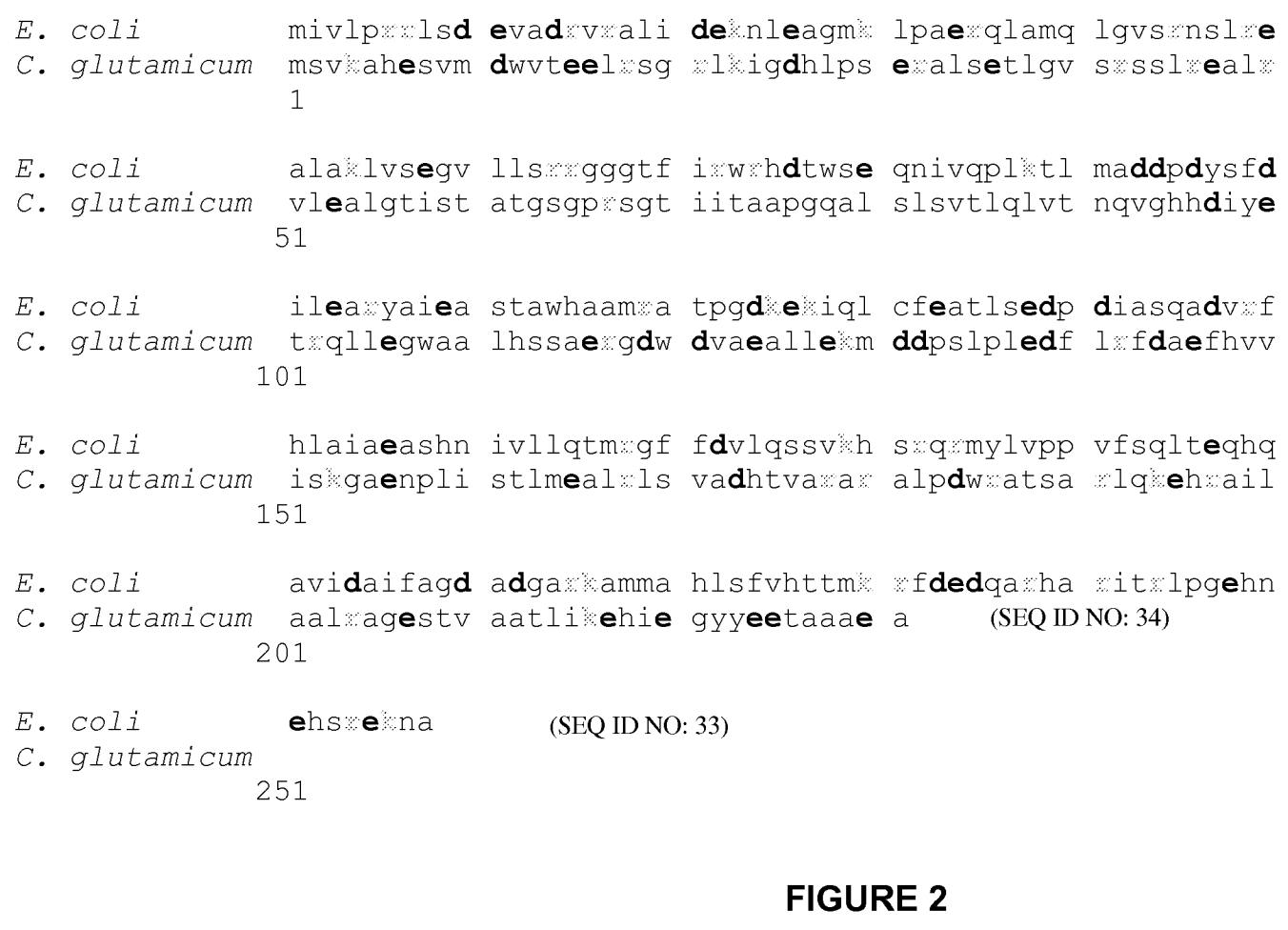

*E. coli* mivlprrlsd evadrvrali deknleagmk lpaerqlamq lgvsrnslre
*C. glutamicum* msvkahesvm dwvteelrsg rlkigdhlps eralsetlgv srsslrealr
1

*E. coli* alaklvsegv llsrrgggtf irwrhdtwse qnivqplktl maddpdysfd
*C. glutamicum* vlealgtist atgsgprsgt iitaapgqal slsvtlqlvt nqvghhdiye
51

*E. coli* ilearyaiea stawhaamra tpgdkekiql cfeatlsedp diasqadvrf
*C. glutamicum* trqllegwaa lhssaergdw dvaeallekm ddpslpledf lrfdaefhvv
101

*E. coli* hlaiaeashn ivllqtmrgf fdvlqssvkh srqrmylvpp vfsqlteqhq
*C. glutamicum* iskgaenpli stlmealrls vadhtvarar alpdwratsa rlqkehrail
151

*E. coli* avidaifagd adgarkamma hlsfvhttmk rfdedqarha ritrlpgehn
*C. glutamicum* aalragestv aatlikehie gyyeetaaae a (SEQ ID NO: 34)
201

*E. coli* ehsrekna (SEQ ID NO: 33)
*C. glutamicum*
251

```
Alignment of Lactate nanosensor variants
Section 1
           (1) 1         10        20        30        40             57
Variant 01 (1) MVSKGEETTMGVIKPDMKIKLKMEGNVNGHAFVIEGEGEGKPYDGTNTINLEVKEGA
Variant 02 (1) MVSKGEETTMGVIKPDMKIKLKMEGNVNGHAFVIEGEGEGKPYDGTNTINLEVKEGA
Variant 03 (1) MVSKGEETTMGVIKPDMKIKLKMEGNVNGHAFVIEGEGEGKPYDGTNTINLEVKEGA
Variant 04 (1) MVSKGEETTMGVIKPDMKIKLKMEGNVNGHAFVIEGEGEGKPYDGTNTINLEVKEGA
Variant 05 (1) MVSKGEETTMGVIKPDMKIKLKMEGNVNGHAFVIEGEGEGKPYDGTNTINLEVKEGA
Variant 06 (1) MVSKGEETTMGVIKPDMKIKLKMEGNVNGHAFVIEGEGEGKPYDGTNTINLEVKEGA
Variant 07 (1) MVSKGEETTMGVIKPDMKIKLKMEGNVNGHAFVIEGEGEGKPYDGTNTINLEVKEGA
Variant 08 (1) MVSKGEETTMGVIKPDMKIKLKMEGNVNGHAFVIEGEGEGKPYDGTNTINLEVKEGA
Variant 09 (1) MVSKGEETTMGVIKPDMKIKLKMEGNVNGHAFVIEGEGEGKPYDGTNTINLEVKEGA
Variant 10 (1) MVSKGEETTMGVIKPDMKIKLKMEGNVNGHAFVIEGEGEGKPYDGTNTINLEVKEGA
Variant 11 (1) MVSKGEETTMGVIKPDMKIKLKMEGNVNGHAFVIEGEGEGKPYDGTNTINLEVKEGA
Variant 12 (1) MVSKGEETTMGVIKPDMKIKLKMEGNVNGHAFVIEGEGEGKPYDGTNTINLEVKEGA
Variant 13 (1) MVSKGEETTMGVIKPDMKIKLKMEGNVNGHAFVIEGEGEGKPYDGTNTINLEVKEGA
Variant 14 (1) MVSKGEETTMGVIKPDMKIKLKMEGNVNGHAFVIEGEGEGKPYDGTNTINLEVKEGA
Variant 15 (1) MVSKGEETTMGVIKPDMKIKLKMEGNVNGHAFVIEGEGEGKPYDGTNTINLEVKEGA
Variant 16 (1) MVSKGEETTMGVIKPDMKIKLKMEGNVNGHAFVIEGEGEGKPYDGTNTINLEVKEGA

Section 2
           (58) 58           70        80        90        100           114
Variant 01 (58) PLPFSYDILTTAFAYGNRAFTKYPDDIPNYFKQSFPEGYSWERTMTFEDKGIVKVKS
Variant 02 (58) PLPFSYDILTTAFAYGNRAFTKYPDDIPNYFKQSFPEGYSWERTMTFEDKGIVKVKS
Variant 03 (58) PLPFSYDILTTAFAYGNRAFTKYPDDIPNYFKQSFPEGYSWERTMTFEDKGIVKVKS
Variant 04 (58) PLPFSYDILTTAFAYGNRAFTKYPDDIPNYFKQSFPEGYSWERTMTFEDKGIVKVKS
Variant 05 (58) PLPFSYDILTTAFAYGNRAFTKYPDDIPNYFKQSFPEGYSWERTMTFEDKGIVKVKS
Variant 06 (58) PLPFSYDILTTAFAYGNRAFTKYPDDIPNYFKQSFPEGYSWERTMTFEDKGIVKVKS
Variant 07 (58) PLPFSYDILTTAFAYGNRAFTKYPDDIPNYFKQSFPEGYSWERTMTFEDKGIVKVKS
Variant 08 (58) PLPFSYDILTTAFAYGNRAFTKYPDDIPNYFKQSFPEGYSWERTMTFEDKGIVKVKS
Variant 09 (58) PLPFSYDILTTAFAYGNRAFTKYPDDIPNYFKQSFPEGYSWERTMTFEDKGIVKVKS
Variant 10 (58) PLPFSYDILTTAFAYGNRAFTKYPDDIPNYFKQSFPEGYSWERTMTFEDKGIVKVKS
Variant 11 (58) PLPFSYDILTTAFAYGNRAFTKYPDDIPNYFKQSFPEGYSWERTMTFEDKGIVKVKS
Variant 12 (58) PLPFSYDILTTAFAYGNRAFTKYPDDIPNYFKQSFPEGYSWERTMTFEDKGIVKVKS
Variant 13 (58) PLPFSYDILTTAFAYGNRAFTKYPDDIPNYFKQSFPEGYSWERTMTFEDKGIVKVKS
Variant 14 (58) PLPFSYDILTTAFAYGNRAFTKYPDDIPNYFKQSFPEGYSWERTMTFEDKGIVKVKS
Variant 15 (58) PLPFSYDILTTAFAYGNRAFTKYPDDIPNYFKQSFPEGYSWERTMTFEDKGIVKVKS
Variant 16 (58) PLPFSYDILTTAFAYGNRAFTKYPDDIPNYFKQSFPEGYSWERTMTFEDKGIVKVKS

Section 3
           (115) 115  120        130       140       150       160        171
Variant 01 (115) DISMEEDSFIYEIHLKGENFPPNGPVMQKKTTGWDASTERMYVRDGVLKGDVKHKLL
Variant 02 (115) DISMEEDSFIYEIHLKGENFPPNGPVMQKKTTGWDASTERMYVRDGVLKGDVKHKLL
Variant 03 (115) DISMEEDSFIYEIHLKGENFPPNGPVMQKKTTGWDASTERMYVRDGVLKGDVKHKLL
Variant 04 (115) DISMEEDSFIYEIHLKGENFPPNGPVMQKKTTGWDASTERMYVRDGVLKGDVKHKLL
Variant 05 (115) DISMEEDSFIYEIHLKGENFPPNGPVMQKKTTGWDASTERMYVRDGVLKGDVKHKLL
Variant 06 (115) DISMEEDSFIYEIHLKGENFPPNGPVMQKKTTGWDASTERMYVRDGVLKGDVKHKLL
Variant 07 (115) DISMEEDSFIYEIHLKGENFPPNGPVMQKKTTGWDASTERMYVRDGVLKGDVKHKLL
Variant 08 (115) DISMEEDSFIYEIHLKGENFPPNGPVMQKKTTGWDASTERMYVRDGVLKGDVKHKLL
Variant 09 (115) DISMEEDSFIYEIHLKGENFPPNGPVMQKKTTGWDASTERMYVRDGVLKGDVKHKLL
Variant 10 (115) DISMEEDSFIYEIHLKGENFPPNGPVMQKKTTGWDASTERMYVRDGVLKGDVKHKLL
Variant 11 (115) DISMEEDSFIYEIHLKGENFPPNGPVMQKKTTGWDASTERMYVRDGVLKGDVKHKLL
Variant 12 (115) DISMEEDSFIYEIHLKGENFPPNGPVMQKKTTGWDASTERMYVRDGVLKGDVKHKLL
Variant 13 (115) DISMEEDSFIYEIHLKGENFPPNGPVMQKKTTGWDASTERMYVRDGVLKGDVKHKLL
Variant 14 (115) DISMEEDSFIYEIHLKGENFPPNGPVMQKKTTGWDASTERMYVRDGVLKGDVKHKLL
Variant 15 (115) DISMEEDSFIYEIHLKGENFPPNGPVMQKKTTGWDASTERMYVRDGVLKGDVKHKLL
Variant 16 (115) DISMEEDSFIYEIHLKGENFPPNGPVMQKKTTGWDASTERMYVRDGVLKGDVKHKLL
```

FIGURE 3 (Cont.)

Alignment of Lactate nanosensor variants

```
Section 4
           (172) 172     180       190       200       210           228
Variant 01 (172) LEGGGHHRVDFKTIYRAKKAVKLPDYHFVDHRIEILNHDKDYNKVTVYESAVARNST
Variant 02 (172) LEGGGHHRVDFKTIYRAKKAVKLPDYHFVDHRIEILNHDKDYNKVTVYESAVARNST
Variant 03 (172) LEGGGHHRVDFKTIYRAKKAVKLPDYHFVDHRIEILNHDKDYNKVTVYESAVARNST
Variant 04 (172) LEGGGHHRVDFKTIYRAKKAVKLPDYHFVDHRIEILNHDKDYNKVTVYESAVARNST
Variant 05 (172) LEGGGHHRVDFKTIYRAKKAVKLPDYHFVDHRIEILNHDKDYNKVTVYESAVARNST
Variant 06 (172) LEGGGHHRVDFKTIYRAKKAVKLPDYHFVDHRIEILNHDKDYNKVTVYESAVARNST
Variant 07 (172) LEGGGHHRVDFKTIYRAKKAVKLPDYHFVDHRIEILNHDKDYNKVTVYESAVARNST
Variant 08 (172) LEGGGHHRVDFKTIYRAKKAVKLPDYHFVDHRIEILNHDKDYNKVTVYESAVARNST
Variant 09 (172) LEGGGHHRVDFKTIYRAKKAVKLPDYHFVDHRIEILNHDKDYNKVTVYESAVARNST
Variant 10 (172) LEGGGHHRVDFKTIYRAKKAVKLPDYHFVDHRIEILNHDKDYNKVTVYESAVARNST
Variant 11 (172) LEGGGHHRVDFKTIYRAKKAVKLPDYHFVDHRIEILNHDKDYNKVTVYESAVARNST
Variant 12 (172) LEGGGHHRVDFKTIYRAKKAVKLPDYHFVDHRIEILNHDKDYNKVTVYESAVARNST
Variant 13 (172) LEGGGHHRVDFKTIYRAKKAVKLPDYHFVDHRIEILNHDKDYNKVTVYESAVARNST
Variant 14 (172) LEGGGHHRVDFKTIYRAKKAVKLPDYHFVDHRIEILNHDKDYNKVTVYESAVARNST
Variant 15 (172) LEGGGHHRVDFKTIYRAKKAVKLPDYHFVDHRIEILNHDKDYNKVTVYESAVARNST
Variant 16 (172) LEGGGHHRVDFKTIYRAKKAVKLPDYHFVDHRIEILNHDKDYNKVTVYESAVARNST

Section 5
           (229) 229        240       250       260      270           285
Variant 01 (229) DGMDELYKRSGTTSLYKKAGSEFALGTMIVLPRRLSDEVADRVRALIDEKNLEAGMK
Variant 02 (229) DGMDELYKRSGTTSLYKKAGSEFAL---GTMSVKAHESVMDWVTEELRSGRLKIGDH
Variant 03 (229) DGMDELYKRSGTM---------------IVLPRRLSDEVADRVRALIDEKNLEAGMK
Variant 04 (229) DGMDELYKRS------------------GTMSVKAHESVMDWVTEELRSGRLKIGDH
Variant 05 (229) DGMDELYKRSGTTSLYKKAGSEFALGTMIVLPRRLSDEVADRVRALIDEKNLEAGMK
Variant 06 (229) DGMDELYKRSGTTSLYKKAGSEFAL---GTMSVKAHESVMDWVTEELRSGRLKIGDH
Variant 07 (229) DGMDELYKRSGTM---------------IVLPRRLSDEVADRVRALIDEKNLEAGMK
Variant 08 (229) DGMDELYKRS------------------GTMSVKAHESVMDWVTEELRSGRLKIGDH
Variant 09 (229) DGMDELYKRSGTT---------------SLYKKAGSEFAL-----------------
Variant 10 (229) DGMDELYKRS------------------G----------------------------
Variant 11 (229) DGMDELYKRS-----------------------------------------------
Variant 12 (229) DGMDELYKRS-----------------------------------------------
Variant 13 (229) DGMDELYKRSGTTSLYKKAGSEFALG-------------------------------
Variant 14 (229) DGMDELYKRS------------------G----------------------------
Variant 15 (229) DGMDELYKRS-----------------------------------------------
Variant 16 (229) DGMDELYKRS-----------------------------------------------

Section 6
           (286) 286           300       310       320       330         342
Variant 01 (286) LPAERQLAMQLGVSRNSLREALAKLVSEGVLLSRRGGGTFIRWRHDTWSEQNIVQPL
Variant 02 (283) LPSERALSETLGVSRSSLREALRVLEALGTISTATGSGPRSGTIITAAPGQALSLSV
Variant 03 (271) LPAERQLAMQLGVSRNSLREALAKLVSEGVLLSRRGGGTFIRWRHDTWSEQNIVQPL
Variant 04 (268) LPSERALSETLGVSRSSLREALRVLEALGTISTATGSGPRSGTIITAAPGQALSLSV
Variant 05 (286) LPAERQLAMQLGVSRNSLREALAKLVSEGVLLSRRGGGTFIRWRHDTWSEQNIVQPL
Variant 06 (283) LPSERALSETLGVSRSSLREALRVLEALGTISTATGSGPRSGTIITAAPGQALSLSV
Variant 07 (271) LPAERQLAMQLGVSRNSLREALAKLVSEGVLLSRRGGGTFIRWRHDTWSEQNIVQPL
Variant 08 (268) LPSERALSETLGVSRSSLREALRVLEALGTISTATGSGPRSGTIITAAPGQALSLSV
Variant 09 (254) -----------------------------------------------GTEQNIVQPL
Variant 10 (240) ---------------------------------TTSLYKKAGSEFALGTGQALSLSV
Variant 11 (239) -----------------------------------------------GTEQNIVQPL
Variant 12 (239) -----------------------------------------------GTGQALSLSV
Variant 13 (255) ------------------------------------------------TEQNIVQPL
Variant 14 (240) ---------------------------------TTSLYKKAGSEFALGTGQALSLSV
Variant 15 (239) -----------G------------------------------------TEQNIVQPL
Variant 16 (239) -----------------------------------------------GTGQALSLSV
```

FIGURE 3 (Cont.)

```
Alignment of Lactate nanosensor variants
Section 7
           (343) 343    350       360       370       380                 399
Variant 01 (343) KTLMADDPDYSFDILEARYAIEASTAWHAAMRATPGDKEKIQLCFEATLSEDPDIAS
Variant 02 (340) TLQLVTNQVGHHDIYETRQLLEGWAALHSSAERGDWDVAEALLEKMDDPSLPLEDFL
Variant 03 (328) KTLMADDPDYSFDILEARYAIEASTAWHAAMRATPGDKEKIQLCFEATLSEDPDIAS
Variant 04 (325) TLQLVTNQVGHHDIYETRQLLEGWAALHSSAERGDWDVAEALLEKMDDPSLPLEDFL
Variant 05 (343) KTLMADDPDYSFDILEARYAIEASTAWHAAMRATPGDKEKIQLCFEATLSEDPDIAS
Variant 06 (340) TLQLVTNQVGHHDIYETRQLLEGWAALHSSAERGDWDVAEALLEKMDDPSLPLEDFL
Variant 07 (328) KTLMADDPDYSFDILEARYAIEASTAWHAAMRATPGDKEKIQLCFEATLSEDPDIAS
Variant 08 (325) TLQLVTNQVGHHDIYETRQLLEGWAALHSSAERGDWDVAEALLEKMDDPSLPLEDFL
Variant 09 (264) KTLMADDPDYSFDILEARYAIEASTAWHAAMRATPGDKEKIQLCFEATLSEDPDIAS
Variant 10 (264) TLQLVTNQVGHHDIYETRQLLEGWAALHSSAERGDWDVAEALLEKMDDPSLPLEDFL
Variant 11 (249) KTLMADDPDYSFDILEARYAIEASTAWHAAMRATPGDKEKIQLCFEATLSEDPDIAS
Variant 12 (249) TLQLVTNQVGHHDIYETRQLLEGWAALHSSAERGDWDVAEALLEKMDDPSLPLEDFL
Variant 13 (264) KTLMADDPDYSFDILEARYAIEASTAWHAAMRATPGDKEKIQLCFEATLSEDPDIAS
Variant 14 (264) TLQLVTNQVGHHDIYETRQLLEGWAALHSSAERGDWDVAEALLEKMDDPSLPLEDFL
Variant 15 (249) KTLMADDPDYSFDILEARYAIEASTAWHAAMRATPGDKEKIQLCFEATLSEDPDIAS
Variant 16 (249) TLQLVTNQVGHHDIYETRQLLEGWAALHSSAERGDWDVAEALLEKMDDPSLPLEDFL

Section 8
           (400) 400       410       420       430       440              456
Variant 01 (400) QADVRFHLAIAEASHNIVLLQTMRGFFDVLQSSVKHSRQRMYLVPPVFSQLTEQHQA
Variant 02 (397) RFDAEFHVVISKGAENPLISTLMEALRLSVADHTVARARALPDWRATSARLQKEHRA
Variant 03 (385) QADVRFHLAIAEASHNIVLLQTMRGFFDVLQSSVKHSRQRMYLVPPVFSQLTEQHQA
Variant 04 (382) RFDAEFHVVISKGAENPLISTLMEALRLSVADHTVARARALPDWRATSARLQKEHRA
Variant 05 (400) QADVRFHLAIAEASHNIVLLQTMRGFFDVLQSSVKHSRQRMYLVPPVFSQLTEQHQA
Variant 06 (397) RFDAEFHVVISKGAENPLISTLMEALRLSVADHTVARARALPDWRATSARLQKEHRA
Variant 07 (385) QADVRFHLAIAEASHNIVLLQTMRGFFDVLQSSVKHSRQRMYLVPPVFSQLTEQHQA
Variant 08 (382) RFDAEFHVVISKGAENPLISTLMEALRLSVADHTVARARALPDWRATSARLQKEHRA
Variant 09 (321) QADVRFHLAIAEASHNIVLLQTMRGFFDVLQSSVKHSRQRMYLVPPVFSQLTEQHQA
Variant 10 (321) RFDAEFHVVISKGAENPLISTLMEALRLSVADHTVARARALPDWRATSARLQKEHRA
Variant 11 (306) QADVRFHLAIAEASHNIVLLQTMRGFFDVLQSSVKHSRQRMYLVPPVFSQLTEQHQA
Variant 12 (306) RFDAEFHVVISKGAENPLISTLMEALRLSVADHTVARARALPDWRATSARLQKEHRA
Variant 13 (321) QADVRFHLAIAEASHNIVLLQTMRGFFDVLQSSVKHSRQRMYLVPPVFSQLTEQHQA
Variant 14 (321) RFDAEFHVVISKGAENPLISTLMEALRLSVADHTVARARALPDWRATSARLQKEHRA
Variant 15 (306) QADVRFHLAIAEASHNIVLLQTMRGFFDVLQSSVKHSRQRMYLVPPVFSQLTEQHQA
Variant 16 (306) RFDAEFHVVISKGAENPLISTLMEALRLSVADHTVARARALPDWRATSARLQKEHRA

Section 9
           (457) 457          470       480       490       500          513
Variant 01 (457) VIDAIFAGDADGARKAMMAHLSFVHTTMKRFDEDQARHARITRLPGEHNEHSREKNA
Variant 02 (454) ILAALRAGESTVAATLIKEHIEGYY--EETAAAEALKKG-------EFDPAFLYKVV
Variant 03 (442) VIDAIFAGDADGARKAMMAHLSFVHTTMKRFDEDQARHARITRLPGEHNEHSREKNA
Variant 04 (439) ILAALRAGESTVAATLIKEHIEGYY--EETAAAEALKKG-------EFDPAFLYKVV
Variant 05 (457) VIDAIFAGDADGARKAMMAHLSFVHTTMKRFDEDQARHARITRLPGEHNEHSREKNA
Variant 06 (454) ILAALRAGESTVAATLIKEHIEGYY--EETAAAEALKR-------------------
Variant 07 (442) VIDAIFAGDADGARKAMMAHLSFVHTTMKRFDEDQARHARITRLPGEHNEHSREKNA
Variant 08 (439) ILAALRAGESTVAATLIKEHIEGYY--EETAAAEALKR-------------------
Variant 09 (378) VIDAIFAGDADGARKAMMAHLSFVHTTMKRFDEDQARHARITRLPGEHNEHSREKNA
Variant 10 (378) ILAALRAGESTVAATLIKEHIEGYY--EETAAAEALKKG-------EFDPAFLYKVV
Variant 11 (363) VIDAIFAGDADGARKAMMAHLSFVHTTMKRFDEDQARHARITRLPGEHNEHSREKNA
Variant 12 (363) ILAALRAGESTVAATLIKEHIEGYY--EETAAAEALKKG-------EFDPAFLYKVV
Variant 13 (378) VIDAIFAGDADGARKAMMAHLSFVHTTMKRFDEDQARHARITRLPGEHNEHSREKNA
Variant 14 (378) ILAALRAGESTVAATLIKEHIEGYY--EETAAAEALKR-------------------
Variant 15 (363) VIDAIFAGDADGARKAMMAHLSFVHTTMKRFDEDQARHARITRLPGEHNEHSREKNA
Variant 16 (363) ILAALRAGESTVAATLIKEHIEGYY--EETAAAEALKR-------------------
```

FIGURE 3 (Cont.)

Alignment of Lactate nanosensor variants

Section 10

```
           (514) 514   520        530        540        550        560       570
Variant 01 (514) LKKGEFDPAFLYKVVLKRSTMVSKGEELFTGVVPILVELDGDVNGHKFSVSGEGEGD
Variant 02 (502) LKR---------------STMVSKGEELFTGVVPILVELDGDVNGHKFSVSGEGEGD
Variant 03 (499) LKKGEFDPAFLYKVVLKRSTMVSKGEELFTGVVPILVELDGDVNGHKFSVSGEGEGD
Variant 04 (487) LKR---------------STMVSKGEELFTGVVPILVELDGDVNGHKFSVSGEGEGD
Variant 05 (514) LKR---------------STMVSKGEELFTGVVPILVELDGDVNGHKFSVSGEGEGD
Variant 06 (490) ------------------STMVSKGEELFTGVVPILVELDGDVNGHKFSVSGEGEGD
Variant 07 (499) LKR---------------STMVSKGEELFTGVVPILVELDGDVNGHKFSVSGEGEGD
Variant 08 (475) ------------------STMVSKGEELFTGVVPILVELDGDVNGHKFSVSGEGEGD
Variant 09 (435) LKKGEFDPAFLYKVVLKRSTMVSKGEELFTGVVPILVELDGDVNGHKFSVSGEGEGD
Variant 10 (426) LKR---------------STMVSKGEELFTGVVPILVELDGDVNGHKFSVSGEGEGD
Variant 11 (420) LKKGEFDPAFLYKVVLKRSTMVSKGEELFTGVVPILVELDGDVNGHKFSVSGEGEGD
Variant 12 (411) LKR---------------STMVSKGEELFTGVVPILVELDGDVNGHKFSVSGEGEGD
Variant 13 (435) LKR---------------STMVSKGEELFTGVVPILVELDGDVNGHKFSVSGEGEGD
Variant 14 (414) ------------------STMVSKGEELFTGVVPILVELDGDVNGHKFSVSGEGEGD
Variant 15 (420) LKR---------------STMVSKGEELFTGVVPILVELDGDVNGHKFSVSGEGEGD
Variant 16 (399) ------------------STMVSKGEELFTGVVPILVELDGDVNGHKFSVSGEGEGD
```

Section 11

```
           (571) 571       580        590        600        610              627
Variant 01 (571) ATYGKLTLKLICTTGKLPVPWPTLVTTLGYGLQCFARYPDHMKQHDFFKSAMPEGYV
Variant 02 (544) ATYGKLTLKLICTTGKLPVPWPTLVTTLGYGLQCFARYPDHMKQHDFFKSAMPEGYV
Variant 03 (556) ATYGKLTLKLICTTGKLPVPWPTLVTTLGYGLQCFARYPDHMKQHDFFKSAMPEGYV
Variant 04 (529) ATYGKLTLKLICTTGKLPVPWPTLVTTLGYGLQCFARYPDHMKQHDFFKSAMPEGYV
Variant 05 (556) ATYGKLTLKLICTTGKLPVPWPTLVTTLGYGLQCFARYPDHMKQHDFFKSAMPEGYV
Variant 06 (529) ATYGKLTLKLICTTGKLPVPWPTLVTTLGYGLQCFARYPDHMKQHDFFKSAMPEGYV
Variant 07 (541) ATYGKLTLKLICTTGKLPVPWPTLVTTLGYGLQCFARYPDHMKQHDFFKSAMPEGYV
Variant 08 (514) ATYGKLTLKLICTTGKLPVPWPTLVTTLGYGLQCFARYPDHMKQHDFFKSAMPEGYV
Variant 09 (492) ATYGKLTLKLICTTGKLPVPWPTLVTTLGYGLQCFARYPDHMKQHDFFKSAMPEGYV
Variant 10 (468) ATYGKLTLKLICTTGKLPVPWPTLVTTLGYGLQCFARYPDHMKQHDFFKSAMPEGYV
Variant 11 (477) ATYGKLTLKLICTTGKLPVPWPTLVTTLGYGLQCFARYPDHMKQHDFFKSAMPEGYV
Variant 12 (453) ATYGKLTLKLICTTGKLPVPWPTLVTTLGYGLQCFARYPDHMKQHDFFKSAMPEGYV
Variant 13 (477) ATYGKLTLKLICTTGKLPVPWPTLVTTLGYGLQCFARYPDHMKQHDFFKSAMPEGYV
Variant 14 (453) ATYGKLTLKLICTTGKLPVPWPTLVTTLGYGLQCFARYPDHMKQHDFFKSAMPEGYV
Variant 15 (462) ATYGKLTLKLICTTGKLPVPWPTLVTTLGYGLQCFARYPDHMKQHDFFKSAMPEGYV
Variant 16 (438) ATYGKLTLKLICTTGKLPVPWPTLVTTLGYGLQCFARYPDHMKQHDFFKSAMPEGYV
```

Section 12

```
           (628) 628         640        650        660        670           684
Variant 01 (628) QERTIFFKDDGNYKTRAEVKFEGDTLVNRIELKGIDFKEDGNILGHKLEYNYNSHNV
Variant 02 (601) QERTIFFKDDGNYKTRAEVKFEGDTLVNRIELKGIDFKEDGNILGHKLEYNYNSHNV
Variant 03 (613) QERTIFFKDDGNYKTRAEVKFEGDTLVNRIELKGIDFKEDGNILGHKLEYNYNSHNV
Variant 04 (586) QERTIFFKDDGNYKTRAEVKFEGDTLVNRIELKGIDFKEDGNILGHKLEYNYNSHNV
Variant 05 (613) QERTIFFKDDGNYKTRAEVKFEGDTLVNRIELKGIDFKEDGNILGHKLEYNYNSHNV
Variant 06 (586) QERTIFFKDDGNYKTRAEVKFEGDTLVNRIELKGIDFKEDGNILGHKLEYNYNSHNV
Variant 07 (598) QERTIFFKDDGNYKTRAEVKFEGDTLVNRIELKGIDFKEDGNILGHKLEYNYNSHNV
Variant 08 (571) QERTIFFKDDGNYKTRAEVKFEGDTLVNRIELKGIDFKEDGNILGHKLEYNYNSHNV
Variant 09 (549) QERTIFFKDDGNYKTRAEVKFEGDTLVNRIELKGIDFKEDGNILGHKLEYNYNSHNV
Variant 10 (525) QERTIFFKDDGNYKTRAEVKFEGDTLVNRIELKGIDFKEDGNILGHKLEYNYNSHNV
Variant 11 (534) QERTIFFKDDGNYKTRAEVKFEGDTLVNRIELKGIDFKEDGNILGHKLEYNYNSHNV
Variant 12 (510) QERTIFFKDDGNYKTRAEVKFEGDTLVNRIELKGIDFKEDGNILGHKLEYNYNSHNV
Variant 13 (534) QERTIFFKDDGNYKTRAEVKFEGDTLVNRIELKGIDFKEDGNILGHKLEYNYNSHNV
Variant 14 (510) QERTIFFKDDGNYKTRAEVKFEGDTLVNRIELKGIDFKEDGNILGHKLEYNYNSHNV
Variant 15 (519) QERTIFFKDDGNYKTRAEVKFEGDTLVNRIELKGIDFKEDGNILGHKLEYNYNSHNV
Variant 16 (495) QERTIFFKDDGNYKTRAEVKFEGDTLVNRIELKGIDFKEDGNILGHKLEYNYNSHNV
```

FIGURE 3 (Cont.)

```
Alignment of Lactate nanosensor variants
Section 13
             (685) 685  690       700       710       720       730      741
Variant 01  (685) YITADKQKNGIKANFKIRHNIEDGGVQLADHYQQNTPIGDGPVLLPDNHYLSYQSAL
Variant 02  (658) YITADKQKNGIKANFKIRHNIEDGGVQLADHYQQNTPIGDGPVLLPDNHYLSYQSAL
Variant 03  (670) YITADKQKNGIKANFKIRHNIEDGGVQLADHYQQNTPIGDGPVLLPDNHYLSYQSAL
Variant 04  (643) YITADKQKNGIKANFKIRHNIEDGGVQLADHYQQNTPIGDGPVLLPDNHYLSYQSAL
Variant 05  (670) YITADKQKNGIKANFKIRHNIEDGGVQLADHYQQNTPIGDGPVLLPDNHYLSYQSAL
Variant 06  (643) YITADKQKNGIKANFKIRHNIEDGGVQLADHYQQNTPIGDGPVLLPDNHYLSYQSAL
Variant 07  (655) YITADKQKNGIKANFKIRHNIEDGGVQLADHYQQNTPIGDGPVLLPDNHYLSYQSAL
Variant 08  (628) YITADKQKNGIKANFKIRHNIEDGGVQLADHYQQNTPIGDGPVLLPDNHYLSYQSAL
Variant 09  (606) YITADKQKNGIKANFKIRHNIEDGGVQLADHYQQNTPIGDGPVLLPDNHYLSYQSAL
Variant 10  (582) YITADKQKNGIKANFKIRHNIEDGGVQLADHYQQNTPIGDGPVLLPDNHYLSYQSAL
Variant 11  (591) YITADKQKNGIKANFKIRHNIEDGGVQLADHYQQNTPIGDGPVLLPDNHYLSYQSAL
Variant 12  (567) YITADKQKNGIKANFKIRHNIEDGGVQLADHYQQNTPIGDGPVLLPDNHYLSYQSAL
Variant 13  (591) YITADKQKNGIKANFKIRHNIEDGGVQLADHYQQNTPIGDGPVLLPDNHYLSYQSAL
Variant 14  (567) YITADKQKNGIKANFKIRHNIEDGGVQLADHYQQNTPIGDGPVLLPDNHYLSYQSAL
Variant 15  (576) YITADKQKNGIKANFKIRHNIEDGGVQLADHYQQNTPIGDGPVLLPDNHYLSYQSAL
Variant 16  (552) YITADKQKNGIKANFKIRHNIEDGGVQLADHYQQNTPIGDGPVLLPDNHYLSYQSAL

Section 14
             (742) 742     750       760       772
Variant 01  (742) SKDPNEKRDHMVLLEFVTAAGITLGMDELYK (SEQ ID NO: 1)
Variant 02  (715) SKDPNEKRDHMVLLEFVTAAGITLGMDELYK (SEQ ID NO: 2)
Variant 03  (727) SKDPNEKRDHMVLLEFVTAAGITLGMDELYK (SEQ ID NO: 3)
Variant 04  (700) SKDPNEKRDHMVLLEFVTAAGITLGMDELYK (SEQ ID NO: 4)
Variant 05  (727) SKDPNEKRDHMVLLEFVTAAGITLGMDELYK (SEQ ID NO: 5)
Variant 06  (700) SKDPNEKRDHMVLLEFVTAAGITLGMDELYK (SEQ ID NO: 6)
Variant 07  (712) SKDPNEKRDHMVLLEFVTAAGITLGMDELYK (SEQ ID NO: 7)
Variant 08  (685) SKDPNEKRDHMVLLEFVTAAGITLGMDELYK (SEQ ID NO: 8)
Variant 09  (663) SKDPNEKRDHMVLLEFVTAAGITLGMDELYK (SEQ ID NO: 9)
Variant 10  (639) SKDPNEKRDHMVLLEFVTAAGITLGMDELYK (SEQ ID NO: 10)
Variant 11  (648) SKDPNEKRDHMVLLEFVTAAGITLGMDELYK (SEQ ID NO: 11)
Variant 12  (624) SKDPNEKRDHMVLLEFVTAAGITLGMDELYK (SEQ ID NO: 12)
Variant 13  (648) SKDPNEKRDHMVLLEFVTAAGITLGMDELYK (SEQ ID NO: 13)
Variant 14  (624) SKDPNEKRDHMVLLEFVTAAGITLGMDELYK (SEQ ID NO: 14)
Variant 15  (633) SKDPNEKRDHMVLLEFVTAAGITLGMDELYK (SEQ ID NO: 15)
Variant 16  (609) SKDPNEKRDHMVLLEFVTAAGITLGMDELYK (SEQ ID NO: 16)
```

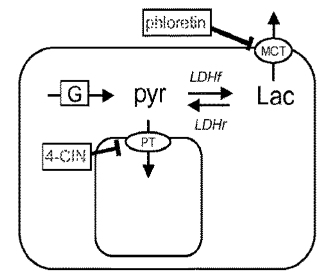

Pyruvate concentration, [Pyr] (μM)
Lactate, [Lac] (μM)
Glycolytic pyruvate production, G (μM/s)
Lactate dexydrogenase forward reaction, *LDHf* ($s^{-1}$)
Lactate dehydrogenase reverse reaction, *LDHr* ($s^{-1}$)
Cellular lactate release, MCT (μM/s)
Mitochondrial pyruvate uptake, PT (μM/s)

Equations $$d[Pyr]/dt = (G + [Lac]*LDHr - [Pyr]*LDHf - PT)/vol$$

$$d[Lac]/dt = ([Pyr]*LDHf - [Lac]*LDHr - MCT)/vol$$

$$MCT = V_{MCT}*[Lac]/(K_{MCT} + [Lac])$$

$$K_{MCT} = 5000;\ Vol = 1 liter$$

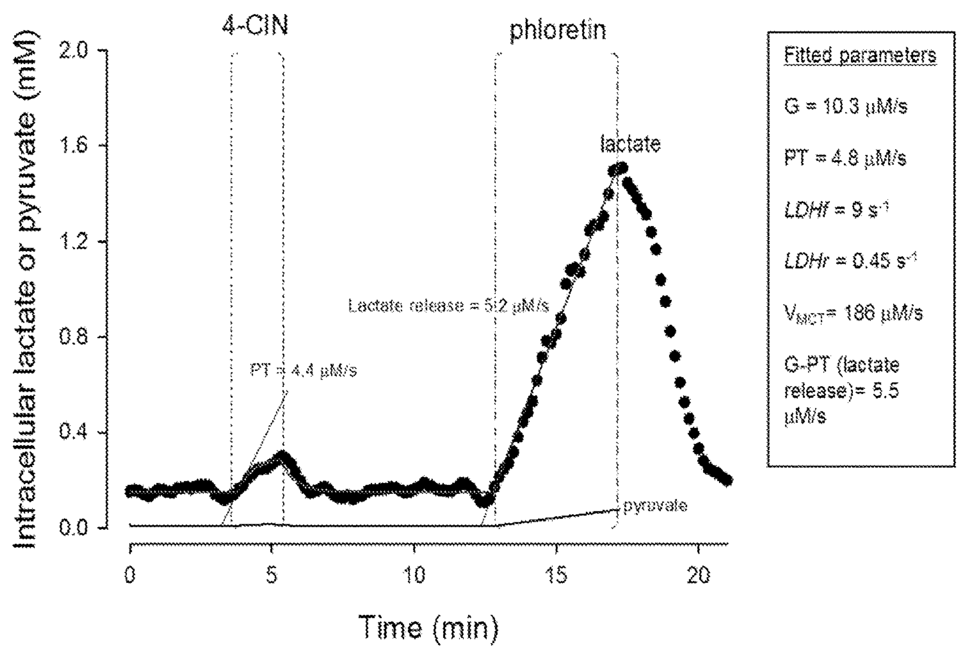

Figure 16

GENETICALLY ENCODED PROBE FOR QUANTIFICATION OF LACTATE AND METHODS FOR QUANTIFYING METABOLIC RATES AND LACTATE TRANSPORT

This application is a U.S. National Stage Application under 35 U.S.C. § 371 of International Patent Application No. PCT/US2012/033639 filed 13 Apr. 2012 the disclosure of which is hereby incorporated by reference in its entirety. The International Application was published in English on 17 Oct. 2013 as WO 2013/154587.

The PCT application was filed in the name of Centro de Estudios Cientificos de Valdivia a Chilean corporation and Carnegie Institution of Washington, a U.S. national corporation, applicant for the designation of all countries except the US, and Luis Felipe Barros Olmedo, Alejandro San Martin, Sebastian Ceballo Charpentier, all citizens of Chile, and Wolf B. Frommer, a citizen of Germany, applicants for the designation of the US only.

FIELD OF THE INVENTION

The present invention comprises a nanosensor for detecting and quantifying lactate in different types of samples, such as tissues, intra-cellular and even in subcellular compartments, with high spatial and temporal resolution, across four orders of concentration magnitude, and methods that make use of this nanosensor for the quantification of the activity of lactate transporters, for the quantification of the rates of cellular lactate production and cellular lactate consumption, and for the quantification of the rate of mitochondrial pyruvate consumption. Additionally, the invention comprises a method to quantify the transformation in energy metabolism that characterizes cancer cells with single-cell resolution and a method to detect interference of candidate drugs with mitochondrial energetics.

BACKGROUND OF THE INVENTION

Lactate is an organic chemical compound that participates in the metabolism of eukaryotic and prokaryotic cells. Lactate is exchanged between organelles, cells and organs as fuel or waste product, and also plays important signaling and biosynthetic roles, being involved in the physiology of exercise, inflammation, wound healing, neurovascular coupling and also in diseases such as cancer, hypoxic/ischemic disease and microbial infection. In addition, lactate is of industrial interest as a food additive, as a detergent, for the detection and control of microbial growth and for the production of biodegradable polymers.

Lactate is in dynamic flux between subcellular compartments, between the cell and the extracellular space and between cells. Because the concentration of lactate in the cell compartments is unknown, the dynamics of lactate in the living body is a largely unknown area.

Standard methods to measure lactate are based on enzymatic reactions, which have to be followed by photometric, amperometric or other devices. Enzyme-based electrodes have been developed that can detect lactate with high-temporal resolution. Another approach to measure lactate is high performance liquid chromatography (HPLC), where lactate is separated from other compounds by passing the sample through a stationary phase stored in a column. There is a problem in the prior art, however, that the existing methods are invasive as they require the extraction of samples or consume lactate, and therefore, they change the concentration of lactate in the sample. A second problem is their sensitivity, since they can not detect the minute amount of lactate present in a single cell or a single subcellular organelle.

The transport of lactate across cellular and subcellular membranes is mediated by the monocarboxylate transporter (MCT), a molecule involved in the pathogenesis of several diseases and an important target for pharmacological intervention in cancer and diabetes. There are no available methods to measure the transport of lactate in single cells. More specifically, current and common techniques used to measure the transport of lactate using radioactive isotopes cannot resolve single cells and have poor temporal resolution, which hampers the study of fast phenomena and normal tissues, which are heterogeneous in their cellular composition. An existing technique infers the transport of lactate in single cells from changes in pH that accompany the transport of lactate, but this technique is limited insofar as requires prior knowledge of the usually unknown buffering capacity of the cell and is not easily applicable in the presence of physiological bicarbonate buffers.

The rates of lactate production and lactate consumption are important parameters of cell metabolism, with relevance for hypoxia/ischemia, cancer, diabetes and other pathological conditions. There are no available methods to measure the rates of lactate production and consumption in single cells. More specifically, current and common techniques used to measure the rates of lactate production and consumption are enzyme-based methods that cannot resolve single cells, have poor temporal resolution, and cannot be applied in the presence of physiological concentrations of lactate. Particularly, measurements using isotopes cannot resolve single cells and have poor sensitivity and temporal resolution. Other currently available technique infers the production of lactate by a cell population by following changes in pH that accompany the production of lactate, but this indirect technique is limited insofar as it is affected by other mechanisms affecting extracellular pH and is not easily applicable in the presence of physiological bicarbonate buffers.

The rate of pyruvate consumption by mitochondria, equivalent under some conditions to the rate of the tricarboxylic acid (TCA) cycle and oxidative phosphorylation, is one of the fundamental parameters of cell metabolism and is affected in several diseases including hypoxic/ischemia, cancer, diabetes and other conditions. There are no available methods to measure the rates of the mitochondrial metabolism in single cells. More specifically, current and common techniques to measure the rates of the mitochondrial metabolism use cannot resolve single cells and have poor sensitivity and low temporal resolution.

In the state of the art there is no evidence of an optical tool or nanosensor for detecting and quantifying lactate in samples, in tissues and in cellular and subcellular compartments, with high spatial and temporal resolution. Also, there are no available techniques to quantitate single-cell resolution lactate transport or the rates of lactate consumption/production or the rate of mitochondrial metabolism or the Warburg effect, the metabolic transformation that underlies cancer. Nevertheless there are related documents in the art, which will be described below. Sensors for different metabolites are described in WO2006096213A1, WO2006-096214A1, WO2006044612A2 and WO2007046786A2 that involve a FRET donor, a FRET acceptor and a member of the class of periplasmic binding proteins (PBPs), proteins located in outside bacterial plasma membranes involved in chemotaxis. The periplasmic binding protein serves as the specific recognition element. As there is no known rule to predict whether a given protein may serve as an effective recognition element, these proteins have been the result of informed trial and error, semi-rational design. The current invention does not used any of the recognition elements described WO2006096213A1, WO2006096214A1, WO2006044612A2 or WO2007046786A2. Moreover, the current invention is not based on any members of the periplasmic binding protein family but rather on a member of the GntR family, a subclass of transcription factors involved in adaptation of bacteria to changing environmental conditions. Surprisingly, the sensor described in the present invention was found to detect its ligand over 4 orders of magnitude, which makes it unique. PBP-based sensors can only quantify ligands over 2 orders of magnitude only.

WO2001033199A2 discloses a probe based on a target binding site peptide (i) attached to a first fluorescent polypeptide capable of binding to (i) and attached to a second fluorescent polypeptide. The probe includes a linker connecting the two fluorescent polypeptides which allows the distance between them to vary, the fluorescent polypeptides display fluorescence resonance energy transfer (FRET) between them. The probe described in WO2001033199A2 is qualitatively different from the probe described in the current invention insofar as the current invention does not involve displacement of binding between two peptides but rather a conformational change elicited by the ligand in a whole protein.

WO2008008149 describes a method to measure the rates of glycolysis and mitochondrial metabolism in cell populations by recording the rate of extracellular oxygen depletion and the rate of extracellular acidification over minutes using a specific dedicated apparatus. The current invention differs from WO2008008149 as it does not need a dedicated apparatus and can be used with standard multi-well plate readers. It also differs in terms of spatial resolution as it can measure single cells and temporal resolution, which is in the order of seconds. The current invention measures the rate of lactate production directly, whereas WO2008008149 provides an indirect estimate by recording the accumulation of extracellular protons, a parameter that is affected by other processes unrelated to metabolism and that required unphysiological pH buffering conditions.

WO/2012/002963 describes a method to estimate the rate of glucose consumption in single cells or cell population with high temporal resolution using a FRET glucose nanosensor. The current invention differs from WO/2012/002963 as is does not measure glucose or the rate of glucose consumption but the rates of lactate production/consumption and the rate of mitochondrial metabolism, rates that are independent of the rate of glucose consumption, being a completely different technical application. Moreover, the present method allows an estimation of the Warburg effect, which is not possible with a glucose nanosensor.

DISCLOSURE OF THE INVENTION

The subject of the present invention is to provide a nanosensor, which allows minimally-invasive measurement of lactate over an extended range of lactate concentration with high sensitivity regardless of the concentration of the probe, which does not consume lactate during measurement, and that can be used to measure lactate in samples, in cells and in subcellular compartments. Further, the subject of the present invention is to provide a measuring method of lactate using the nanosensor. Said method can be used to measure the activity of the lactate transporters, to measure the rates of cellular lactate production and lactate consumption, and to measure the rate of pyruvate consumption by mitochondria, which under certain conditions is equivalent to the rate of the tricarboxylic acid (TCA) cycle, a method for single-cell quantification of the Warburg effect, a transformation of metabolism that characterizes cancer cells, and a method to detect interference between drugs and bioenergetic pathways.

BRIEF DESCRIPTION OF THE INVENTION

The present invention is related to a genetically-encoded Forster resonance energy transfer (FRET)-based indicator composed of the bacterial L1dR transcription factor sandwiched between any suitable donor and acceptor fluorescent proteins moieties that are capable in combination of serving as donor and acceptor moieties in FRET. Preferred donor and acceptor moieties are selected from the group consisting of mTFP (monomeric teal fluorescent protein), CFP (cyan fluorescent protein), BFP (blue fluorescent protein), GFP (green fluorescent protein), YFP (yellow fluorescent protein), enhanced variations thereof such as enhanced YFP (EYFP), Citrine or Venus, or infrared fluorescent proteins from bacterial phytochromes, with a particularly preferred embodiment provided by the donor/acceptor mTFP/YFP Venus, a variant of YFP with improved pH tolerance and maturation time (Nagai et al., 2002). Criteria to consider when selecting donor and acceptor fluorescent moieties is known in the art, for instance as disclosed in U.S. Pat. No. 6,197,928, which is herein incorporated by reference in its entirety. An alternative is the use of a single fluorescent moiety such as circularly-permuted variations of GFP (Akerboom et al., 2008) inserted into the backbone of L1dR or other suitable lactate-binding protein, which undergoes a change in fluorescence intensity in response to binding of lactate to the L1dR moiety or to other suitable lactate-binding protein. In a more preferred embodiment, the fluorescent proteins are mTFP and Venus.

Unexpectedly, the lactate sensor of the present invention shows a biphasic dose response curve with apparent dissociation constants for lactate of 8 μM and 800 μM, which allows quantitation of lactate over four orders of magnitude (from $10^{-6}$ to $10^{-2}$ M), and differs from all existing FRET metabolite nanosensors, which only allow measurement over two orders of magnitude, for example WO2006-096213A1, WO2006096214A1, WO2006044612A2 and WO2007046786A2. The invention also comprises methods that exploit the high spatiotemporal resolution of the lactate sensor of the present invention for the measurement of lactate, which, depending on the configuration of the method, allows the measurement of transport activity and of two metabolic rates, the rate of lactate production/consumption and the rate of pyruvate consumption by mitochondria and a method to quantify the Warburg phenomenon in single-cells. These methods can be applied to single cells or cell populations, adherent cells or in suspension, to a cell culture, a tissue culture, a mixed cell culture, a tissue explant, or it can also be applied to animal tissues in vivo. The method comprises the expression of the lactate sensor of the present invention in individual cells.

The nanosensor of the present invention is expressed in single cells or cell populations, adherent cells or in suspension, in a cell culture, a tissue culture, a mixed cell culture, a tissue explant, or in animal tissues in vivo. The gene expression can be attained by any suitable method to transfer the sensor gene information to the host cell. Examples of gene transfer methodologies are plasmid transfer for instance using liposomal delivery, virus transfer and transgenesis.

Once the sensor is expressed in single cells or cell populations, adherent cells or in suspension, in a cell culture, a tissue culture, a mixed cell culture, a tissue explant, or in animal tissues in vivo, the sensor is calibrated according to pre-established conditions. In order to express fluorescence data in terms of lactate concentration, a single-point calibration protocol is applied at the end of each experiment. Briefly, intracellular lactate is first lowered by depriving the cells of lactate and glucose, a maneuver that inhibits lactate production at Lactate dehydrogenase (LDH). To ensure that cytosolic lactate is indeed negligible, cells are exposed to pyruvate, which on entering via MCT, increases in the number of inward-facing binding sites available for lactate extrusion, effectively "pumping out" the residual lactate. With the value for the fluorescence ratio at this "zero" lactate condition, the kinetic constants determined in vitro, and the maximum change of fluorescence ratio of 38% or the value determined for a each cell type, fluorescence data are converted into lactate concentration as shown in FIG. 12.

The nanosensor of the invention, is further used in a method for determination of lactate concentrations as described before in single cells or cell populations, adherent cells or in suspension, in a cell culture, a tissue culture, a mixed cell culture, a tissue explant, or in animal tissues in vivo. Depending on the configuration of the method for determination of lactate concentrations, in a first embodiment, the use of the nanosensor of the invention, in a method allows the determination of the lactate transporter activity (i.e. estimation of kinetic parameters of lactate transporter).

In a second embodiment, the use of the nanosensor of the invention, in a method allows determination of lactate production and/or consumption rates.

In a third embodiment, the use of the nanosensor of the invention, in a method allows the measurement of mitochondrial pyruvate consumption and/or production rates.

In a further embodiment, the use of the nanosensor of the invention, in a method for single-cell quantification of the Warburg effect.

Both the foregoing summary and the following detailed description provide examples and are explanatory only. Accordingly, the foregoing summary and the following detailed description should not be considered to be restrictive. Further, features or variations may be provided in addition to those set forth herein. For example, certain embodiments may be directed to various feature combinations and sub-combinations described in the detailed description.

BRIEF DESCRIPTION OF THE DRAWINGS

The invention is illustrated by the accompanying drawings wherein:

FIG. 2 shows the amino acid sequences of L1dR from *E. coli* and (SEQ ID NO: 33) *C. glutamicum* (SEQ ID NO: 34).

FIG. 3 shows the alignment of the amino acid sequences of sixteen variants of the lactate sensor, SEQ ID NO 1 corresponding to variant 1, SEQ ID NO 2 corresponding to variant 2, SEQ ID NO 3 corresponding to variant 3, SEQ ID NO 4 corresponding to variant 4, SEQ ID NO 5 corresponding to variant 5, SEQ ID NO 6 corresponding to variant 6, SEQ ID NO 7 corresponding to variant 7, SEQ ID NO 8 corresponding to variant 8, SEQ ID NO 9 corresponding to variant 9, SEQ ID NO 10 corresponding to variant 10, SEQ ID NO 11 corresponding to variant 11, SEQ ID NO 12 corresponding to variant 12, SEQ ID NO 13 corresponding to variant 13, SEQ ID NO 14 corresponding to variant 14, SEQ ID NO 15 corresponding to variant 15, SEQ ID NO 16 corresponding to variant 16.

FIG. 16 compares metabolic rates measured experimentally with those obtained by fitting a mathematical model to the data. In the equation shown in FIG. 16:

Pyruvate concentration, [Pyr] (μM)
Lactate, [Lac] (μM)
Glycolytic pyruvate production, G (μM/s)
Lactate dexydrogenase forward reaction, LDHf (s-1)
Lactate dehydrogenase reverse reaction, LDHr (s-1)
Cellular lactate release, MCT (μM/s)
Mitochondrial pyruvate uptake, PT (μM/s)

Figure 17:
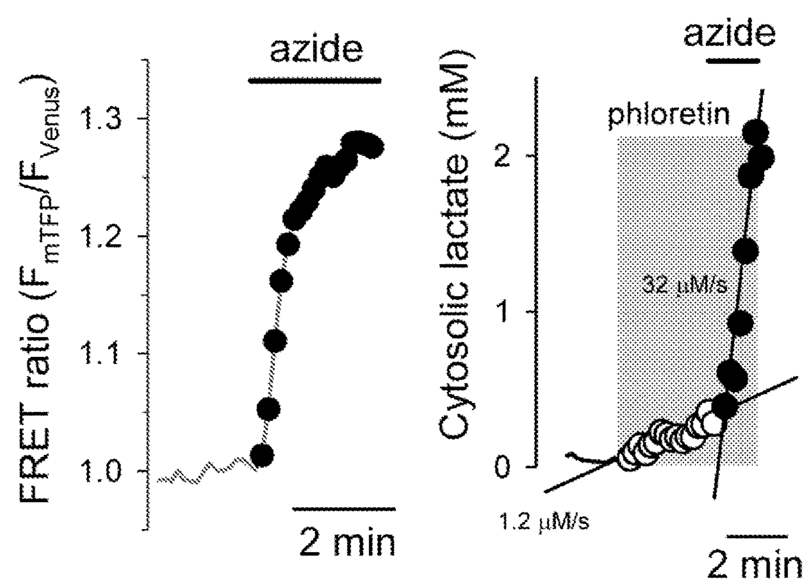

FIG. 17 shows the acute activation of lactate production by inhibition of oxidative phosphorylation.

Figure 18:
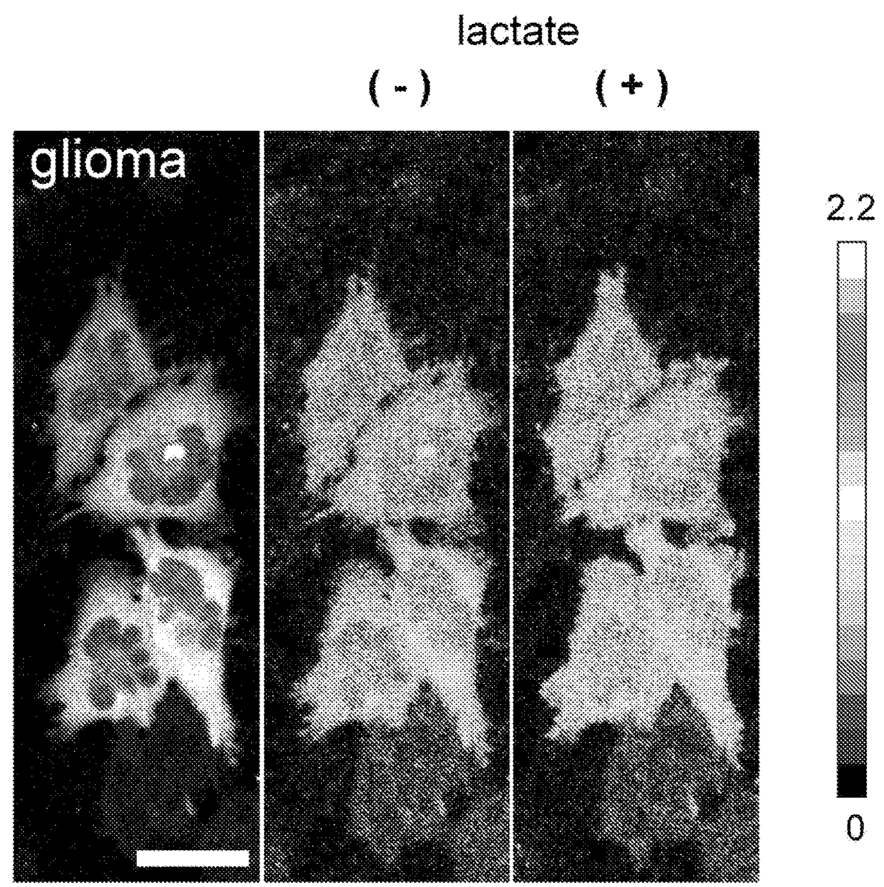

FIG. 18 shows the effect of lactate on Variant 7, expressed in T98G glioma cells.

Figure 19:
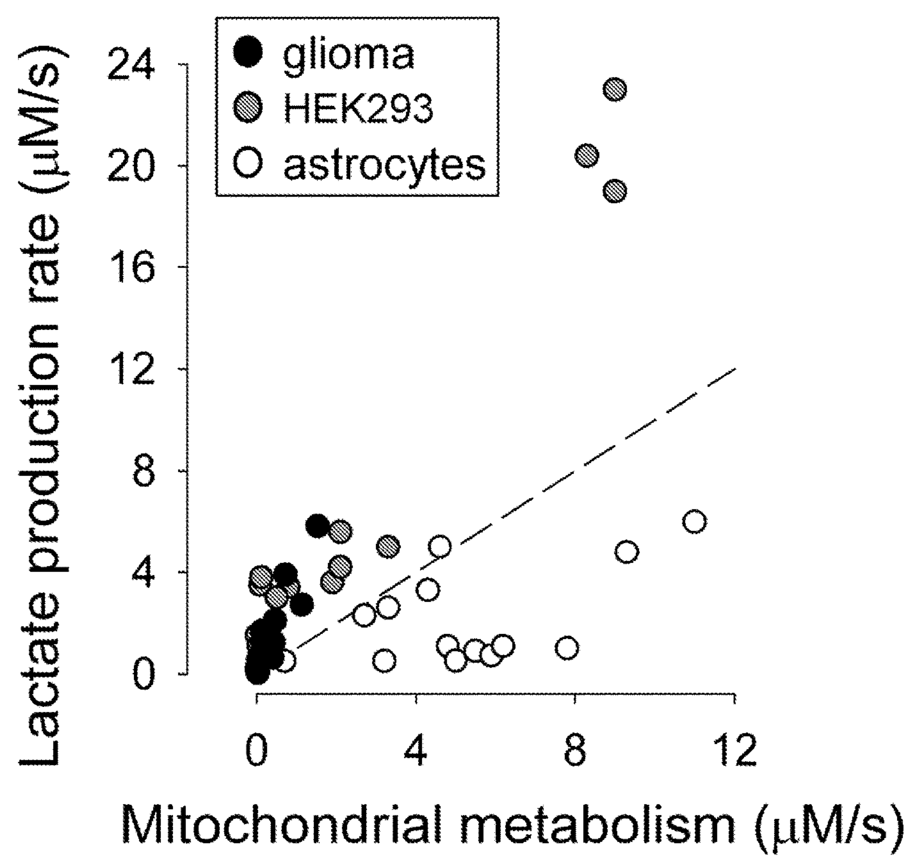

FIG. 19 plots the lactate production rate and mitochondrial metabolism in individual astrocytes, HEK293 cells and T98G glioma cells.

Figure 20:
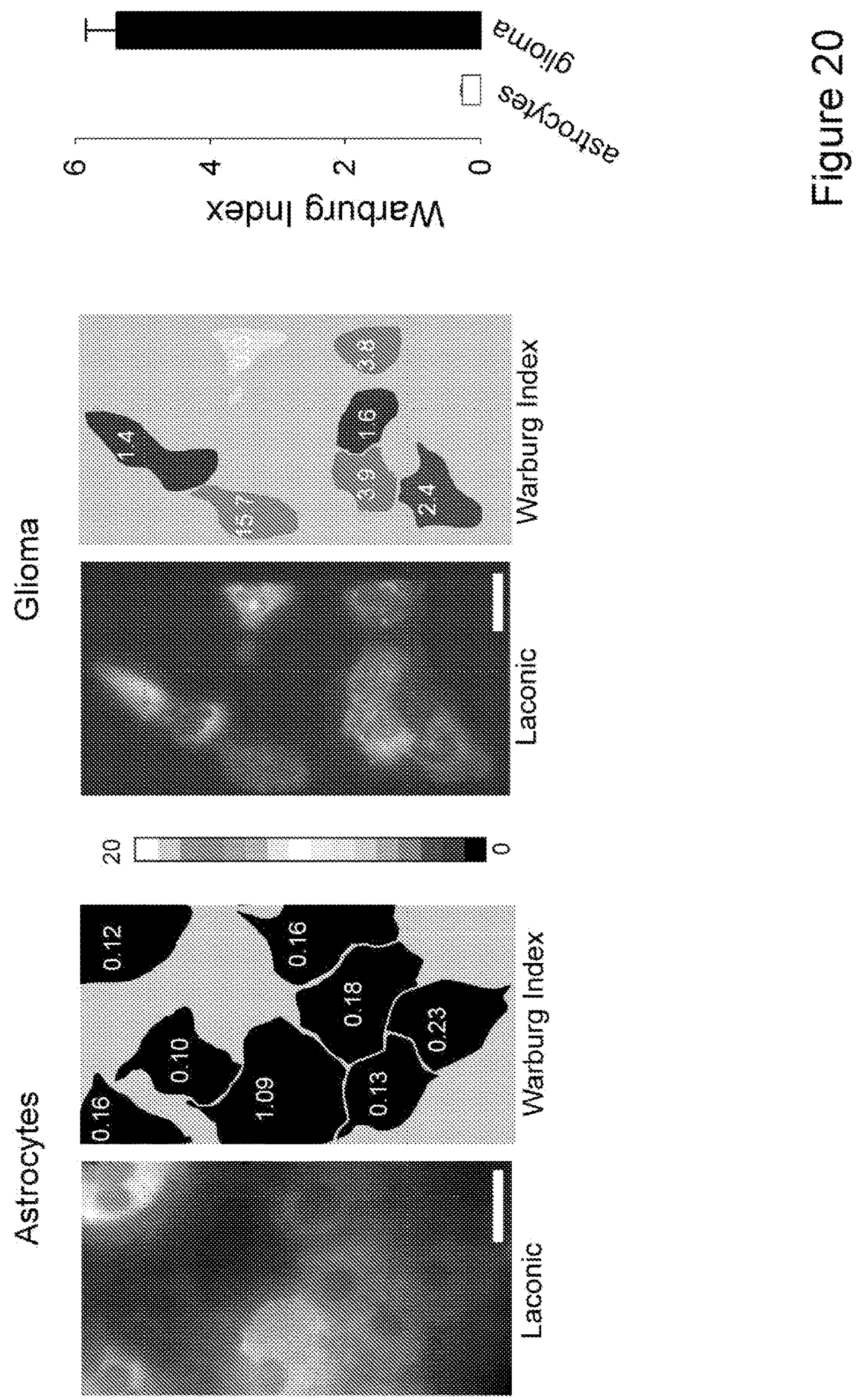

FIG. 20 shows the Warburg Index of astrocytes and glioma cells.

DETAILED DESCRIPTION OF THE INVENTION

The following detailed description refers to the accompanying drawings. While embodiments of the nanosensor of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the scope of the invention. While the nanosensor and the methods are described in terms of "comprising" various elements or steps, the nanosensor and the methods can also "consist essentially of" or "consist of" the various elements or steps, unless stated otherwise. Additionally, the terms "a," "an," and "the" are intended to include plural alternatives, e.g., at least one, unless stated otherwise.

The nanosensor quantifies lactate between 1 μM and 10 mM, allowing single-cell measurement of lactate concentration, lactate transporter (MCT) activity, lactate production and the rate of mitochondrial metabolism, as well as detection of the Warburg effect in individual cells.

The nanosensor of the present invention is a Forster Resonance Energy Transfer (FRET)-based lactate nanosensor further based on L1dR, a bacterial transcription regulator that has two modules, a lactate-binding/regulatory domain and a DNA-binding domain. The L1dR genes were selected from *Corynebacterium glutamicum* and from *Escherichia coli*.

Figure 1:
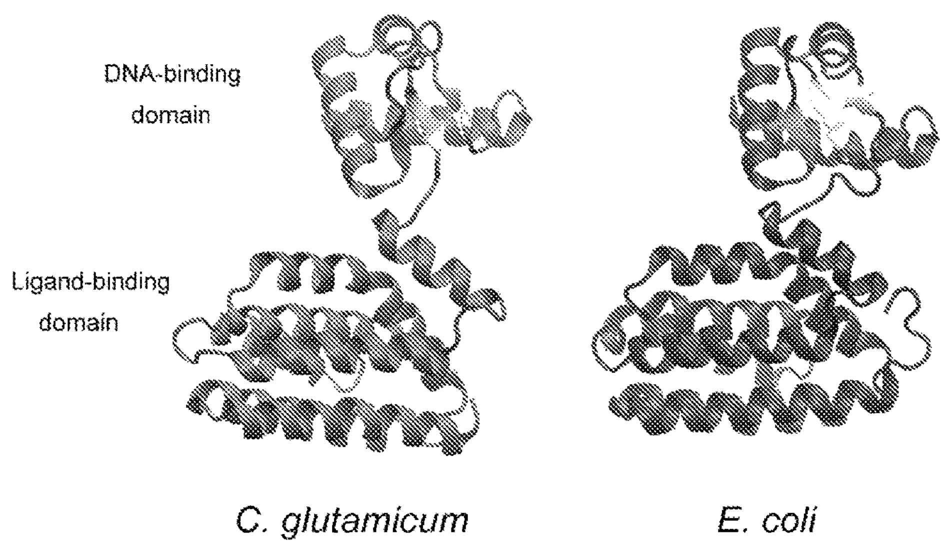
FIG. 1 shows the tridimensional structures of the transcriptional regulator L1dR from *E. coli* and *C. glutamicum.*

The tridimensional structure of the two proteins is virtually superimposable (FIG. 1), yet they are only 19.4% identical, differing in numerous charged residues (FIG. 2), which may alter surface charge scanning and possibly FRET efficiency. The FRET-based lactate nanosensor of the invention may incorporate any suitable donor and acceptor fluorescent proteins moieties that are capable in combination of serving as donor and acceptor moieties in FRET. Preferred donor and acceptor moieties are selected from the group consisting of mTFP (monomeric teal fluorescent protein), CFP (cyan fluorescent protein), BFP (blue fluorescent protein), GFP (green fluorescent protein), YFP (yellow fluorescent protein), enhanced variations thereof such as enhanced YFP (EYFP), Citrine or Venus, or infrared fluorescent proteins from bacterial phytochromes, with a particularly preferred embodiment provided by the donor/acceptor mTFP/YFP Venus, a variant of YFP with improved pH tolerance and maturation time (Nagai et al., 2002). Criteria to consider when selecting donor and acceptor fluorescent moieties is known in the art, for instance as disclosed in U.S. Pat. No. 6,197,928, which is herein incorporated by reference in its entirety. An alternative is the use of a single fluorescent moiety such as circularly-permuted variations of GFP (Akerboom et al., 2008) inserted into the backbone of L1dR or other suitable lactate-binding protein, which undergoes a change in fluorescence intensity in response to binding of lactate to the L1dR moiety or to other suitable lactate-binding protein. A variant of yellow fluorescent protein with fast and efficient maturation for cell-biological applications. Nagai T, Ibata K, Park E S, Kubota M, Mikoshiba K, Miyawaki A. Nat Biotechnol. 2002 January; 20(1): 87-90. Crystal structures of the GCaMP calcium sensor reveal the mechanism of fluorescence signal change and aid rational design. Akerboom J, Rivera J D, Guilbe M M, Malavé E C, Hernandez H H, Tian L, Hires S A, Marvin J S, Looger L L, Schreiter E R. J Biol Chem. 2009 Mar. 6; 284(10):6455-64. Epub 2008 Dec. 18.

In a more preferred embodiment, the FRET pair selected was mTFP and Venus, which compared with CFP and YFP are respectively brighter and less pH-sensitive.

The general architecture search for structural combinations of the sensors is shown in FIG. 1*a*, with mTFP located at the N-terminus, the L1dR flanked by linkers, and Venus located at the C-terminus.

Three constructs were generated for each bacterial species, differing with respect to the presence of DNA binding domain and linkers (FIG. 3). A comparative analysis showed that three proteins that changed their fluorescence in response to lactate, showed that constructs with L1dR from *E. coli* changed their fluorescence ratio much more than those from *C. glutamicum*. The list of sequences comprises different embodiments of the invention, which should not be considered as limiting of the invention.

In a further embodiment, the present invention includes lactate nanosensors described according to the amino acid sequences and have at least 60%, 70%, 80% 85%, 90%, 95%, or 99% sequence identity with SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, or SEQ ID NO 16.

The present invention also considers the nucleic acid sequences having at least 60%, 70%, 80% 85%, 90%, 95%, or 99% sequence identity with SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, or SEQ ID NO 32.

The sequences described in SEQ ID NO 1 to SEQ ID NO 16 are only particular embodiments of the present invention provided as way of exemplification of the present invention, and should not be considered to limit the scope of the invention.

Figure 4:
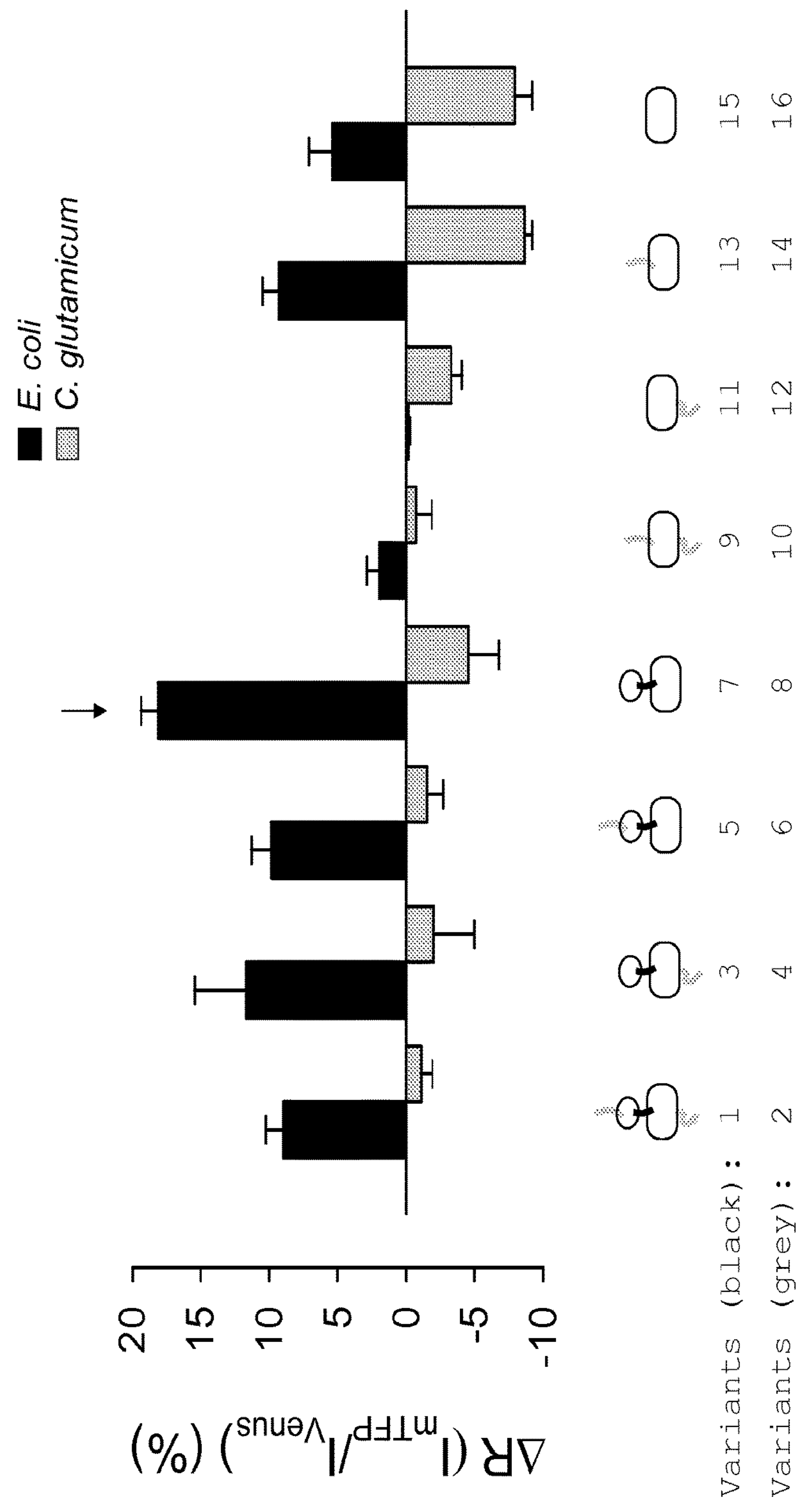
FIG. 4 shows the response to lactate of sixteen variants of the lactate sensor, wherein the black filled bars correspond to the variants 1, 3, 5, 7, 9, 11, 13, 15, and the grey filled bars correspond to variants 2, 4, 6, 8, 10, 12, 14, and 16.
Figure 5:
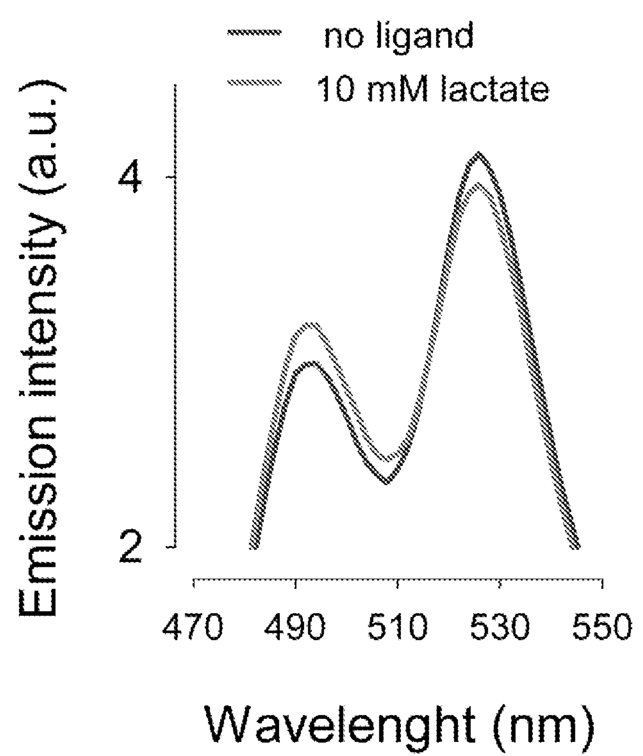
FIG. 5 shows the effect of lactate on the fluorescence emission spectrum of the most responsive variant of the sensor, Variant 7, which is encoded by SEQ ID NO 7.
Figure 6:
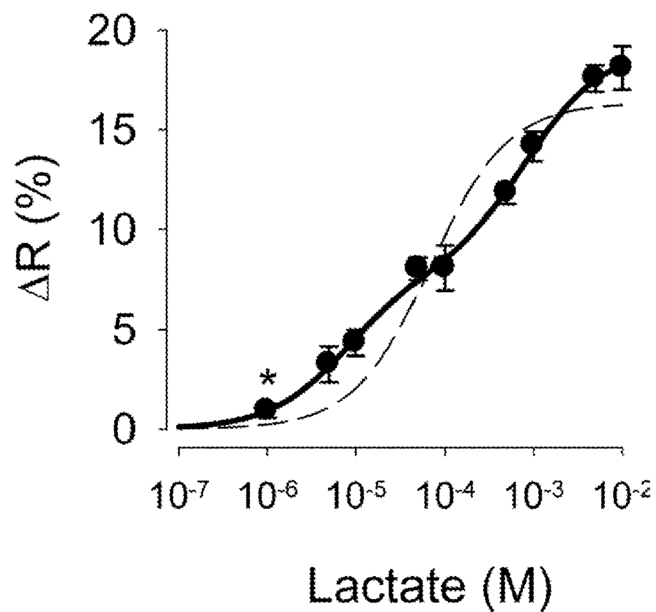
FIG. 6 presents the change in fluorescence ratio of Variant 7, in response to increasing concentrations of lactate.

Also surprising was the observation that the DNA-binding domain is important for the FRET change, and that the sensors with no linkers are more responsive (FIG. 4). The most responsive variant, arrowed in FIG. 4, was chosen for further characterization. It contains the full length L1dR from *E. coli* and no linkers. The emission spectrum of this nanosensor showed the expected peaks of mTFP and Venus at 492 nm and 526 nm, respectively (FIG. 5). The affinity constant of L1dR for L-lactate is not known. FIG. 6 shows that this nanosensor responded to a wide range of the ratio between mTFP and Venus. Fluorescence (at 430 nm excitation) was measured at increasing lactate concentrations, behavior well represented by a double rectangular hyperbola, with apparent dissociation constant (KD) values of 8±2 μM and 830±160 μM, and respective maximum ΔR values of 8±0.4% and 11±0.4%. This unique property of L1dR confers the lactate sensor the desirable ability of reporting across four orders of magnitude (from 1 μM to 10 mM), instead of the two orders afforded by one-site sensors.

When used in vitro, the sensitivity of this nanosensor is similar to at least the most sensitive enzyme-based commercially available kit (50 pmoles).

Figure 7:
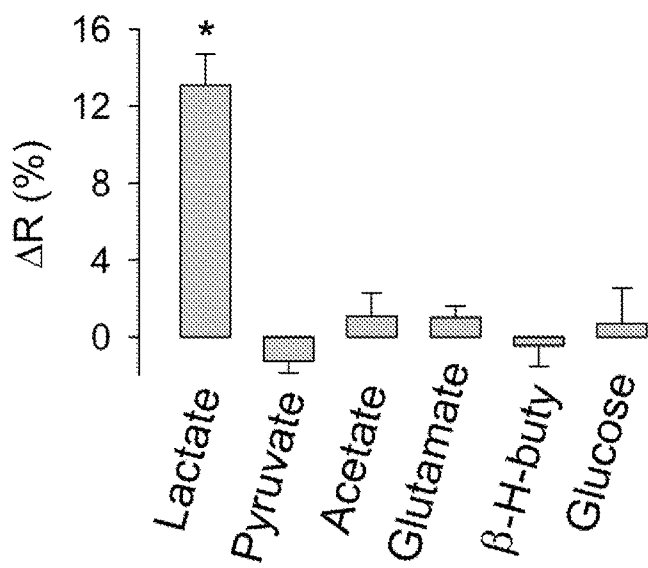
FIG. 7 summarizes the effect of several molecules on the fluorescence ratio of Variant 7, showing the specificity of the nanosensors.
Figure 8:
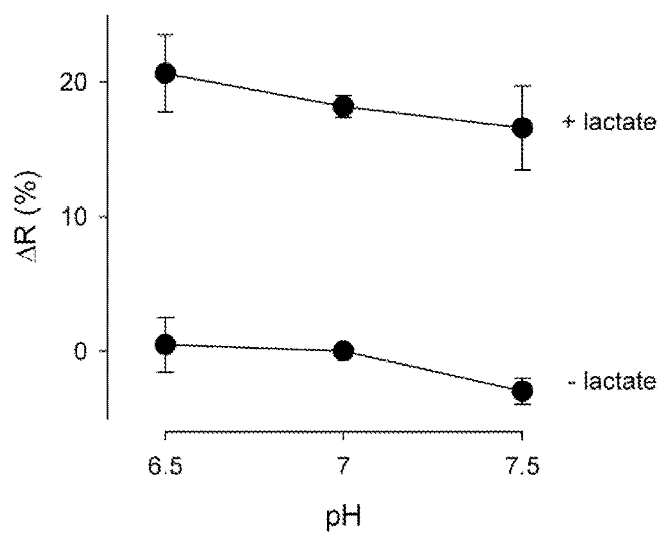
FIG. 8 shows the effect of pH on the fluorescence ratio of the lactate sensor of the present invention.
Figure 9:
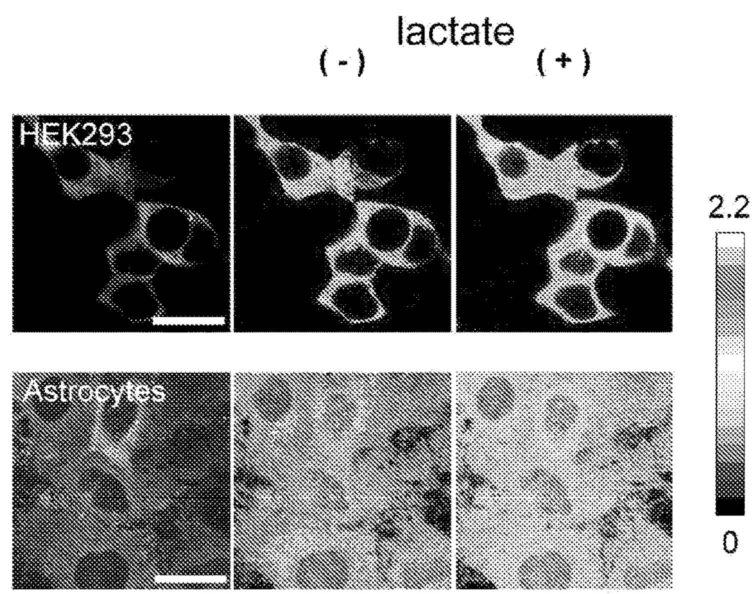
FIG. 9 shows the effect of extracellular lactate on the fluorescence ratio of Variant 7, expressed in HEK293 cells and astrocytes.
Figure 10:
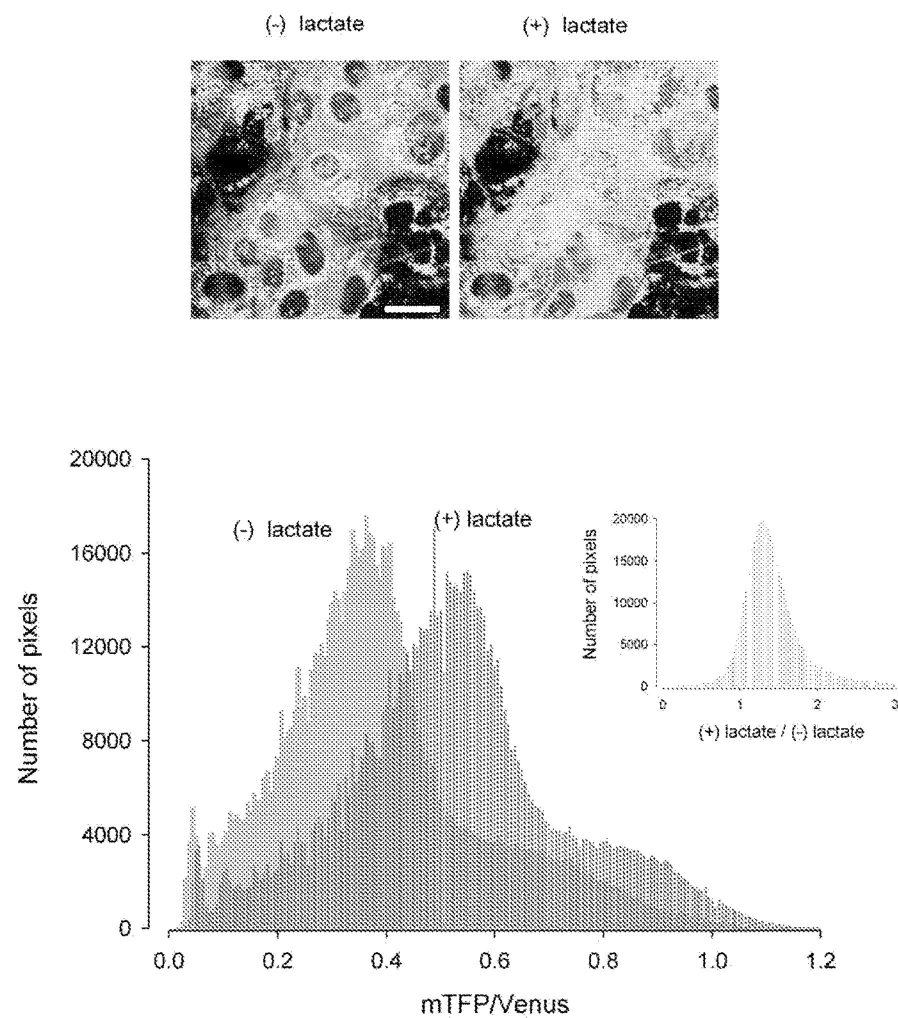
FIG. 10 shows that sensor concentration does not affect the response of Variant 7, to lactate.
Figure 11:
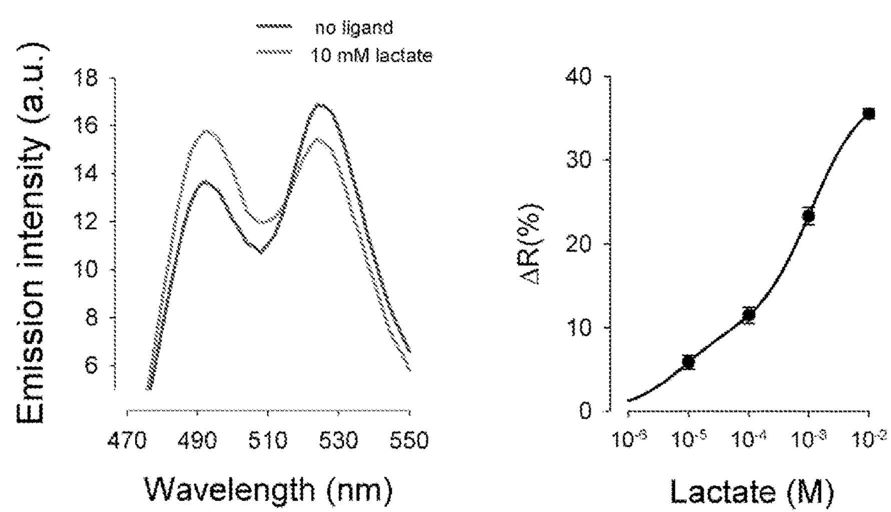
FIG. 11 shows the emission spectra and dose-response of Variant 7, encoded by SEQ ID NO 1, expressed in HEK293 cells.
Figure 12:
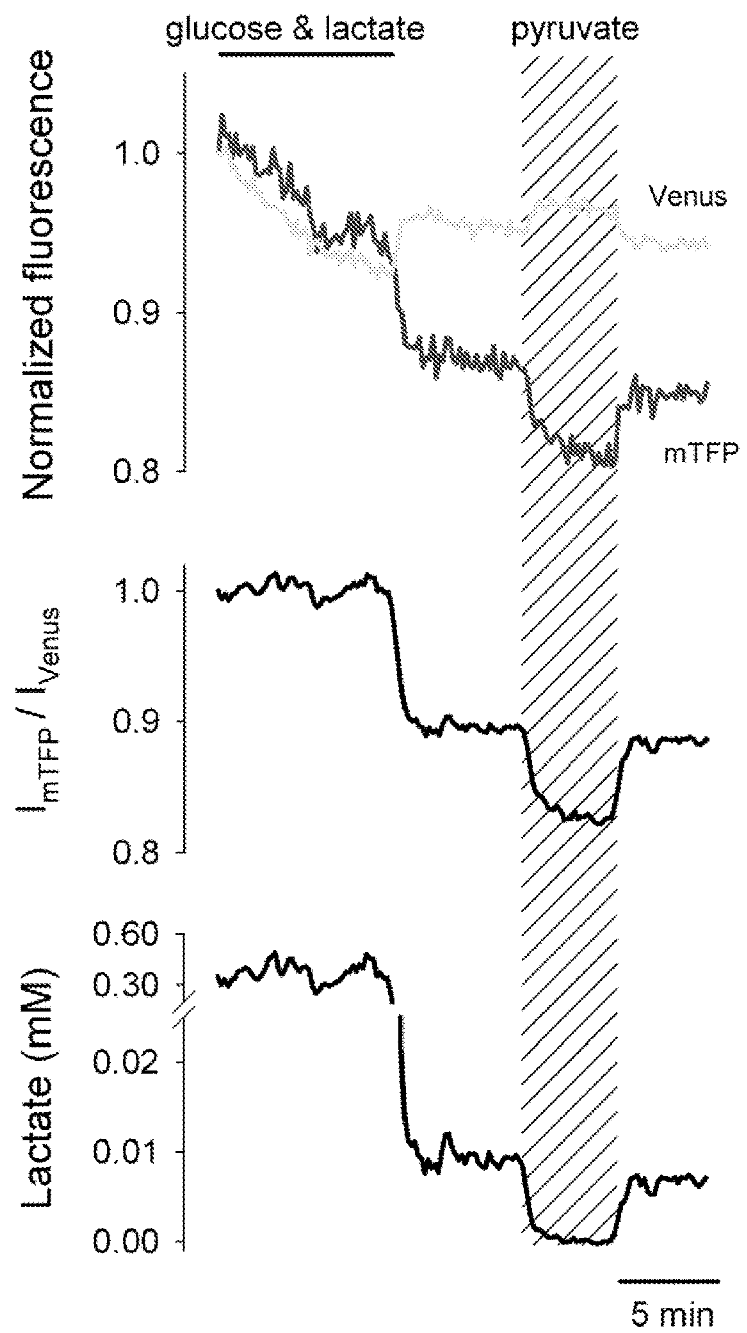
FIG. 12 illustrates a one-point calibration protocol for Variant 7, encoded by SEQ ID NO 1.

The specificity was investigated by exposing the sensor to millimolar levels of several organic acids and glucose, of which only lactate induced a significant change in FRET (FIG. 7). The sensor showed a modest sensitivity to pH in the physiological range (FIG. 8). Expressed in mammalian cells, the lactate sensor of the present invention distributed in the cytosol and was excluded from nuclei and organelles (FIG. 9). Compared to the glucose sensor, its distribution was more heterogeneous, possibly due to L1dR multimerization, but this did not affect the response to lactate (Supplementary FIG. 10). Expressed in cells, the sensor showed emission spectra and two-component dose-response curve similar to that observed in vitro, but with a larger change in FRET ratio (FIG. 11). In order to express fluorescence data in terms of lactate concentration, a single-point calibration protocol is applied at the end of each experiment. Briefly, intracellular lactate is first lowered by depriving the cells of lactate and glucose, a maneuver that decreases the glycolytic flux and lowers the cytosolic NADH:NAD+ ratio (Hung et al., 2011; Zhao et al., 2011), inhibiting lactate production at Lactate dehydrogenase (LDH). To ensure that cytosolic lactate is indeed negligible, we use a property of MCTs termed trans-acceleration or accelerated exchange (Halestrap and Price, 1999). Cells are exposed to pyruvate, which on entering via MCT, increases in the number of inward-facing binding sites available for lactate extrusion, effectively "pumping out" the residual lactate. With the value for the fluorescence ratio at this "zero" lactate condition, the kinetic constants determined in vitro, and the maximum change of fluorescence ratio of 38% or the value determined in the specific cell type, fluorescence data were converted into lactate concentration as shown in FIG. 12. After 20 minutes of glucose/lactate deprivation in HEK293 cells or neurons, or 1 hour deprivation in astrocytes, intracellular lactate is undetectable (data not shown), consistent with the very low NADH:NAD+ ratio present under such conditions (Hung et al., 2011; Zhao et al., 2011).

The invention further comprises methods using the aforementioned nanosensor for determination of lactate concentrations in single cells or cell populations, adherent cells or in suspension, in a cell culture, a tissue culture, a mixed cell culture, a tissue explant, or in animal tissues in vivo.

The method comprises the general steps of:

a) Expressing the nanosensor of the invention, in a desired host, such as single cells or cell populations, adherent cells or in suspension, in a cell culture, a tissue culture, a mixed cell culture, a tissue explant, or in animal tissues in vivo;
b) Calibrating the host with predetermined values of intracellular, extracellular, subcellular lactate concentrations, recording lactate concentrations in time;
c) Disrupting the steady-state of lactate entering the cell;
d) Recording the output from the nanosensor calculating the lactate concentration at different time points;

In the step b), corresponding to calibrating the host, the nanosensor of the invention is calibrated in cells using the kinetic constants of the sensor obtained in vitro and a zero-lactate level determined in the presence of pyruvate. Pyruvate can be in the range of 5 mM to 20 mM, preferentially 10 mM.

The general method can be applied in different configurations, for example, in a first embodiment, the nanosensor is used in a method for the measurement of the activity of the lactate transporter.

In this first embodiment, with the information obtained in the calibration step, the disruption of the steady-state of lactate entering the cell is carried out by altering the extracellular concentration of lactate, thus exposing the cells to lactate. This causes a rise in intracellular lactate that is monitored with the lactate sensor and whose initial rate is independent of lactate metabolism and can be used to estimate kinetic parameters. Exposure of the cells to increasing concentrations of lactate allows the estimation of kinetic parameters for the lactate transporter. Kinetic parameters are also obtained from the decrease in intracellular lactate after removal of extracellular lactate.

In a second embodiment, the general method can be applied to a method to measure the rates of lactate production and lactate consumption. In this second embodiment, with the information obtained in the calibration step, the steady-state of lactate is disrupted by altering the function of lactate transporter, for example by addition of a blocker of the lactate transporter. In mammalian cells, the lactate transporter is the MCT and can be blocked with phloretin, parachloromercurybenzoate or other suitable compounds. If the cell is a net lactate producer, application of the MCT-blocker causes an increase in intracellular lactate concentration, the initial rate of which is equal to the rate of cellular lactate production in the steady-state. If the cell is a net lactate importer, application of the MCT-blocker causes a fall in intracellular lactate concentration, the initial rate of which is equal to the rate of lactate consumption on the steady-state. In a more particular embodiment, the disruption of the steady-state is attained by adding an inhibitor of the MCT, such as, but not limited to phloretin, parachloromercurybenzoate, anti-MCT antisera, etc. In cells where lactate transport is mediated by other transporters, the method can be applied using their respective inhibitors. A critical property of this nanosensor that allows quantitation of these rates is its high temporal resolution, for only the initial rate of lactate accumulation is informative and after a few seconds other non-linear processes like inhibition of glycolysis by the increasing lactate or changes in mitochondrial pyruvate uptake may interfere with the measurement. Because of its low temporal resolution, extracellular lactate measurement by existing techniques cannot be used in combination with MCT-blockage to estimate the rates of lactate production or lactate consumption.

In a third embodiment, the general method can be applied to a method to measure the rate of mitochondrial pyruvate consumption.

In this third embodiment, with the information obtained in the calibration step, the disruption in the lactate steady-state is caused by disrupting the flux of lactate. To quantitate the rate of mitochondrial pyruvate consumption, the steady-state is disrupted by addition of a blocker of the mitochondrial pyruvate transporter. In mammalian cells, the mitochondrial pyruvate transporter can be blocked with low concentration of 4-CIN. In cells, the concentration of pyruvate and lactate move together as a single pool because of fast interconversion by the high activity enzyme lactate dehydrogenase (LDH), with lactate representing over 90% of the pool. Application of the pyruvate transporter-blocker 4-CIN or other suitable inhibitor of the mitochondrial pyruvate transporter, causes an increase in the intracellular lactate concentration, the initial rate of which is equal to the rate of pyruvate uptake in the steady-state. In cells were pyruvate uptake into mitochondria were mediated by other transporters, the method could be applied using their respective inhibitors. A critical property of this nanosensor that allows quantitation of these rates is its high temporal resolution, for only the initial rate of lactate accumulation is informative and after a few seconds other non-linear processes MCT-transport and inhibition of glycolysis by increasing lactate may interfere with the measurement. In the steady-state and in the presence of glucose and lactate as exclusive oxidative substrates, the rate of pyruvate consumption by mitochondria is equal to the rate of the tricarboxylic acid (TCA) cycle and equal to rate of oxidative phosphorylation (OXPHOS).

A fourth particular embodiment of the method of the present invention is determination of cancer staging by estimation of the ratio between lactate production and the rate of the TCA cycle in a sample. Cancer cells are less oxidative than normal cells, a phenomenon known as the Warburg effect, which is receiving renewed attention regarding cancer pathogenesis, diagnosis and possibly treatment. Robust flux through glycolysis and pentose phosphate pathways in these cells are thought to provide building blocks for proliferation and a high redox tone, while the lactic acid exported acidifies the environment and facilitates tumor migration and metastasis. A plot of lactate production versus TCA cycle rate shows that T98G glioma cells can be distinguished from normal astrocytes (FIG. 3*a-b*), but a more sensitive parameter is the ratio between lactate production and the rate of the TCA cycle, which we have termed Warburg Index (FIG. 3*c*). In an alternative embodiment, the Warburg Index is estimated by calculating the ratio between lactate production (with phloretin or other MCT blocker) and the rate of intracellular lactate increase in response to inhibition of oxidative phosphorylation with azide or other suitable compound (FIG. 17), which is a parameter of how oxidative is the cell. This alternative version of the Warburg index gives a different value but is also very sensitive to the mitochondrial defects that characterize cancer cells, senescent cells and other conditions that produce the Warburg phenomenon.

These tools allow the functional study of cancer metabolism with single-cell resolution and are also readily adaptable to multi-well format for high-throughput analysis of metabolism in cancer and other diseases. The development of a sensor based on L1dR provides the basis for creating a wide variety of novel indicators because the GntR superfamily, of which L1dR is a member, has 270 other transcription factors that bind pyruvate, fatty acids, amino acids, TCA cycle intermediates, etc., which are possible candidates to serve as templates for genetically-encoded nanosensors.

Based on the lactate nanosensor of this invention, methods are presented that allow for the first time single-cell real-time quantification of the rates of lactate production and of the tricarboxylic acid (TCA) cycle. Both methods follow cytosolic accumulation of lactate immediately after blockage of selected transporters, in analogous fashion to the measurement of the rate of glucose consumption with a glucose sensor. In the steady-state, the intracellular concentration of lactate is kept constant by a dynamic balance between glycolytic production and lactate efflux (FIG. 2*c*). Perturbation of the steady-state by addition of an MCT blocker like phloretin is expected to cause intracellular lactate accumulation at a rate equal to the rate of lactate production. For net lactate importers, like liver cells and possibly neurons, the MCT blocker should decrease intracellular lactate at a rate equal to the rate of lactate consumption. A similar rationale can be applied to the quantification of pyruvate consumption by mitochondria. The high activity of lactate dehydrogenase (LDH) in mammalian cells, couples the concentrations of lactate and pyruvate, which for this purposes can be considered as a single pool, with lactate representing >90%. Acute inhibition of the mitochondrial pyruvate transporter (PT) with a low concentration of α-Cyano-4-hydroxycinnamate (4-CIN) should produce an accumulation of intracellular lactate, at the rate of pyruvate consumption, which in the absence of alternative mitochondrial substrates is equivalent to the rates of the TCA cycle and oxidative phosphorylation. Experimental demonstration of these methods is provided in FIG. 2*d*. On average, astrocytes presented a lactate production rate of 2 μ/s and a TCA cycle rate of 7.6 μM/s, consistent with their rate of glucose consumption of 2-6 μM/s[11]. Typical of cell lines, HEK293 cells were more glycolytic and less oxidative than astrocytes, with respective rates of lactate production and TCA cycle of 5.4 and 2.1 μM/s. Inhibition of mitochondrial ATP production with sodium azide caused a 26±4 fold increase in the rate of lactate production, fitting the deviation of all pyruvate flux towards lactate production and the 3-4 fold increase observed in glucose consumption (FIG. 2*e*). Fitting a mathematical model to actual lactate measurements indicated that the initial slopes of the changes in lactate concentration triggered by the transport blockers underestimate the actual rates of lactate production and TCA cycle by less than 10% (Supplementary FIG. 7).

The following examples are provided to help in the understanding of the present invention, and should not be considered a limitation to the scope of the invention.

EXAMPLES

In order to help understanding the invention, the present invention will be explained with reference to specific examples:

Protein Purification. Plasmid constructs were transformed into *E. coli* BL21 (DE3). A single colony was inoculated in 100 ml of LB medium with 100 mg/ml ampicillin (without IPTG) and shaken in the dark for 2-3 days. Cells were collected by centrifugation at 5000 rpm (4° C.) for 10 min and disrupted by sonication (Hielscher Ultrasound Technology) in 5 mL of Tris-HCl buffer pH 8.0. A cell-free extract was obtained by centrifugation at 10,000 rpm (4° C.) for 1 hour and filtering of the supernatant (0.45 μm). Proteins were purified using a Nickel resin (His Bin® from Novagen) as recommended by the manufacturer. Eluted proteins were quantified using the Biuret method and stored at −20° C. in 20% glycerol. The variant that showed the largest change in fluorescence ratio, was cloned into pcDNA3.1(−) for expression in eukaryotic cells using the restriction sites BamHI and HindIII.

Animals and Cell Cultures. Animals used were mixed F1 male mice (C57BL/6J×CBA/J), kept in an animal room under Specific Pathogen Free (SPF) conditions at a room temperature of 20±2° C., in a 12/12 h light/dark cycle with free access to food and water. Experiments were approved by the Centro de Estudios Cientificos Animal Care and Use Committee. Mixed cortical cultures of neuronal and glial cells (1-3 day-old neonates) were prepared as described (Loaiza et al., 2003). HEK293 and T98G glioma cells were acquired from the American Tissue Culture Collection and cultured at 37° C. in 95% air/5% $CO_2$ in DMEM/F12 10% fetal bovine serum. Cultures were transfected at 60% confluence using Lipofectamine 2000 (Gibco) or alternatively, exposed to $5\times10^6$ PFU of Ad lactate sensor of the present invention (Vector Biolab), and studied after 24-72 h.

Fluorescence Measurements. Nickel-purified proteins were resuspended at 100 nM in an intracellular buffer containing (mM): 10 NaCl, 130 KCl, 1.25 MgSO4 and 10 HEPES, pH 7.0, and measured with a microplate reader analyzer (EnVision, PerkinElmer). The proteins were excited at 430 nm and the intensity of fluorescence emission of mTFP and Venus were recorded at 485 nm (FmTFP) and 528 nm (FVenus), respectively. The ratio (R) between FmTFP and FVenus was used to characterize the sensors. Emission spectra were obtained at 430 nm excitation, with 2 nm windows. Cells were imaged at room temperature (22-25° C.) in a 95% air/5% $CO_2$-gassed solution of the following composition (in mM): 112 NaCl, 1.25 $CaCl_2$, 1.25 $MgSO_4$, 1-2 glucose, 10 HEPES, 24 $NaHCO^3$, pH 7.4, with 3 mM KCl (astrocytes) or 5 mM KCl (HEK and T98G) using an upright Olympus FV1000 Confocal Microscope equipped with a 20× water immersion objective (N.A. 1.0) and a 440 nm solid-state laser. Alternatively, cells were imaged with an Olympus IX70 or with an Olympus BX51 microscope equipped with a 40× oil-immersion objective (NA 1.3) or with a 20× water-immersion objective (NA 0.95). Microscopes were equipped with CAIRN monochromators (Faversham, UK), and either a Hamamatsu Orca camera controlled by Kinetics software or a Rollera camera controlled with Metafluor software, respectively. For nanosensor ratio measurements, cells were excited at 430 nm for 0.2-0.8 s. Emission was divided with a CAIRN Optosplit, equipped with band pass filters at 480±20 (FmTFP) and 535±15 nm (FVenus). The ratio between FmTFP and FVenus was used to measure lactate. The pH-sensitive dye BCECF was ester loaded at 0.1 μM for 3-4 min and the signal was calibrated by exposing the cultures to solutions of different pH after permeabilizing the cells with 10 μg/ml nigericin and 20 μg/ml gramicidin in an intracellular buffer. BCECF was sequentially excited at 440 and 490 nm (0.05 s) and imaged at 535±15 nm.

Mathematical Modeling of Lactate Dynamics. A model of intracellular lactate dynamics was generated according to the flux diagram in FIGS. 14 and 16, in the absence of extracellular lactate, $$d[Pyr]/dt=(G+[Lac]*LDHr-[Pyr]*LDHf-PT)/vol \quad d[Lac]/dt=([Pyr]*LDHf-[Lac]*LDHr-VMCT/\{KMCT+[Lac]\})/vol$$

where [Pyr] is cytosolic pyruvate concentration, [Lac] is cytosolic lactate concentration, G is glycolytic pyruvate production, LDHf and LDHr are the lactate dehydrogenase forward and reverse reactions and PT is mitochondrial pyruvate uptake. MCT efflux obeys Michaelis-Menten kinetics with maximum rate VMCT and an apparent affinity KMCT (5 mM). The kinetic model was solved numerically with the computer software Berkeley Madonna using the Rosenbrock method.

Statistical Analysis. All time courses correspond to single cells. Experiments were repeated three to six times, with 6-12 cells per experiment. Regression analyses were carried out with the computer program SigmaPlot (Jandel). Differences in mean values of paired samples were evaluated with the Student's t-test. P values<0.05 were considered significant and are indicated with an asterisk (*).

Sixteen different variants of the lactate nanosensor, according to different embodiments of the present invention were produced. FIG. 4 shows the response to lactate of the sixteen variants of the lactate sensor, wherein the black filled bars correspond to the variants 1, 3, 5, 7, 9, 11, 13, 15, and the grey filled bars correspond to variants 2, 4, 6, 8, 10, 12, 14, and 16. Each of the produced variants of the lactate nanosensor of the present invention are encoded by the aminoacid sequence described in the list, SEQ ID NO 1 corresponding to variant 1, SEQ ID NO 2 corresponding to variant 2, SEQ ID NO 3 corresponding to variant 3, SEQ ID NO 4 corresponding to variant 4, SEQ ID NO 5 corresponding to variant 5, SEQ ID NO 6 corresponding to variant 6, SEQ ID NO 7 corresponding to variant 7, SEQ ID NO 8 corresponding to variant 8, SEQ ID NO 9 corresponding to variant 9, SEQ ID NO 10 corresponding to variant 10, SEQ ID NO 11 corresponding to variant 11, SEQ ID NO 12 corresponding to variant 12, SEQ ID NO 13 corresponding to variant 13, SEQ ID NO 14 corresponding to variant 14, SEQ ID NO 15 corresponding to variant 15, SEQ ID NO 16 corresponding to variant 16. Most of the variants showed a measureable change in fluorescence ratio in response to lactate and may be used for the different methods described in the present invention. The high rate of successful sensor generation shows a surprising robustness of L1dR as a scaffold for FRET-based sensor generation.

Example 1

Figure 13:
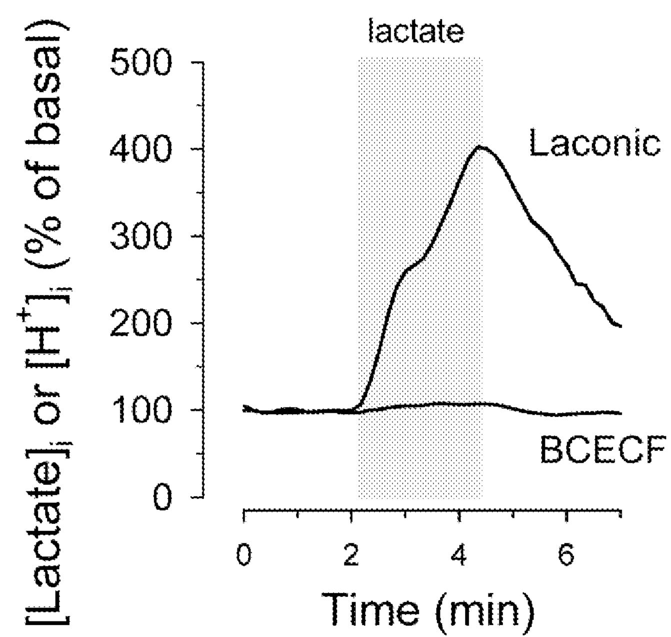
FIG. 13 compares the uses of lactate and pH measurements for the characterization of the lactate transporter in astrocytes.
Figure 15:
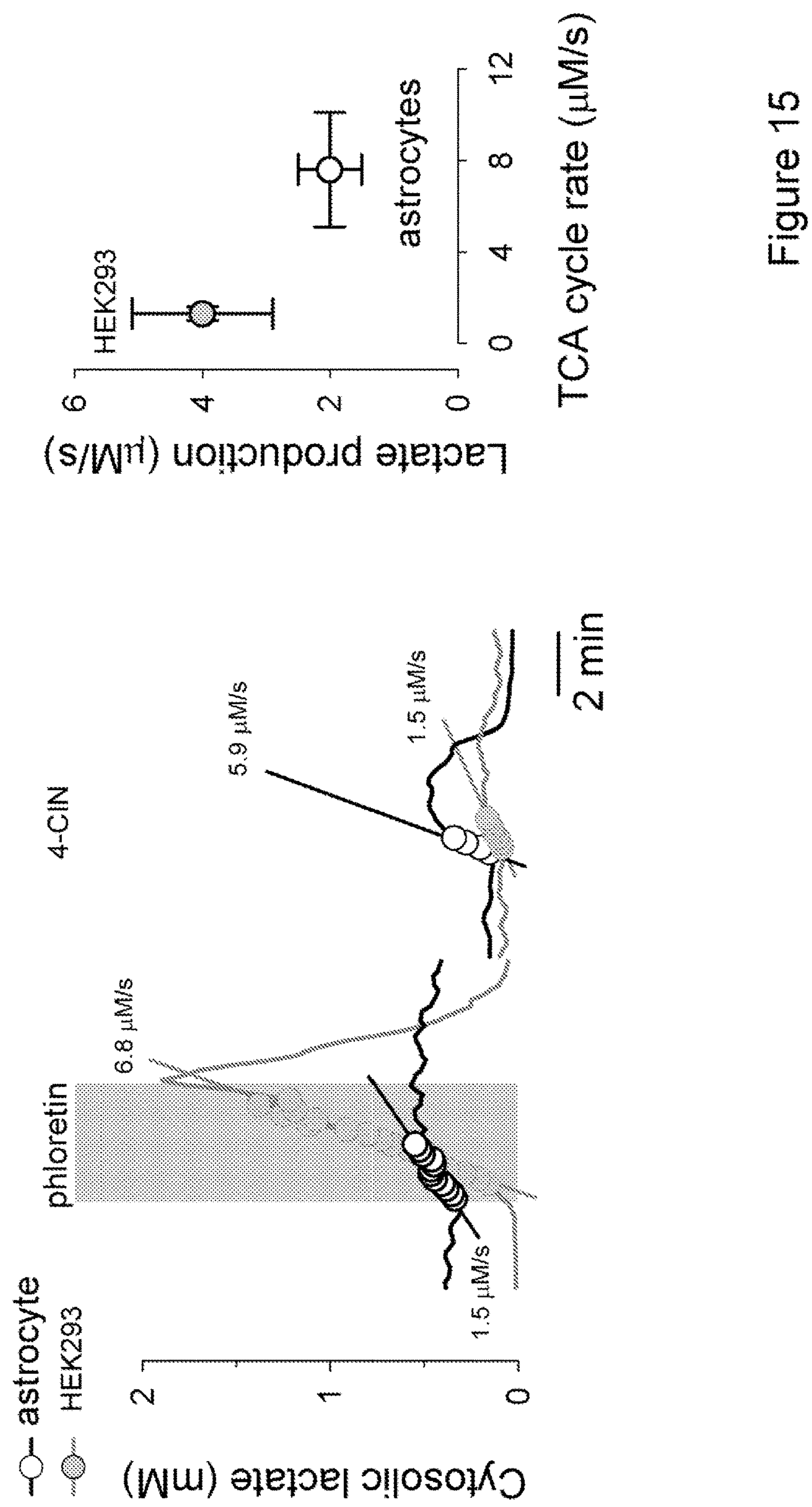
FIG. 15 demonstrates the measurement of cellular lactate production rate and mitochondrial pyruvate consumption rate in single astrocytes and HEK293 cells.

Method for the Measurement of Lactate Transporter Activity with High Spatiotemporal Resolution By controlling the exchange of lactate between cells and the interstitial space, MCTs are nodal points of tissue metabolism. MCTs catalyze the stoichiometric translocation of lactate and a proton and their activity can be measured with single-cell resolution by monitoring intracellular pH with a dye such as BCECF. However, 99.9% of protons are bound to proteins, phospholipids and other sites, and are exchanged through many transporters other than the MCT, which makes pH an imperfect proxy for lactate. To compare the performances of the lactate sensor of the present invention and BCECF, we chose astrocytes. When expressed in astrocytes, the lactate sensor of the present invention responded well to extracellular lactate, allowing real-time monitoring of lactate influx and efflux (FIG. 13). Consistent with an MCT-mediated process, the initial rate of astrocytic uptake of 1 mM lactate of 1.6±0.5 μM/s was inhibited by 96±1% in the presence of the MCT blocker phloretin (50 μM). In contrast, exposure to extracellular lactate produced only a small change in intracellular pH as detected with BCECF (FIG. 15). Thus, the lactate sensor can be used to measure MCT, allowing a more sensitive and physiological characterization of their function. Lactate may also be transported independently of protons through gap junctions (Rouach et al., 2008) and possibly through connexin hemichannels and pannexin channels, fluxes that are invisible to pH measurements and that may now be measured with the present invention.

Example 2

Metabolic Rate of Pyruvate Consumption by Mitochondria

Figure 14:
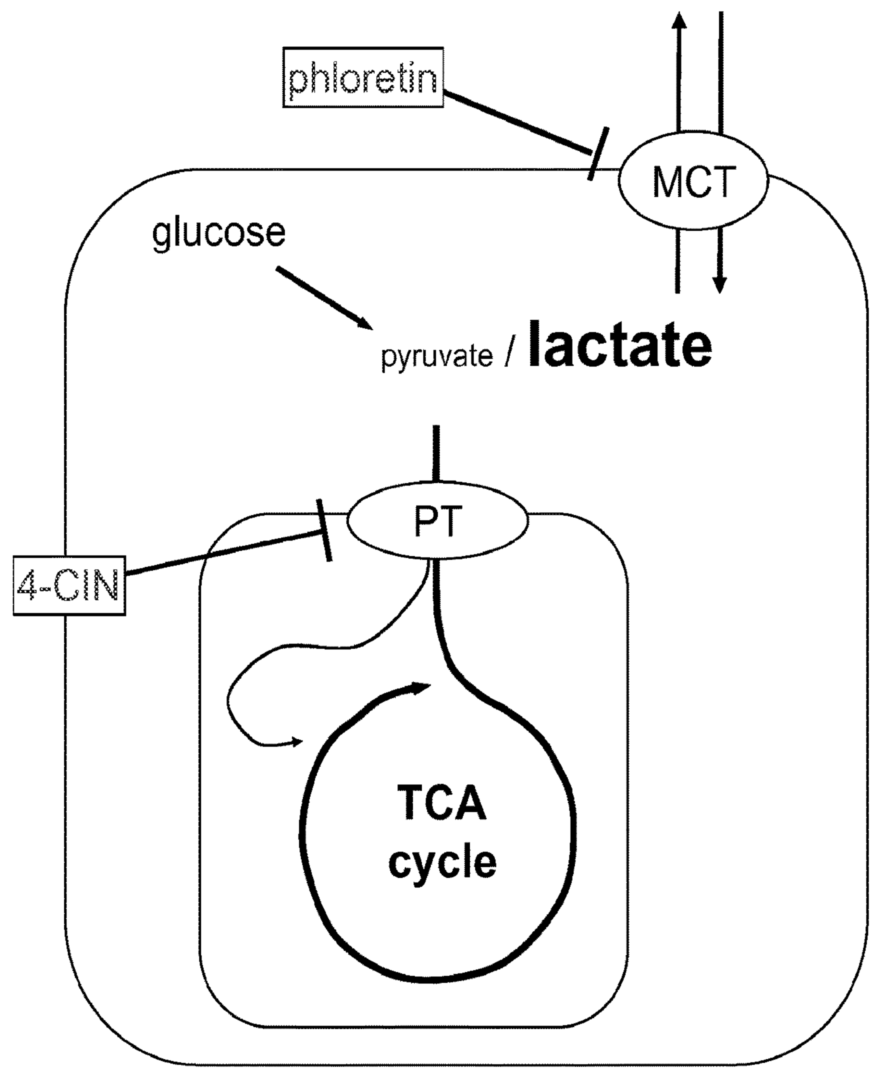
FIG. 14 depicts the main biochemical pathways for lactate in mammalian cells.

The diagram in FIG. 14 illustrates how the intracellular concentration of lactate is determined by the dynamic balance between pyruvate production by glycolysis, pyruvate consumption by mitochondria and lactate exchange through MCTs. In cells that are exporting lactate, perturbation of the steady state by addition of a blocker of the MCT is expected to cause lactate accumulation. In cells that are net lactate importers, an MCT-blocker is expected to cause depletion in intracellular lactate. In both cases, the rate of change will be equal to the rate of lactate production or consumption. As a demonstration of the principle in HEK293 cells and in astrocytes, MCT inhibition with phloretin (50 μM) caused the expected increase in intracellular lactate, indicative of lactate production (FIG. 15). Phloretin is also known to inhibit GLUT glucose transporters, however this should not compromise the analysis of astrocytes, neurons, or the cell lines so far characterized, which maintain resting intracellular glucose at levels well above the Km of hexokinase (Bittner et al., 2010; Takanaga et al., 2008; Fehr et al., 2003). In these cells, glucose consumption remains constant for several minutes in the presence of glucose transporter blockers like phloretin or cytochalasin B (Bittner et al., 2010). Thus, during the first few minutes of phloretin application, the rate of lactate accumulation is not diminished by lack of glucose supply. In muscle cells and adipocytes, which maintain low levels of intracellular glucose, a more selective MCT inhibitor may be used (Ovens et al., 2010).

Example 3

Method to Measure the Rate of Mitochondrial Metabolism with High Spatiotemporal Resolution Because the reaction catalyzed by LDH is relatively fast, the cytosolic pools of lactate and pyruvate are tightly linked, and variations in pyruvate are faithfully mimicked by lactate. Accordingly, perturbation of the steady-state by addition of a blocker of the mitochondrial pyruvate transporter (PT) will cause intracellular lactate accumulation at a rate equal to the rate of pyruvate consumption by mitochondria. As predicted by the kinetic model, inhibition of the mitochondrial pyruvate transporter in HEK293 cells with α-cyano-4-hydroxycinnamate (4-CIN) at a concentration that does not affect MCT function (Halestrap and Denton, 1975), led to an increase in intracellular lactate (FIG. 15). As typical of cell lines, HEK293 cells were more glycolytic than oxidative, having respective rates of lactate production and pyruvate uptake of 5.4 and 2.1 μM/s, whereas on average, astrocytes demonstrated a lactate production of 2 μM/s and pyruvate uptake of 7.6 μM/s (FIG. 15), consistent with their rate of glucose consumption of 2-6 μM/s (Bittner et al., 2010; Bittner et al., 2011).

To further validate methods 2 and 3, the blockers were applied sequentially and a mathematical model based on the kinetic model described in FIG. 14 was fitted to the data. The responses of intracellular lactate to transient inhibitions of the PT with 4-CIN (200 μM) and the MCTs with phloretin (50 μM) were measured in the same HEK293 cell in the presence of 25 mM glucose and no extracellular lactate. The straight lines represent the slopes of the lactate increases fitted by linear regression during the first minute (4-CIN) or during the whole exposure (phloretin). The red line represents the best fit of the kinetic model to the data, as described in Experimental Procedures, assuming full inhibition of the transporters. Fitted parameters were: G=10.3 μM/s, PT=4.8 μM/s, LDHf=9 s-1, LDHr=0.45 s-1, Vmax=186 μM/s, G-PT (lactate production)=5.5 μM/s. PT and lactate release rates respectively estimated from the initial slopes of lactate increase after transporter inhibition were over 90% of those estimated by modeling. As shown in FIG. 16, the rate of lactate accumulation induced by 4-CIN was maximal at the onset of inhibition and then declined, due to increased efflux through the MCT as lactate accumulated. Therefore, only the initial rate of lactate accumulation will represent mitochondrial metabolism accurately. In contrast, MCT blockage resulted in sustained accumulation of lactate, a finding that is consistent with the accepted notions that glycolytic pyruvate production and mitochondrial pyruvate consumption are not modulated by cytosolic pyruvate. On the other hand, the limited accumulation of lactate caused by 4-CIN confirms that 4-CIN did not block MCTs to a significant extent. The best fit of the model to the data showed that the initial slopes of the changes in lactate concentration triggered by the transport blockers underestimate the actual rates of mitochondrial pyruvate uptake and lactate production by less than 10%.

Example 4

Detection of Drugs that Interfere with Mitochondrial Metabolism with High Spatiotemporal Resolution The screening for unwanted effects is an important part of the process of drug discovery. One possibility to be ruled out before the drug is tested in animals or humans is the possibility that a candidate drug may exert undesirable effects on cellular energy metabolism. An inhibition of mitochondrial ATP production is compensated by increase in glycolytic ATP production and lactate production. Typically, a 3-4 fold increase in the rate of glucose consumption is observed (Bittner et al., 2010). However, the increase in lactate production can be much higher, because without the mitochondrial pyruvate sink, all glucose is now converted into lactate. Taking advantage of the improved resolution of the lactate sensor of the present invention, a method is presented that detects mitochondrial poisoning with very high sensitivity. As an example of this method, an acute inhibition of oxidative phosphorylation in astrocytes with 5 mM azide caused a 26±4-fold increase in the rate of lactate production measured with the lactate sensor of the present invention (FIG. 17*a*). FIG. 17*b* shows the acute effect of azide 5 mM on the intracellular concentration of lactate. Used in multi-well plate format, both protocols may be incorporated in high throughput applications for the screening of mitochondrial interference.

Example 5

Detection of the Warburg Effect in Single Cells with High Temporal Resolution Augmented flux through glycolysis and the pentose phosphate pathway in cancer cells provides the building blocks for proliferation and a high redox state that protects them against free radicals released during chemotherapy, while the lactic acid exported via MCTs acidifies the tumor environment and facilitates cell migration and metastasis. The glycolytic nature of cancer cells even in the presence of oxygen, a phenomenon known as the Warburg effect, is detected by comparing lactate production with oxygen consumption, measurements that demand large numbers of cells and overlook tissue heterogeneity. The reversible nature of mitochondrial flux and lactate production measurements with the lactate sensor allowed a more refined characterization of the Warburg phenotype. A comparison of astrocytes with T98G glioblastoma cells, showed that the non-transformed cells are more oxidative than their tumor counterparts (FIGS. 18 and 19). The difference between normal and cancerous cells was dramatically amplified by lactate production and pyruvate uptake, to give a parameter of cell metabolism that we have termed Warburg Index (WI). Some glioblastoma cells behaved almost like an astrocyte but some presented Warburg Index values that were 100 times higher than that of a normal astrocyte (FIG. 20). Tumors are known to be metabolically heterogeneous, which is expected given unequal access of their cells to oxygen and nutrients, but it seems remarkable that a cell line like T98G, cultured under carefully controlled conditions at high oxygen levels be also so heterogeneous from the metabolic point of view. The single-cell real-time capability of the lactate sensor should allow a metabolic characterization of individual cells and cell lineages in tumors and tissue explants. Used in cell populations with a multi-well plate reader, it is readily amenable for high throughput applications. An alternative embodiment of Example 5 replaces 4-CIN with an inhibitor of oxidative phosphorylation like azide or rotenone.

While certain embodiments of the invention have been described, other embodiments may exist. Further, any disclosed method steps or stages may be modified in any manner, including by reordering steps and/or inserting or deleting steps, without departing from the invention. While the specification includes a detailed description of the nanosensor and the associated drawings, the invention's scope is indicated by the following claims. Furthermore, while the specification has been described in a specific language, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

LIST OF REFERENCES

Brooks, G. A. J. Physiol 587, 5591-5600 (2009).
Barros, L. F. & Deitmer, J. W. Brain Res. Rev. 63, 149-159 (2010).
Ganapathy, V., Thangaraju, M., & Prasad, P. D. Pharmacol. Ther. 121, 29-40 (2009).
Vander Heiden, M. G., Cantley, L. C., & Thompson, C. B. Science. 324, 1029-1033 (2009).
Pellerin, L. et al. Glia. 55, 1251-1262 (2007).
Gao, Y. G. et al. Nucleic Acids Res. 36, 7110-7123 (2008).
Aguilera, L. et al. J. Bacteriol. 190, 2997-3005 (2008).
Deuschle, K. et al. Protein Sci. 14, 2304-2314 (2005).
Day, R. N., Booker, C. F., & Periasamy, A. J. Biomed. Opt. 13, 031203 (2008).
Nagai, T. et al. Nat. Biotechnol. 20, 87-90 (2002).
Bittner, C. X. et al. Front. Neuroenergetics 2, 1-11 doi: 10.3389/fnene.2010.00026 (2010).
Ovens, M. J. et al. Biochem. J. 425, 523-530 (2010).
Becker, H. M., Broer, S., & Deitmer, J. W. Biophys. J. 86, 235-247 (2004).
Halestrap, A. P. & Denton, R. M. Biochem. J. 148, 97-106 (1975).
Georgi, T., Engels, V., & Wendisch, V. F. J. Bacteriol. 190, 963-971 (2008).
Nagai T, Ibata K, Park E S, Kubota M, Mikoshiba K, Miyawaki A. Nat Biotechnol. 2002 January; 20(1):87-90.
Akerboom J, Rivera J D, Guilbe M M, Malave E C, Hernandez H H, Tian L, Hires S A, Marvin J S, Looger L L, Schreiter E R. J Biol Chem. 2009 Mar. 6; 284 (10):6455-64. Epub 2008 Dec. 18.

What is claimed is:

1. A method for the measurement of lactate transport wherein the method comprises the steps of:

a) expressing a FRET-based lactate nanosensor in a cytosol of a desired host selected from single cells or cell populations, adherent cells or cells in suspension, cells in a cell culture, a tissue culture, a mixed cell culture, a tissue explant, or cells in animal tissues in vivo, wherein the nanosensor comprises a bacterial LldR transcription factor between donor and acceptor fluorescent protein moieties, wherein the nanosensor remains in the cytosol;

b) calibrating the host with predetermined values of intracellular, extracellular, subcellular lactate concentrations, recording lactate concentrations in time;

c) disrupting the steady-state of lactate in the cell; and d) recording the output from the nanosensor calculating the lactate concentration at different time points and determining the rates of transport.

2. The method of claim 1, wherein in step b) the FRET-based lactate nanosensor in cells is calibrated by using the kinetic constants of the sensor obtained in vitro and a zero-lactate level determined in the presence of pyruvate.

3. The method of claim 2, wherein in step c) the disruption of lactate steady-state is by exposing cells to varying concentrations of extracellular lactate.

4. A method for the measurement of the rate of lactate production or consumption wherein the method comprises the steps of:

a) expressing a FRET-based lactate nanosensor in a cytosol of a desired host selected from single cells or cell populations, adherent cells or cells in suspension, cells in a cell culture, a tissue culture, a mixed cell culture, a tissue explant, or cells in animal tissues in vivo, wherein the nanosensor comprises a bacterial LldR transcription factor between donor and acceptor fluorescent protein moieties, wherein the nanosensor remains in the cytosol;

b) calibrating the host with predetermined values of intracellular, extracellular, subcellular lactate concentrations, recording lactate concentrations in time;

c) disrupting the steady-state of lactate in the cell;

d) recording the output from the nanosensor calculating the lactate concentration at different time points and determining the rates of lactate production or consumption.

5. The method of claim 4, wherein in step b) the FRET-based lactate nanosensor in cells is calibrated by using the kinetic constants of the sensor obtained in vitro and a zero-lactate level determined in the presence of pyruvate.

6. The method of claim 4, wherein in step c) the disruption of lactate steady-state is by adding an MCT inhibitor which measures the rates of lactate accumulation, equal to the rate of lactate production, or lactate depletion, equal to the rate of lactate consumption.

7. A method for the measurement of the rate of mitochondrial pyruvate consumption wherein the method comprises the steps of:

a) expressing a FRET-based lactate nanosensor in a cytosol of a desired host selected from single cells or cell populations, adherent cells or cells in suspension, cells in a cell culture, a tissue culture, a mixed cell culture, a tissue explant, or cells in animal tissues in vivo, wherein the nanosensor comprises a bacterial LldR transcription factor between donor and acceptor fluorescent protein moieties, wherein the nanosensor remains in the cytosol;

b) calibrating the host with predetermined values of intracellular, extracellular, subcellular lactate concentrations, recording lactate concentrations in time;

c) disrupting the steady-state of lactate in the cell;

d) recording the output from the nanosensor calculating the lactate concentration at different time points and determining the rates of mitochondrial pyruvate consumption.

8. The method of claim 7, wherein in step b) the FRET-based lactate nanosensor in cells is calibrated by using the kinetic constants of the sensor obtained in vitro and a zero-lactate level determined in the presence of pyruvate.

9. The method of claim 7, wherein in step c) the disruption of lactate steady-state is by adding a blocker of the mitochondrial pyruvate transporter and measures the initial rate of lactate accumulation, which is equal to the rate of pyruvate consumption by mitochondria.

10. A method for the quantification of the Warburg phenomenon wherein the method comprises the steps of:

a) expressing a FRET-based lactate nanosensor in a cytosol of a desired host selected from single cells or cell populations, adherent cells or cells in suspension, cells in a cell culture, a tissue culture, a mixed cell culture, a tissue explant, or cells in animal tissues in vivo, wherein the nanosensor comprises a bacterial LldR transcription factor between donor and acceptor fluorescent protein moieties, wherein the nanosensor remains in the cytosol;

b) calibrating the host with predetermined values of intracellular, extracellular, subcellular lactate concentrations, recording lactate concentrations in time;

c) disrupting the steady-state of lactate in the cell;

d) recording the output from the nanosensor calculating the lactate concentration at different time points and determining the rates of transport; and e) quantifying the Warburg phenomenon by calculating the ratio between the rate of lactate accumulation in the presence of an MCT inhibitor, and the rate of lactate accumulation in the presence of an inhibitor of the mitochondrial pyruvate transporter.

11. The method of claim 10, wherein in step b) the FRET-based lactate nanosensor in cells is calibrated by using the kinetic constants of the sensor obtained in vitro and a zero-lactate level determined in the presence of pyruvate.

12. The method of claim 10, wherein in step c) the disruption of lactate steady-state is by adding an MCT inhibitor which measures the rates of lactate production or lactate consumption and adding a blocker of the mitochondrial pyruvate transporter, the method further including measuring the initial rate of lactate accumulation, which is equal to the rate of pyruvate consumption by mitochondria.

13. The method of claim 1, wherein the nanosensor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

14. The method of claim 4, wherein the nanosensor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

15. The method of claim 7, wherein the nanosensor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

16. The method of claim 10, wherein the nanosensor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

* * * * *

SEQUENCE LISTING

```
<160> NUMBER OF SEQ ID NOS: 34

<210> SEQ ID NO 1
<211> LENGTH: 772
<212> TYPE: PRT
<213> ORGANISM: Artificial Sequence
<220> FEATURE:
<223> OTHER INFORMATION: Synthetic

<400> SEQUENCE: 1

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220
```

-continued

```
Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Met
                245                 250                 255

Ile Val Leu Pro Arg Arg Leu Ser Asp Glu Val Ala Asp Arg Val Arg
            260                 265                 270

Ala Leu Ile Asp Glu Lys Asn Leu Glu Ala Gly Met Lys Leu Pro Ala
        275                 280                 285

Glu Arg Gln Leu Ala Met Gln Leu Gly Val Ser Arg Asn Ser Leu Arg
    290                 295                 300

Glu Ala Leu Ala Lys Leu Val Ser Glu Gly Val Leu Leu Ser Arg Arg
305                 310                 315                 320

Gly Gly Gly Thr Phe Ile Arg Trp Arg His Asp Thr Trp Ser Glu Gln
                325                 330                 335

Asn Ile Val Gln Pro Leu Lys Thr Leu Met Ala Asp Asp Pro Asp Tyr
            340                 345                 350

Ser Phe Asp Ile Leu Glu Ala Arg Tyr Ala Ile Glu Ala Ser Thr Ala
        355                 360                 365

Trp His Ala Ala Met Arg Ala Thr Pro Gly Asp Lys Glu Lys Ile Gln
    370                 375                 380

Leu Cys Phe Glu Ala Thr Leu Ser Glu Asp Pro Asp Ile Ala Ser Gln
385                 390                 395                 400

Ala Asp Val Arg Phe His Leu Ala Ile Ala Glu Ala Ser His Asn Ile
                405                 410                 415

Val Leu Leu Gln Thr Met Arg Gly Phe Phe Asp Val Leu Gln Ser Ser
            420                 425                 430

Val Lys His Ser Arg Gln Arg Met Tyr Leu Val Pro Pro Val Phe Ser
        435                 440                 445

Gln Leu Thr Glu Gln His Gln Ala Val Ile Asp Ala Ile Phe Ala Gly
    450                 455                 460

Asp Ala Asp Gly Ala Arg Lys Ala Met Met Ala His Leu Ser Phe Val
465                 470                 475                 480

His Thr Thr Met Lys Arg Phe Asp Glu Asp Gln Ala Arg His Ala Arg
                485                 490                 495

Ile Thr Arg Leu Pro Gly Glu His Asn Glu His Ser Arg Glu Lys Asn
            500                 505                 510

Ala Leu Lys Lys Gly Glu Phe Asp Pro Ala Phe Leu Tyr Lys Val Val
        515                 520                 525

Leu Lys Arg Ser Thr Met Val Ser Lys Gly Glu Glu Leu Phe Thr Gly
    530                 535                 540

Val Val Pro Ile Leu Val Glu Leu Asp Gly Asp Val Asn Gly His Lys
545                 550                 555                 560

Phe Ser Val Ser Gly Glu Gly Glu Gly Asp Ala Thr Tyr Gly Lys Leu
                565                 570                 575

Thr Leu Lys Leu Ile Cys Thr Thr Gly Lys Leu Pro Val Pro Trp Pro
            580                 585                 590

Thr Leu Val Thr Thr Leu Gly Tyr Gly Leu Gln Cys Phe Ala Arg Tyr
        595                 600                 605

Pro Asp His Met Lys Gln His Asp Phe Phe Lys Ser Ala Met Pro Glu
    610                 615                 620

Gly Tyr Val Gln Glu Arg Thr Ile Phe Phe Lys Asp Asp Gly Asn Tyr
625                 630                 635                 640

Lys Thr Arg Ala Glu Val Lys Phe Glu Gly Asp Thr Leu Val Asn Arg
```

```
                645                 650                 655

Ile Glu Leu Lys Gly Ile Asp Phe Lys Glu Asp Gly Asn Ile Leu Gly
            660                 665                 670

His Lys Leu Glu Tyr Asn Tyr Asn Ser His Asn Val Tyr Ile Thr Ala
        675                 680                 685

Asp Lys Gln Lys Asn Gly Ile Lys Ala Asn Phe Lys Ile Arg His Asn
    690                 695                 700

Ile Glu Asp Gly Gly Val Gln Leu Ala Asp His Tyr Gln Gln Asn Thr
705                 710                 715                 720

Pro Ile Gly Asp Gly Pro Val Leu Leu Pro Asp Asn His Tyr Leu Ser
                725                 730                 735

Tyr Gln Ser Ala Leu Ser Lys Asp Pro Asn Glu Lys Arg Asp His Met
            740                 745                 750

Val Leu Leu Glu Phe Val Thr Ala Ala Gly Ile Thr Leu Gly Met Asp
        755                 760                 765

Glu Leu Tyr Lys
    770


<210> SEQ ID NO 2
<211> LENGTH: 745
<212> TYPE: PRT
<213> ORGANISM: Artificial Sequence
<220> FEATURE:
<223> OTHER INFORMATION: Synthetic

<400> SEQUENCE: 2

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
```

-continued

```
225                 230                 235                 240

Thr Ser Leu Tyr Lys Lys Ala Gly Ser Glu Phe Ala Leu Gly Thr Met
                245                 250                 255

Ser Val Lys Ala His Glu Ser Val Met Asp Trp Val Thr Glu Glu Leu
            260                 265                 270

Arg Ser Gly Arg Leu Lys Ile Gly Asp His Leu Pro Ser Glu Arg Ala
        275                 280                 285

Leu Ser Glu Thr Leu Gly Val Ser Arg Ser Ser Leu Arg Glu Ala Leu
    290                 295                 300

Arg Val Leu Glu Ala Leu Gly Thr Ile Ser Thr Ala Thr Gly Ser Gly
305                 310                 315                 320

Pro Arg Ser Gly Thr Ile Ile Thr Ala Ala Pro Gly Gln Ala Leu Ser
                325                 330                 335

Leu Ser Val Thr Leu Gln Leu Val Thr Asn Gln Val Gly His His Asp
            340                 345                 350

Ile Tyr Glu Thr Arg Gln Leu Leu Glu Gly Trp Ala Ala Leu His Ser
        355                 360                 365

Ser Ala Glu Arg Gly Asp Trp Asp Val Ala Glu Ala Leu Leu Glu Lys
    370                 375                 380

Met Asp Asp Pro Ser Leu Pro Leu Glu Asp Phe Leu Arg Phe Asp Ala
385                 390                 395                 400

Glu Phe His Val Val Ile Ser Lys Gly Ala Glu Asn Pro Leu Ile Ser
                405                 410                 415

Thr Leu Met Glu Ala Leu Arg Leu Ser Val Ala Asp His Thr Val Ala
            420                 425                 430

Arg Ala Arg Ala Leu Pro Asp Trp Arg Ala Thr Ser Ala Arg Leu Gln
        435                 440                 445

Lys Glu His Arg Ala Ile Leu Ala Ala Leu Arg Ala Gly Glu Ser Thr
    450                 455                 460

Val Ala Ala Thr Leu Ile Lys Glu His Ile Glu Gly Tyr Tyr Glu Glu
465                 470                 475                 480

Thr Ala Ala Ala Glu Ala Leu Lys Lys Gly Glu Phe Asp Pro Ala Phe
                485                 490                 495

Leu Tyr Lys Val Val Leu Lys Arg Ser Thr Met Val Ser Lys Gly Glu
            500                 505                 510

Glu Leu Phe Thr Gly Val Val Pro Ile Leu Val Glu Leu Asp Gly Asp
        515                 520                 525

Val Asn Gly His Lys Phe Ser Val Ser Gly Glu Gly Glu Gly Asp Ala
    530                 535                 540

Thr Tyr Gly Lys Leu Thr Leu Lys Leu Ile Cys Thr Thr Gly Lys Leu
545                 550                 555                 560

Pro Val Pro Trp Pro Thr Leu Val Thr Thr Leu Gly Tyr Gly Leu Gln
                565                 570                 575

Cys Phe Ala Arg Tyr Pro Asp His Met Lys Gln His Asp Phe Phe Lys
            580                 585                 590

Ser Ala Met Pro Glu Gly Tyr Val Gln Glu Arg Thr Ile Phe Phe Lys
        595                 600                 605

Asp Asp Gly Asn Tyr Lys Thr Arg Ala Glu Val Lys Phe Glu Gly Asp
    610                 615                 620

Thr Leu Val Asn Arg Ile Glu Leu Lys Gly Ile Asp Phe Lys Glu Asp
625                 630                 635                 640

Gly Asn Ile Leu Gly His Lys Leu Glu Tyr Asn Tyr Asn Ser His Asn
                645                 650                 655
```

```
Val Tyr Ile Thr Ala Asp Lys Gln Lys Asn Gly Ile Lys Ala Asn Phe
            660                 665                 670

Lys Ile Arg His Asn Ile Glu Asp Gly Gly Val Gln Leu Ala Asp His
        675                 680                 685

Tyr Gln Gln Asn Thr Pro Ile Gly Asp Gly Pro Val Leu Leu Pro Asp
    690                 695                 700

Asn His Tyr Leu Ser Tyr Gln Ser Ala Leu Ser Lys Asp Pro Asn Glu
705                 710                 715                 720

Lys Arg Asp His Met Val Leu Leu Glu Phe Val Thr Ala Ala Gly Ile
                725                 730                 735

Thr Leu Gly Met Asp Glu Leu Tyr Lys
            740                 745


<210> SEQ ID NO 3
<211> LENGTH: 757
<212> TYPE: PRT
<213> ORGANISM: Artificial Sequence
<220> FEATURE:
<223> OTHER INFORMATION: Synthetic

<400> SEQUENCE: 3

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ile Val Leu Pro Arg Arg Leu Ser Asp Glu Val Ala Asp Arg Val
                245                 250                 255

Arg Ala Leu Ile Asp Glu Lys Asn Leu Glu Ala Gly Met Lys Leu Pro
            260                 265                 270
```

-continued

```
Ala Glu Arg Gln Leu Ala Met Gln Leu Gly Val Ser Arg Asn Ser Leu
        275                 280                 285

Arg Glu Ala Leu Ala Lys Leu Val Ser Glu Gly Val Leu Leu Ser Arg
    290                 295                 300

Arg Gly Gly Gly Thr Phe Ile Arg Trp Arg His Asp Thr Trp Ser Glu
305                 310                 315                 320

Gln Asn Ile Val Gln Pro Leu Lys Thr Leu Met Ala Asp Asp Pro Asp
                325                 330                 335

Tyr Ser Phe Asp Ile Leu Glu Ala Arg Tyr Ala Ile Glu Ala Ser Thr
            340                 345                 350

Ala Trp His Ala Ala Met Arg Ala Thr Pro Gly Asp Lys Glu Lys Ile
        355                 360                 365

Gln Leu Cys Phe Glu Ala Thr Leu Ser Glu Asp Pro Asp Ile Ala Ser
    370                 375                 380

Gln Ala Asp Val Arg Phe His Leu Ala Ile Ala Glu Ala Ser His Asn
385                 390                 395                 400

Ile Val Leu Leu Gln Thr Met Arg Gly Phe Phe Asp Val Leu Gln Ser
                405                 410                 415

Ser Val Lys His Ser Arg Gln Arg Met Tyr Leu Val Pro Pro Val Phe
            420                 425                 430

Ser Gln Leu Thr Glu Gln His Gln Ala Val Ile Asp Ala Ile Phe Ala
        435                 440                 445

Gly Asp Ala Asp Gly Ala Arg Lys Ala Met Met Ala His Leu Ser Phe
    450                 455                 460

Val His Thr Thr Met Lys Arg Phe Asp Glu Asp Gln Ala Arg His Ala
465                 470                 475                 480

Arg Ile Thr Arg Leu Pro Gly Glu His Asn Glu His Ser Arg Glu Lys
                485                 490                 495

Asn Ala Leu Lys Lys Gly Glu Phe Asp Pro Ala Phe Leu Tyr Lys Val
            500                 505                 510

Val Leu Lys Arg Ser Thr Met Val Ser Lys Gly Glu Glu Leu Phe Thr
        515                 520                 525

Gly Val Val Pro Ile Leu Val Glu Leu Asp Gly Asp Val Asn Gly His
    530                 535                 540

Lys Phe Ser Val Ser Gly Glu Gly Glu Gly Asp Ala Thr Tyr Gly Lys
545                 550                 555                 560

Leu Thr Leu Lys Leu Ile Cys Thr Thr Gly Lys Leu Pro Val Pro Trp
                565                 570                 575

Pro Thr Leu Val Thr Thr Leu Gly Tyr Gly Leu Gln Cys Phe Ala Arg
            580                 585                 590

Tyr Pro Asp His Met Lys Gln His Asp Phe Phe Lys Ser Ala Met Pro
        595                 600                 605

Glu Gly Tyr Val Gln Glu Arg Thr Ile Phe Phe Lys Asp Asp Gly Asn
    610                 615                 620

Tyr Lys Thr Arg Ala Glu Val Lys Phe Glu Gly Asp Thr Leu Val Asn
625                 630                 635                 640

Arg Ile Glu Leu Lys Gly Ile Asp Phe Lys Glu Asp Gly Asn Ile Leu
                645                 650                 655

Gly His Lys Leu Glu Tyr Asn Tyr Asn Ser His Asn Val Tyr Ile Thr
            660                 665                 670

Ala Asp Lys Gln Lys Asn Gly Ile Lys Ala Asn Phe Lys Ile Arg His
        675                 680                 685
```

```
Asn Ile Glu Asp Gly Gly Val Gln Leu Ala Asp His Tyr Gln Gln Asn
    690                 695                 700

Thr Pro Ile Gly Asp Gly Pro Val Leu Leu Pro Asp Asn His Tyr Leu
705                 710                 715                 720

Ser Tyr Gln Ser Ala Leu Ser Lys Asp Pro Asn Glu Lys Arg Asp His
                725                 730                 735

Met Val Leu Leu Glu Phe Val Thr Ala Ala Gly Ile Thr Leu Gly Met
            740                 745                 750

Asp Glu Leu Tyr Lys
        755


<210> SEQ ID NO 4
<211> LENGTH: 730
<212> TYPE: PRT
<213> ORGANISM: Artificial Sequence
<220> FEATURE:
<223> OTHER INFORMATION: Synthetic

<400> SEQUENCE: 4

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ser Val Lys Ala His Glu Ser Val Met Asp Trp Val Thr Glu Glu
                245                 250                 255

Leu Arg Ser Gly Arg Leu Lys Ile Gly Asp His Leu Pro Ser Glu Arg
            260                 265                 270

Ala Leu Ser Glu Thr Leu Gly Val Ser Arg Ser Ser Leu Arg Glu Ala
        275                 280                 285
```

```
Leu Arg Val Leu Glu Ala Leu Gly Thr Ile Ser Thr Ala Thr Gly Ser
    290                 295                 300

Gly Pro Arg Ser Gly Thr Ile Ile Thr Ala Ala Pro Gly Gln Ala Leu
305                 310                 315                 320

Ser Leu Ser Val Thr Leu Gln Leu Val Thr Asn Gln Val Gly His His
                325                 330                 335

Asp Ile Tyr Glu Thr Arg Gln Leu Leu Glu Gly Trp Ala Ala Leu His
            340                 345                 350

Ser Ser Ala Glu Arg Gly Asp Trp Asp Val Ala Glu Ala Leu Leu Glu
        355                 360                 365

Lys Met Asp Asp Pro Ser Leu Pro Leu Glu Asp Phe Leu Arg Phe Asp
    370                 375                 380

Ala Glu Phe His Val Val Ile Ser Lys Gly Ala Glu Asn Pro Leu Ile
385                 390                 395                 400

Ser Thr Leu Met Glu Ala Leu Arg Leu Ser Val Ala Asp His Thr Val
                405                 410                 415

Ala Arg Ala Arg Ala Leu Pro Asp Trp Arg Ala Thr Ser Ala Arg Leu
            420                 425                 430

Gln Lys Glu His Arg Ala Ile Leu Ala Ala Leu Arg Ala Gly Glu Ser
        435                 440                 445

Thr Val Ala Ala Thr Leu Ile Lys Glu His Ile Glu Gly Tyr Tyr Glu
    450                 455                 460

Glu Thr Ala Ala Ala Glu Ala Leu Lys Lys Gly Glu Phe Asp Pro Ala
465                 470                 475                 480

Phe Leu Tyr Lys Val Val Leu Lys Arg Ser Thr Met Val Ser Lys Gly
                485                 490                 495

Glu Glu Leu Phe Thr Gly Val Val Pro Ile Leu Val Glu Leu Asp Gly
            500                 505                 510

Asp Val Asn Gly His Lys Phe Ser Val Ser Gly Glu Gly Glu Gly Asp
        515                 520                 525

Ala Thr Tyr Gly Lys Leu Thr Leu Lys Leu Ile Cys Thr Thr Gly Lys
    530                 535                 540

Leu Pro Val Pro Trp Pro Thr Leu Val Thr Thr Leu Gly Tyr Gly Leu
545                 550                 555                 560

Gln Cys Phe Ala Arg Tyr Pro Asp His Met Lys Gln His Asp Phe Phe
                565                 570                 575

Lys Ser Ala Met Pro Glu Gly Tyr Val Gln Glu Arg Thr Ile Phe Phe
            580                 585                 590

Lys Asp Asp Gly Asn Tyr Lys Thr Arg Ala Glu Val Lys Phe Glu Gly
        595                 600                 605

Asp Thr Leu Val Asn Arg Ile Glu Leu Lys Gly Ile Asp Phe Lys Glu
    610                 615                 620

Asp Gly Asn Ile Leu Gly His Lys Leu Glu Tyr Asn Tyr Asn Ser His
625                 630                 635                 640

Asn Val Tyr Ile Thr Ala Asp Lys Gln Lys Asn Gly Ile Lys Ala Asn
                645                 650                 655

Phe Lys Ile Arg His Asn Ile Glu Asp Gly Gly Val Gln Leu Ala Asp
            660                 665                 670

His Tyr Gln Gln Asn Thr Pro Ile Gly Asp Gly Pro Val Leu Leu Pro
        675                 680                 685

Asp Asn His Tyr Leu Ser Tyr Gln Ser Ala Leu Ser Lys Asp Pro Asn
    690                 695                 700

Glu Lys Arg Asp His Met Val Leu Leu Glu Phe Val Thr Ala Ala Gly
```

```
705                 710                 715                 720

Ile Thr Leu Gly Met Asp Glu Leu Tyr Lys
                725                 730


<210> SEQ ID NO 5
<211> LENGTH: 757
<212> TYPE: PRT
<213> ORGANISM: Artificial Sequence
<220> FEATURE:
<223> OTHER INFORMATION: Synthetic

<400> SEQUENCE: 5

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Met
                245                 250                 255

Ile Val Leu Pro Arg Arg Leu Ser Asp Glu Val Ala Asp Arg Val Arg
            260                 265                 270

Ala Leu Ile Asp Glu Lys Asn Leu Glu Ala Gly Met Lys Leu Pro Ala
        275                 280                 285

Glu Arg Gln Leu Ala Met Gln Leu Gly Val Ser Arg Asn Ser Leu Arg
    290                 295                 300

Glu Ala Leu Ala Lys Leu Val Ser Glu Gly Val Leu Leu Ser Arg Arg
305                 310                 315                 320

Gly Gly Gly Thr Phe Ile Arg Trp Arg His Asp Thr Trp Ser Glu Gln
                325                 330                 335

Asn Ile Val Gln Pro Leu Lys Thr Leu Met Ala Asp Asp Pro Asp Tyr
```

```
            340                 345                 350

Ser Phe Asp Ile Leu Glu Ala Arg Tyr Ala Ile Glu Ala Ser Thr Ala
        355                 360                 365

Trp His Ala Ala Met Arg Ala Thr Pro Gly Asp Lys Glu Lys Ile Gln
    370                 375                 380

Leu Cys Phe Glu Ala Thr Leu Ser Glu Asp Pro Asp Ile Ala Ser Gln
385                 390                 395                 400

Ala Asp Val Arg Phe His Leu Ala Ile Ala Glu Ala Ser His Asn Ile
                405                 410                 415

Val Leu Leu Gln Thr Met Arg Gly Phe Phe Asp Val Leu Gln Ser Ser
            420                 425                 430

Val Lys His Ser Arg Gln Arg Met Tyr Leu Val Pro Pro Val Phe Ser
        435                 440                 445

Gln Leu Thr Glu Gln His Gln Ala Val Ile Asp Ala Ile Phe Ala Gly
    450                 455                 460

Asp Ala Asp Gly Ala Arg Lys Ala Met Met Ala His Leu Ser Phe Val
465                 470                 475                 480

His Thr Thr Met Lys Arg Phe Asp Glu Asp Gln Ala Arg His Ala Arg
                485                 490                 495

Ile Thr Arg Leu Pro Gly Glu His Asn Glu His Ser Arg Glu Lys Asn
            500                 505                 510

Ala Leu Lys Arg Ser Thr Met Val Ser Lys Gly Glu Glu Leu Phe Thr
        515                 520                 525

Gly Val Val Pro Ile Leu Val Glu Leu Asp Gly Asp Val Asn Gly His
    530                 535                 540

Lys Phe Ser Val Ser Gly Glu Gly Glu Gly Asp Ala Thr Tyr Gly Lys
545                 550                 555                 560

Leu Thr Leu Lys Leu Ile Cys Thr Thr Gly Lys Leu Pro Val Pro Trp
                565                 570                 575

Pro Thr Leu Val Thr Thr Leu Gly Tyr Gly Leu Gln Cys Phe Ala Arg
            580                 585                 590

Tyr Pro Asp His Met Lys Gln His Asp Phe Phe Lys Ser Ala Met Pro
        595                 600                 605

Glu Gly Tyr Val Gln Glu Arg Thr Ile Phe Phe Lys Asp Asp Gly Asn
    610                 615                 620

Tyr Lys Thr Arg Ala Glu Val Lys Phe Glu Gly Asp Thr Leu Val Asn
625                 630                 635                 640

Arg Ile Glu Leu Lys Gly Ile Asp Phe Lys Glu Asp Gly Asn Ile Leu
                645                 650                 655

Gly His Lys Leu Glu Tyr Asn Tyr Asn Ser His Asn Val Tyr Ile Thr
            660                 665                 670

Ala Asp Lys Gln Lys Asn Gly Ile Lys Ala Asn Phe Lys Ile Arg His
        675                 680                 685

Asn Ile Glu Asp Gly Gly Val Gln Leu Ala Asp His Tyr Gln Gln Asn
    690                 695                 700

Thr Pro Ile Gly Asp Gly Pro Val Leu Leu Pro Asp Asn His Tyr Leu
705                 710                 715                 720

Ser Tyr Gln Ser Ala Leu Ser Lys Asp Pro Asn Glu Lys Arg Asp His
                725                 730                 735

Met Val Leu Leu Glu Phe Val Thr Ala Ala Gly Ile Thr Leu Gly Met
            740                 745                 750

Asp Glu Leu Tyr Lys
        755
```

<210> SEQ ID NO 6
<211> LENGTH: 730
<212> TYPE: PRT
<213> ORGANISM: Artificial Sequence
<220> FEATURE:
<223> OTHER INFORMATION: Synthetic

<400> SEQUENCE: 6

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Met
                245                 250                 255

Ser Val Lys Ala His Glu Ser Val Met Asp Trp Val Thr Glu Glu Leu
            260                 265                 270

Arg Ser Gly Arg Leu Lys Ile Gly Asp His Leu Pro Ser Glu Arg Ala
        275                 280                 285

Leu Ser Glu Thr Leu Gly Val Ser Arg Ser Ser Leu Arg Glu Ala Leu
    290                 295                 300

Arg Val Leu Glu Ala Leu Gly Thr Ile Ser Thr Ala Thr Gly Ser Gly
305                 310                 315                 320

Pro Arg Ser Gly Thr Ile Ile Thr Ala Ala Pro Gly Gln Ala Leu Ser
                325                 330                 335

Leu Ser Val Thr Leu Gln Leu Val Thr Asn Gln Val Gly His His Asp
            340                 345                 350

Ile Tyr Glu Thr Arg Gln Leu Leu Glu Gly Trp Ala Ala Leu His Ser
        355                 360                 365
```

```
Ser Ala Glu Arg Gly Asp Trp Asp Val Ala Glu Ala Leu Leu Glu Lys
    370                 375                 380

Met Asp Asp Pro Ser Leu Pro Leu Glu Asp Phe Leu Arg Phe Asp Ala
385                 390                 395                 400

Glu Phe His Val Val Ile Ser Lys Gly Ala Glu Asn Pro Leu Ile Ser
                405                 410                 415

Thr Leu Met Glu Ala Leu Arg Leu Ser Val Ala Asp His Thr Val Ala
            420                 425                 430

Arg Ala Arg Ala Leu Pro Asp Trp Arg Ala Thr Ser Ala Arg Leu Gln
        435                 440                 445

Lys Glu His Arg Ala Ile Leu Ala Ala Leu Arg Ala Gly Glu Ser Thr
    450                 455                 460

Val Ala Ala Thr Leu Ile Lys Glu His Ile Glu Gly Tyr Tyr Glu Glu
465                 470                 475                 480

Thr Ala Ala Ala Glu Ala Leu Lys Arg Ser Thr Met Val Ser Lys Gly
                485                 490                 495

Glu Glu Leu Phe Thr Gly Val Val Pro Ile Leu Val Glu Leu Asp Gly
            500                 505                 510

Asp Val Asn Gly His Lys Phe Ser Val Ser Gly Glu Gly Glu Gly Asp
        515                 520                 525

Ala Thr Tyr Gly Lys Leu Thr Leu Lys Leu Ile Cys Thr Thr Gly Lys
    530                 535                 540

Leu Pro Val Pro Trp Pro Thr Leu Val Thr Thr Leu Gly Tyr Gly Leu
545                 550                 555                 560

Gln Cys Phe Ala Arg Tyr Pro Asp His Met Lys Gln His Asp Phe Phe
                565                 570                 575

Lys Ser Ala Met Pro Glu Gly Tyr Val Gln Glu Arg Thr Ile Phe Phe
            580                 585                 590

Lys Asp Asp Gly Asn Tyr Lys Thr Arg Ala Glu Val Lys Phe Glu Gly
        595                 600                 605

Asp Thr Leu Val Asn Arg Ile Glu Leu Lys Gly Ile Asp Phe Lys Glu
    610                 615                 620

Asp Gly Asn Ile Leu Gly His Lys Leu Glu Tyr Asn Tyr Asn Ser His
625                 630                 635                 640

Asn Val Tyr Ile Thr Ala Asp Lys Gln Lys Asn Gly Ile Lys Ala Asn
                645                 650                 655

Phe Lys Ile Arg His Asn Ile Glu Asp Gly Gly Val Gln Leu Ala Asp
            660                 665                 670

His Tyr Gln Gln Asn Thr Pro Ile Gly Asp Gly Pro Val Leu Leu Pro
        675                 680                 685

Asp Asn His Tyr Leu Ser Tyr Gln Ser Ala Leu Ser Lys Asp Pro Asn
    690                 695                 700

Glu Lys Arg Asp His Met Val Leu Leu Glu Phe Val Thr Ala Ala Gly
705                 710                 715                 720

Ile Thr Leu Gly Met Asp Glu Leu Tyr Lys
                725                 730
```

<210> SEQ ID NO 7
<211> LENGTH: 742
<212> TYPE: PRT
<213> ORGANISM: Artificial Sequence
<220> FEATURE:
<223> OTHER INFORMATION: Synthetic

<400> SEQUENCE: 7

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ile Val Leu Pro Arg Arg Leu Ser Asp Glu Val Ala Asp Arg Val
                245                 250                 255

Arg Ala Leu Ile Asp Glu Lys Asn Leu Glu Ala Gly Met Lys Leu Pro
            260                 265                 270

Ala Glu Arg Gln Leu Ala Met Gln Leu Gly Val Ser Arg Asn Ser Leu
        275                 280                 285

Arg Glu Ala Leu Ala Lys Leu Val Ser Glu Gly Val Leu Leu Ser Arg
    290                 295                 300

Arg Gly Gly Gly Thr Phe Ile Arg Trp Arg His Asp Thr Trp Ser Glu
305                 310                 315                 320

Gln Asn Ile Val Gln Pro Leu Lys Thr Leu Met Ala Asp Asp Pro Asp
                325                 330                 335

Tyr Ser Phe Asp Ile Leu Glu Ala Arg Tyr Ala Ile Glu Ala Ser Thr
            340                 345                 350

Ala Trp His Ala Ala Met Arg Ala Thr Pro Gly Asp Lys Glu Lys Ile
        355                 360                 365

Gln Leu Cys Phe Glu Ala Thr Leu Ser Glu Asp Pro Asp Ile Ala Ser
    370                 375                 380

Gln Ala Asp Val Arg Phe His Leu Ala Ile Ala Glu Ala Ser His Asn
385                 390                 395                 400

Ile Val Leu Leu Gln Thr Met Arg Gly Phe Phe Asp Val Leu Gln Ser
                405                 410                 415
```

```
Ser Val Lys His Ser Arg Gln Arg Met Tyr Leu Val Pro Pro Val Phe
            420                 425                 430

Ser Gln Leu Thr Glu Gln His Gln Ala Val Ile Asp Ala Ile Phe Ala
        435                 440                 445

Gly Asp Ala Asp Gly Ala Arg Lys Ala Met Met Ala His Leu Ser Phe
    450                 455                 460

Val His Thr Thr Met Lys Arg Phe Asp Glu Asp Gln Ala Arg His Ala
465                 470                 475                 480

Arg Ile Thr Arg Leu Pro Gly Glu His Asn Glu His Ser Arg Glu Lys
                485                 490                 495

Asn Ala Leu Lys Arg Ser Thr Met Val Ser Lys Gly Glu Glu Leu Phe
            500                 505                 510

Thr Gly Val Val Pro Ile Leu Val Glu Leu Asp Gly Asp Val Asn Gly
        515                 520                 525

His Lys Phe Ser Val Ser Gly Glu Gly Glu Gly Asp Ala Thr Tyr Gly
    530                 535                 540

Lys Leu Thr Leu Lys Leu Ile Cys Thr Thr Gly Lys Leu Pro Val Pro
545                 550                 555                 560

Trp Pro Thr Leu Val Thr Thr Leu Gly Tyr Gly Leu Gln Cys Phe Ala
                565                 570                 575

Arg Tyr Pro Asp His Met Lys Gln His Asp Phe Phe Lys Ser Ala Met
            580                 585                 590

Pro Glu Gly Tyr Val Gln Glu Arg Thr Ile Phe Phe Lys Asp Asp Gly
        595                 600                 605

Asn Tyr Lys Thr Arg Ala Glu Val Lys Phe Glu Gly Asp Thr Leu Val
    610                 615                 620

Asn Arg Ile Glu Leu Lys Gly Ile Asp Phe Lys Glu Asp Gly Asn Ile
625                 630                 635                 640

Leu Gly His Lys Leu Glu Tyr Asn Tyr Asn Ser His Asn Val Tyr Ile
                645                 650                 655

Thr Ala Asp Lys Gln Lys Asn Gly Ile Lys Ala Asn Phe Lys Ile Arg
            660                 665                 670

His Asn Ile Glu Asp Gly Gly Val Gln Leu Ala Asp His Tyr Gln Gln
        675                 680                 685

Asn Thr Pro Ile Gly Asp Gly Pro Val Leu Leu Pro Asp Asn His Tyr
    690                 695                 700

Leu Ser Tyr Gln Ser Ala Leu Ser Lys Asp Pro Asn Glu Lys Arg Asp
705                 710                 715                 720

His Met Val Leu Leu Glu Phe Val Thr Ala Ala Gly Ile Thr Leu Gly
                725                 730                 735

Met Asp Glu Leu Tyr Lys
            740
```

<210> SEQ ID NO 8
<211> LENGTH: 715
<212> TYPE: PRT
<213> ORGANISM: Artificial Sequence
<220> FEATURE:
<223> OTHER INFORMATION: Synthetic

<400> SEQUENCE: 8

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30
```

```
Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Met Ser Val Lys Ala His Glu Ser Val Met Asp Trp Val Thr Glu Glu
                245                 250                 255

Leu Arg Ser Gly Arg Leu Lys Ile Gly Asp His Leu Pro Ser Glu Arg
            260                 265                 270

Ala Leu Ser Glu Thr Leu Gly Val Ser Arg Ser Ser Leu Arg Glu Ala
        275                 280                 285

Leu Arg Val Leu Glu Ala Leu Gly Thr Ile Ser Thr Ala Thr Gly Ser
    290                 295                 300

Gly Pro Arg Ser Gly Thr Ile Ile Thr Ala Ala Pro Gly Gln Ala Leu
305                 310                 315                 320

Ser Leu Ser Val Thr Leu Gln Leu Val Thr Asn Gln Val Gly His His
                325                 330                 335

Asp Ile Tyr Glu Thr Arg Gln Leu Leu Glu Gly Trp Ala Ala Leu His
            340                 345                 350

Ser Ser Ala Glu Arg Gly Asp Trp Asp Val Ala Glu Ala Leu Leu Glu
        355                 360                 365

Lys Met Asp Asp Pro Ser Leu Pro Leu Glu Asp Phe Leu Arg Phe Asp
    370                 375                 380

Ala Glu Phe His Val Val Ile Ser Lys Gly Ala Glu Asn Pro Leu Ile
385                 390                 395                 400

Ser Thr Leu Met Glu Ala Leu Arg Leu Ser Val Ala Asp His Thr Val
                405                 410                 415

Ala Arg Ala Arg Ala Leu Pro Asp Trp Arg Ala Thr Ser Ala Arg Leu
            420                 425                 430

Gln Lys Glu His Arg Ala Ile Leu Ala Ala Leu Arg Ala Gly Glu Ser
        435                 440                 445

Thr Val Ala Ala Thr Leu Ile Lys Glu His Ile Glu Gly Tyr Tyr Glu
```

```
    450                 455                 460

Glu Thr Ala Ala Ala Glu Ala Leu Lys Arg Ser Thr Met Val Ser Lys
465                 470                 475                 480

Gly Glu Glu Leu Phe Thr Gly Val Val Pro Ile Leu Val Glu Leu Asp
                485                 490                 495

Gly Asp Val Asn Gly His Lys Phe Ser Val Ser Gly Glu Gly Glu Gly
            500                 505                 510

Asp Ala Thr Tyr Gly Lys Leu Thr Leu Lys Leu Ile Cys Thr Thr Gly
        515                 520                 525

Lys Leu Pro Val Pro Trp Pro Thr Leu Val Thr Thr Leu Gly Tyr Gly
    530                 535                 540

Leu Gln Cys Phe Ala Arg Tyr Pro Asp His Met Lys Gln His Asp Phe
545                 550                 555                 560

Phe Lys Ser Ala Met Pro Glu Gly Tyr Val Gln Glu Arg Thr Ile Phe
                565                 570                 575

Phe Lys Asp Asp Gly Asn Tyr Lys Thr Arg Ala Glu Val Lys Phe Glu
            580                 585                 590

Gly Asp Thr Leu Val Asn Arg Ile Glu Leu Lys Gly Ile Asp Phe Lys
        595                 600                 605

Glu Asp Gly Asn Ile Leu Gly His Lys Leu Glu Tyr Asn Tyr Asn Ser
    610                 615                 620

His Asn Val Tyr Ile Thr Ala Asp Lys Gln Lys Asn Gly Ile Lys Ala
625                 630                 635                 640

Asn Phe Lys Ile Arg His Asn Ile Glu Asp Gly Gly Val Gln Leu Ala
                645                 650                 655

Asp His Tyr Gln Gln Asn Thr Pro Ile Gly Asp Gly Pro Val Leu Leu
            660                 665                 670

Pro Asp Asn His Tyr Leu Ser Tyr Gln Ser Ala Leu Ser Lys Asp Pro
        675                 680                 685

Asn Glu Lys Arg Asp His Met Val Leu Leu Glu Phe Val Thr Ala Ala
    690                 695                 700

Gly Ile Thr Leu Gly Met Asp Glu Leu Tyr Lys
705                 710                 715


<210> SEQ ID NO 9
<211> LENGTH: 693
<212> TYPE: PRT
<213> ORGANISM: Artificial Sequence
<220> FEATURE:
<223> OTHER INFORMATION: Synthetic

<400> SEQUENCE: 9

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
```

-continued

```
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Glu
                245                 250                 255

Gln Asn Ile Val Gln Pro Leu Lys Thr Leu Met Ala Asp Asp Pro Asp
            260                 265                 270

Tyr Ser Phe Asp Ile Leu Glu Ala Arg Tyr Ala Ile Glu Ala Ser Thr
        275                 280                 285

Ala Trp His Ala Ala Met Arg Ala Thr Pro Gly Asp Lys Glu Lys Ile
    290                 295                 300

Gln Leu Cys Phe Glu Ala Thr Leu Ser Glu Asp Pro Asp Ile Ala Ser
305                 310                 315                 320

Gln Ala Asp Val Arg Phe His Leu Ala Ile Ala Glu Ala Ser His Asn
                325                 330                 335

Ile Val Leu Leu Gln Thr Met Arg Gly Phe Phe Asp Val Leu Gln Ser
            340                 345                 350

Ser Val Lys His Ser Arg Gln Arg Met Tyr Leu Val Pro Pro Val Phe
        355                 360                 365

Ser Gln Leu Thr Glu Gln His Gln Ala Val Ile Asp Ala Ile Phe Ala
    370                 375                 380

Gly Asp Ala Asp Gly Ala Arg Lys Ala Met Met Ala His Leu Ser Phe
385                 390                 395                 400

Val His Thr Thr Met Lys Arg Phe Asp Glu Asp Gln Ala Arg His Ala
                405                 410                 415

Arg Ile Thr Arg Leu Pro Gly Glu His Asn Glu His Ser Arg Glu Lys
            420                 425                 430

Asn Ala Leu Lys Lys Gly Glu Phe Asp Pro Ala Phe Leu Tyr Lys Val
        435                 440                 445

Val Leu Lys Arg Ser Thr Met Val Ser Lys Gly Glu Glu Leu Phe Thr
    450                 455                 460

Gly Val Val Pro Ile Leu Val Glu Leu Asp Gly Asp Val Asn Gly His
465                 470                 475                 480

Lys Phe Ser Val Ser Gly Glu Gly Glu Gly Asp Ala Thr Tyr Gly Lys
                485                 490                 495

Leu Thr Leu Lys Leu Ile Cys Thr Thr Gly Lys Leu Pro Val Pro Trp
            500                 505                 510

Pro Thr Leu Val Thr Thr Leu Gly Tyr Gly Leu Gln Cys Phe Ala Arg
        515                 520                 525
```

```
Tyr Pro Asp His Met Lys Gln His Asp Phe Phe Lys Ser Ala Met Pro
    530                 535                 540

Glu Gly Tyr Val Gln Glu Arg Thr Ile Phe Phe Lys Asp Asp Gly Asn
545                 550                 555                 560

Tyr Lys Thr Arg Ala Glu Val Lys Phe Glu Gly Asp Thr Leu Val Asn
                565                 570                 575

Arg Ile Glu Leu Lys Gly Ile Asp Phe Lys Glu Asp Gly Asn Ile Leu
            580                 585                 590

Gly His Lys Leu Glu Tyr Asn Tyr Asn Ser His Asn Val Tyr Ile Thr
        595                 600                 605

Ala Asp Lys Gln Lys Asn Gly Ile Lys Ala Asn Phe Lys Ile Arg His
    610                 615                 620

Asn Ile Glu Asp Gly Gly Val Gln Leu Ala Asp His Tyr Gln Gln Asn
625                 630                 635                 640

Thr Pro Ile Gly Asp Gly Pro Val Leu Leu Pro Asp Asn His Tyr Leu
                645                 650                 655

Ser Tyr Gln Ser Ala Leu Ser Lys Asp Pro Asn Glu Lys Arg Asp His
            660                 665                 670

Met Val Leu Leu Glu Phe Val Thr Ala Ala Gly Ile Thr Leu Gly Met
        675                 680                 685

Asp Glu Leu Tyr Lys
    690


<210> SEQ ID NO 10
<211> LENGTH: 669
<212> TYPE: PRT
<213> ORGANISM: Artificial Sequence
<220> FEATURE:
<223> OTHER INFORMATION: Synthetic

<400> SEQUENCE: 10

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190
```

```
Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Gly
                245                 250                 255

Gln Ala Leu Ser Leu Ser Val Thr Leu Gln Leu Val Thr Asn Gln Val
            260                 265                 270

Gly His His Asp Ile Tyr Glu Thr Arg Gln Leu Leu Glu Gly Trp Ala
        275                 280                 285

Ala Leu His Ser Ser Ala Glu Arg Gly Asp Trp Asp Val Ala Glu Ala
    290                 295                 300

Leu Leu Glu Lys Met Asp Asp Pro Ser Leu Pro Leu Glu Asp Phe Leu
305                 310                 315                 320

Arg Phe Asp Ala Glu Phe His Val Val Ile Ser Lys Gly Ala Glu Asn
                325                 330                 335

Pro Leu Ile Ser Thr Leu Met Glu Ala Leu Arg Leu Ser Val Ala Asp
            340                 345                 350

His Thr Val Ala Arg Ala Arg Ala Leu Pro Asp Trp Arg Ala Thr Ser
        355                 360                 365

Ala Arg Leu Gln Lys Glu His Arg Ala Ile Leu Ala Ala Leu Arg Ala
    370                 375                 380

Gly Glu Ser Thr Val Ala Ala Thr Leu Ile Lys Glu His Ile Glu Gly
385                 390                 395                 400

Tyr Tyr Glu Glu Thr Ala Ala Ala Glu Ala Leu Lys Lys Gly Glu Phe
                405                 410                 415

Asp Pro Ala Phe Leu Tyr Lys Val Val Leu Lys Arg Ser Thr Met Val
            420                 425                 430

Ser Lys Gly Glu Glu Leu Phe Thr Gly Val Val Pro Ile Leu Val Glu
        435                 440                 445

Leu Asp Gly Asp Val Asn Gly His Lys Phe Ser Val Ser Gly Glu Gly
    450                 455                 460

Glu Gly Asp Ala Thr Tyr Gly Lys Leu Thr Leu Lys Leu Ile Cys Thr
465                 470                 475                 480

Thr Gly Lys Leu Pro Val Pro Trp Pro Thr Leu Val Thr Thr Leu Gly
                485                 490                 495

Tyr Gly Leu Gln Cys Phe Ala Arg Tyr Pro Asp His Met Lys Gln His
            500                 505                 510

Asp Phe Phe Lys Ser Ala Met Pro Glu Gly Tyr Val Gln Glu Arg Thr
        515                 520                 525

Ile Phe Phe Lys Asp Asp Gly Asn Tyr Lys Thr Arg Ala Glu Val Lys
    530                 535                 540

Phe Glu Gly Asp Thr Leu Val Asn Arg Ile Glu Leu Lys Gly Ile Asp
545                 550                 555                 560

Phe Lys Glu Asp Gly Asn Ile Leu Gly His Lys Leu Glu Tyr Asn Tyr
                565                 570                 575

Asn Ser His Asn Val Tyr Ile Thr Ala Asp Lys Gln Lys Asn Gly Ile
            580                 585                 590

Lys Ala Asn Phe Lys Ile Arg His Asn Ile Glu Asp Gly Gly Val Gln
        595                 600                 605
```

```
Leu Ala Asp His Tyr Gln Gln Asn Thr Pro Ile Gly Asp Gly Pro Val
    610                 615                 620

Leu Leu Pro Asp Asn His Tyr Leu Ser Tyr Gln Ser Ala Leu Ser Lys
625                 630                 635                 640

Asp Pro Asn Glu Lys Arg Asp His Met Val Leu Leu Glu Phe Val Thr
                645                 650                 655

Ala Ala Gly Ile Thr Leu Gly Met Asp Glu Leu Tyr Lys
            660                 665


<210> SEQ ID NO 11
<211> LENGTH: 678
<212> TYPE: PRT
<213> ORGANISM: Artificial Sequence
<220> FEATURE:
<223> OTHER INFORMATION: Synthetic

<400> SEQUENCE: 11

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Glu Gln Asn Ile Val Gln Pro Leu Lys Thr Leu Met Ala Asp Asp Pro
                245                 250                 255

Asp Tyr Ser Phe Asp Ile Leu Glu Ala Arg Tyr Ala Ile Glu Ala Ser
            260                 265                 270

Thr Ala Trp His Ala Ala Met Arg Ala Thr Pro Gly Asp Lys Glu Lys
        275                 280                 285

Ile Gln Leu Cys Phe Glu Ala Thr Leu Ser Glu Asp Pro Asp Ile Ala
    290                 295                 300
```

```
Ser Gln Ala Asp Val Arg Phe His Leu Ala Ile Ala Glu Ala Ser His
305                 310                 315                 320

Asn Ile Val Leu Leu Gln Thr Met Arg Gly Phe Phe Asp Val Leu Gln
                325                 330                 335

Ser Ser Val Lys His Ser Arg Gln Arg Met Tyr Leu Val Pro Pro Val
            340                 345                 350

Phe Ser Gln Leu Thr Glu Gln His Gln Ala Val Ile Asp Ala Ile Phe
        355                 360                 365

Ala Gly Asp Ala Asp Gly Ala Arg Lys Ala Met Met Ala His Leu Ser
    370                 375                 380

Phe Val His Thr Thr Met Lys Arg Phe Asp Glu Asp Gln Ala Arg His
385                 390                 395                 400

Ala Arg Ile Thr Arg Leu Pro Gly Glu His Asn Glu His Ser Arg Glu
                405                 410                 415

Lys Asn Ala Leu Lys Lys Gly Glu Phe Asp Pro Ala Phe Leu Tyr Lys
            420                 425                 430

Val Val Leu Lys Arg Ser Thr Met Val Ser Lys Gly Glu Glu Leu Phe
        435                 440                 445

Thr Gly Val Val Pro Ile Leu Val Glu Leu Asp Gly Asp Val Asn Gly
    450                 455                 460

His Lys Phe Ser Val Ser Gly Glu Gly Glu Gly Asp Ala Thr Tyr Gly
465                 470                 475                 480

Lys Leu Thr Leu Lys Leu Ile Cys Thr Thr Gly Lys Leu Pro Val Pro
                485                 490                 495

Trp Pro Thr Leu Val Thr Thr Leu Gly Tyr Gly Leu Gln Cys Phe Ala
            500                 505                 510

Arg Tyr Pro Asp His Met Lys Gln His Asp Phe Phe Lys Ser Ala Met
        515                 520                 525

Pro Glu Gly Tyr Val Gln Glu Arg Thr Ile Phe Phe Lys Asp Asp Gly
    530                 535                 540

Asn Tyr Lys Thr Arg Ala Glu Val Lys Phe Glu Gly Asp Thr Leu Val
545                 550                 555                 560

Asn Arg Ile Glu Leu Lys Gly Ile Asp Phe Lys Glu Asp Gly Asn Ile
                565                 570                 575

Leu Gly His Lys Leu Glu Tyr Asn Tyr Asn Ser His Asn Val Tyr Ile
            580                 585                 590

Thr Ala Asp Lys Gln Lys Asn Gly Ile Lys Ala Asn Phe Lys Ile Arg
        595                 600                 605

His Asn Ile Glu Asp Gly Gly Val Gln Leu Ala Asp His Tyr Gln Gln
    610                 615                 620

Asn Thr Pro Ile Gly Asp Gly Pro Val Leu Leu Pro Asp Asn His Tyr
625                 630                 635                 640

Leu Ser Tyr Gln Ser Ala Leu Ser Lys Asp Pro Asn Glu Lys Arg Asp
                645                 650                 655

His Met Val Leu Leu Glu Phe Val Thr Ala Ala Gly Ile Thr Leu Gly
            660                 665                 670

Met Asp Glu Leu Tyr Lys
        675


<210> SEQ ID NO 12
<211> LENGTH: 654
<212> TYPE: PRT
<213> ORGANISM: Artificial Sequence
<220> FEATURE:
<223> OTHER INFORMATION: Synthetic
```

<400> SEQUENCE: 12

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Gly Gln Ala Leu Ser Leu Ser Val Thr Leu Gln Leu Val Thr Asn Gln
                245                 250                 255

Val Gly His His Asp Ile Tyr Glu Thr Arg Gln Leu Leu Glu Gly Trp
            260                 265                 270

Ala Ala Leu His Ser Ser Ala Glu Arg Gly Asp Trp Asp Val Ala Glu
        275                 280                 285

Ala Leu Leu Glu Lys Met Asp Asp Pro Ser Leu Pro Leu Glu Asp Phe
    290                 295                 300

Leu Arg Phe Asp Ala Glu Phe His Val Val Ile Ser Lys Gly Ala Glu
305                 310                 315                 320

Asn Pro Leu Ile Ser Thr Leu Met Glu Ala Leu Arg Leu Ser Val Ala
                325                 330                 335

Asp His Thr Val Ala Arg Ala Arg Ala Leu Pro Asp Trp Arg Ala Thr
            340                 345                 350

Ser Ala Arg Leu Gln Lys Glu His Arg Ala Ile Leu Ala Ala Leu Arg
        355                 360                 365

Ala Gly Glu Ser Thr Val Ala Ala Thr Leu Ile Lys Glu His Ile Glu
    370                 375                 380

Gly Tyr Tyr Glu Glu Thr Ala Ala Ala Glu Ala Leu Lys Lys Gly Glu
385                 390                 395                 400

Phe Asp Pro Ala Phe Leu Tyr Lys Val Val Leu Lys Arg Ser Thr Met
```

```
                405                 410                 415

Val Ser Lys Gly Glu Glu Leu Phe Thr Gly Val Val Pro Ile Leu Val
            420                 425                 430

Glu Leu Asp Gly Asp Val Asn Gly His Lys Phe Ser Val Ser Gly Glu
        435                 440                 445

Gly Glu Gly Asp Ala Thr Tyr Gly Lys Leu Thr Leu Lys Leu Ile Cys
    450                 455                 460

Thr Thr Gly Lys Leu Pro Val Pro Trp Pro Thr Leu Val Thr Thr Leu
465                 470                 475                 480

Gly Tyr Gly Leu Gln Cys Phe Ala Arg Tyr Pro Asp His Met Lys Gln
                485                 490                 495

His Asp Phe Phe Lys Ser Ala Met Pro Glu Gly Tyr Val Gln Glu Arg
            500                 505                 510

Thr Ile Phe Phe Lys Asp Asp Gly Asn Tyr Lys Thr Arg Ala Glu Val
        515                 520                 525

Lys Phe Glu Gly Asp Thr Leu Val Asn Arg Ile Glu Leu Lys Gly Ile
    530                 535                 540

Asp Phe Lys Glu Asp Gly Asn Ile Leu Gly His Lys Leu Glu Tyr Asn
545                 550                 555                 560

Tyr Asn Ser His Asn Val Tyr Ile Thr Ala Asp Lys Gln Lys Asn Gly
                565                 570                 575

Ile Lys Ala Asn Phe Lys Ile Arg His Asn Ile Glu Asp Gly Gly Val
            580                 585                 590

Gln Leu Ala Asp His Tyr Gln Gln Asn Thr Pro Ile Gly Asp Gly Pro
        595                 600                 605

Val Leu Leu Pro Asp Asn His Tyr Leu Ser Tyr Gln Ser Ala Leu Ser
    610                 615                 620

Lys Asp Pro Asn Glu Lys Arg Asp His Met Val Leu Leu Glu Phe Val
625                 630                 635                 640

Thr Ala Ala Gly Ile Thr Leu Gly Met Asp Glu Leu Tyr Lys
                645                 650


<210> SEQ ID NO 13
<211> LENGTH: 678
<212> TYPE: PRT
<213> ORGANISM: Artificial Sequence
<220> FEATURE:
<223> OTHER INFORMATION: Synthetic

<400> SEQUENCE: 13

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
```

-continued

```
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Glu
                245                 250                 255

Gln Asn Ile Val Gln Pro Leu Lys Thr Leu Met Ala Asp Asp Pro Asp
            260                 265                 270

Tyr Ser Phe Asp Ile Leu Glu Ala Arg Tyr Ala Ile Glu Ala Ser Thr
        275                 280                 285

Ala Trp His Ala Ala Met Arg Ala Thr Pro Gly Asp Lys Glu Lys Ile
    290                 295                 300

Gln Leu Cys Phe Glu Ala Thr Leu Ser Glu Asp Pro Asp Ile Ala Ser
305                 310                 315                 320

Gln Ala Asp Val Arg Phe His Leu Ala Ile Ala Glu Ala Ser His Asn
                325                 330                 335

Ile Val Leu Leu Gln Thr Met Arg Gly Phe Phe Asp Val Leu Gln Ser
            340                 345                 350

Ser Val Lys His Ser Arg Gln Arg Met Tyr Leu Val Pro Pro Val Phe
        355                 360                 365

Ser Gln Leu Thr Glu Gln His Gln Ala Val Ile Asp Ala Ile Phe Ala
    370                 375                 380

Gly Asp Ala Asp Gly Ala Arg Lys Ala Met Met Ala His Leu Ser Phe
385                 390                 395                 400

Val His Thr Thr Met Lys Arg Phe Asp Glu Asp Gln Ala Arg His Ala
                405                 410                 415

Arg Ile Thr Arg Leu Pro Gly Glu His Asn Glu His Ser Arg Glu Lys
            420                 425                 430

Asn Ala Leu Lys Arg Ser Thr Met Val Ser Lys Gly Glu Glu Leu Phe
        435                 440                 445

Thr Gly Val Val Pro Ile Leu Val Glu Leu Asp Gly Asp Val Asn Gly
    450                 455                 460

His Lys Phe Ser Val Ser Gly Glu Gly Glu Gly Asp Ala Thr Tyr Gly
465                 470                 475                 480

Lys Leu Thr Leu Lys Leu Ile Cys Thr Thr Gly Lys Leu Pro Val Pro
                485                 490                 495

Trp Pro Thr Leu Val Thr Thr Leu Gly Tyr Gly Leu Gln Cys Phe Ala
            500                 505                 510

Arg Tyr Pro Asp His Met Lys Gln His Asp Phe Phe Lys Ser Ala Met
        515                 520                 525

Pro Glu Gly Tyr Val Gln Glu Arg Thr Ile Phe Phe Lys Asp Asp Gly
    530                 535                 540
```

```
Asn Tyr Lys Thr Arg Ala Glu Val Lys Phe Glu Gly Asp Thr Leu Val
545                 550                 555                 560

Asn Arg Ile Glu Leu Lys Gly Ile Asp Phe Lys Glu Asp Gly Asn Ile
                565                 570                 575

Leu Gly His Lys Leu Glu Tyr Asn Tyr Asn Ser His Asn Val Tyr Ile
            580                 585                 590

Thr Ala Asp Lys Gln Lys Asn Gly Ile Lys Ala Asn Phe Lys Ile Arg
        595                 600                 605

His Asn Ile Glu Asp Gly Gly Val Gln Leu Ala Asp His Tyr Gln Gln
    610                 615                 620

Asn Thr Pro Ile Gly Asp Gly Pro Val Leu Leu Pro Asp Asn His Tyr
625                 630                 635                 640

Leu Ser Tyr Gln Ser Ala Leu Ser Lys Asp Pro Asn Glu Lys Arg Asp
                645                 650                 655

His Met Val Leu Leu Glu Phe Val Thr Ala Ala Gly Ile Thr Leu Gly
            660                 665                 670

Met Asp Glu Leu Tyr Lys
        675


<210> SEQ ID NO 14
<211> LENGTH: 654
<212> TYPE: PRT
<213> ORGANISM: Artificial Sequence
<220> FEATURE:
<223> OTHER INFORMATION: Synthetic

<400> SEQUENCE: 14

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220
```

```
Arg Asn Ser Thr Asp Gly Met Asp Glu Leu Tyr Lys Arg Ser Gly Thr
225                 230                 235                 240

Thr Ser Leu Tyr Lys Lys Ala Gly Ser Glu Phe Ala Leu Gly Thr Gly
                245                 250                 255

Gln Ala Leu Ser Leu Ser Val Thr Leu Gln Leu Val Thr Asn Gln Val
            260                 265                 270

Gly His His Asp Ile Tyr Glu Thr Arg Gln Leu Leu Glu Gly Trp Ala
        275                 280                 285

Ala Leu His Ser Ser Ala Glu Arg Gly Asp Trp Asp Val Ala Glu Ala
    290                 295                 300

Leu Leu Glu Lys Met Asp Asp Pro Ser Leu Pro Leu Glu Asp Phe Leu
305                 310                 315                 320

Arg Phe Asp Ala Glu Phe His Val Val Ile Ser Lys Gly Ala Glu Asn
                325                 330                 335

Pro Leu Ile Ser Thr Leu Met Glu Ala Leu Arg Leu Ser Val Ala Asp
            340                 345                 350

His Thr Val Ala Arg Ala Arg Ala Leu Pro Asp Trp Arg Ala Thr Ser
        355                 360                 365

Ala Arg Leu Gln Lys Glu His Arg Ala Ile Leu Ala Ala Leu Arg Ala
    370                 375                 380

Gly Glu Ser Thr Val Ala Ala Thr Leu Ile Lys Glu His Ile Glu Gly
385                 390                 395                 400

Tyr Tyr Glu Glu Thr Ala Ala Ala Glu Ala Leu Lys Arg Ser Thr Met
                405                 410                 415

Val Ser Lys Gly Glu Glu Leu Phe Thr Gly Val Val Pro Ile Leu Val
            420                 425                 430

Glu Leu Asp Gly Asp Val Asn Gly His Lys Phe Ser Val Ser Gly Glu
        435                 440                 445

Gly Glu Gly Asp Ala Thr Tyr Gly Lys Leu Thr Leu Lys Leu Ile Cys
    450                 455                 460

Thr Thr Gly Lys Leu Pro Val Pro Trp Pro Thr Leu Val Thr Thr Leu
465                 470                 475                 480

Gly Tyr Gly Leu Gln Cys Phe Ala Arg Tyr Pro Asp His Met Lys Gln
                485                 490                 495

His Asp Phe Phe Lys Ser Ala Met Pro Glu Gly Tyr Val Gln Glu Arg
            500                 505                 510

Thr Ile Phe Phe Lys Asp Asp Gly Asn Tyr Lys Thr Arg Ala Glu Val
        515                 520                 525

Lys Phe Glu Gly Asp Thr Leu Val Asn Arg Ile Glu Leu Lys Gly Ile
    530                 535                 540

Asp Phe Lys Glu Asp Gly Asn Ile Leu Gly His Lys Leu Glu Tyr Asn
545                 550                 555                 560

Tyr Asn Ser His Asn Val Tyr Ile Thr Ala Asp Lys Gln Lys Asn Gly
                565                 570                 575

Ile Lys Ala Asn Phe Lys Ile Arg His Asn Ile Glu Asp Gly Gly Val
            580                 585                 590

Gln Leu Ala Asp His Tyr Gln Gln Asn Thr Pro Ile Gly Asp Gly Pro
        595                 600                 605

Val Leu Leu Pro Asp Asn His Tyr Leu Ser Tyr Gln Ser Ala Leu Ser
    610                 615                 620

Lys Asp Pro Asn Glu Lys Arg Asp His Met Val Leu Leu Glu Phe Val
625                 630                 635                 640
```

```
Thr Ala Ala Gly Ile Thr Leu Gly Met Asp Glu Leu Tyr Lys
                645                 650


<210> SEQ ID NO 15
<211> LENGTH: 663
<212> TYPE: PRT
<213> ORGANISM: Artificial Sequence
<220> FEATURE:
<223> OTHER INFORMATION: Synthetic

<400> SEQUENCE: 15

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Glu Gln Asn Ile Val Gln Pro Leu Lys Thr Leu Met Ala Asp Asp Pro
                245                 250                 255

Asp Tyr Ser Phe Asp Ile Leu Glu Ala Arg Tyr Ala Ile Glu Ala Ser
            260                 265                 270

Thr Ala Trp His Ala Ala Met Arg Ala Thr Pro Gly Asp Lys Glu Lys
        275                 280                 285

Ile Gln Leu Cys Phe Glu Ala Thr Leu Ser Glu Asp Pro Asp Ile Ala
    290                 295                 300

Ser Gln Ala Asp Val Arg Phe His Leu Ala Ile Ala Glu Ala Ser His
305                 310                 315                 320

Asn Ile Val Leu Leu Gln Thr Met Arg Gly Phe Phe Asp Val Leu Gln
                325                 330                 335

Ser Ser Val Lys His Ser Arg Gln Arg Met Tyr Leu Val Pro Pro Val
            340                 345                 350
```

```
Phe Ser Gln Leu Thr Glu Gln His Gln Ala Val Ile Asp Ala Ile Phe
        355                 360                 365

Ala Gly Asp Ala Asp Gly Ala Arg Lys Ala Met Met Ala His Leu Ser
    370                 375                 380

Phe Val His Thr Thr Met Lys Arg Phe Asp Glu Asp Gln Ala Arg His
385                 390                 395                 400

Ala Arg Ile Thr Arg Leu Pro Gly Glu His Asn Glu His Ser Arg Glu
                405                 410                 415

Lys Asn Ala Leu Lys Arg Ser Thr Met Val Ser Lys Gly Glu Glu Leu
            420                 425                 430

Phe Thr Gly Val Val Pro Ile Leu Val Glu Leu Asp Gly Asp Val Asn
        435                 440                 445

Gly His Lys Phe Ser Val Ser Gly Glu Gly Glu Gly Asp Ala Thr Tyr
    450                 455                 460

Gly Lys Leu Thr Leu Lys Leu Ile Cys Thr Thr Gly Lys Leu Pro Val
465                 470                 475                 480

Pro Trp Pro Thr Leu Val Thr Thr Leu Gly Tyr Gly Leu Gln Cys Phe
                485                 490                 495

Ala Arg Tyr Pro Asp His Met Lys Gln His Asp Phe Phe Lys Ser Ala
            500                 505                 510

Met Pro Glu Gly Tyr Val Gln Glu Arg Thr Ile Phe Phe Lys Asp Asp
        515                 520                 525

Gly Asn Tyr Lys Thr Arg Ala Glu Val Lys Phe Glu Gly Asp Thr Leu
    530                 535                 540

Val Asn Arg Ile Glu Leu Lys Gly Ile Asp Phe Lys Glu Asp Gly Asn
545                 550                 555                 560

Ile Leu Gly His Lys Leu Glu Tyr Asn Tyr Asn Ser His Asn Val Tyr
                565                 570                 575

Ile Thr Ala Asp Lys Gln Lys Asn Gly Ile Lys Ala Asn Phe Lys Ile
            580                 585                 590

Arg His Asn Ile Glu Asp Gly Gly Val Gln Leu Ala Asp His Tyr Gln
        595                 600                 605

Gln Asn Thr Pro Ile Gly Asp Gly Pro Val Leu Leu Pro Asp Asn His
    610                 615                 620

Tyr Leu Ser Tyr Gln Ser Ala Leu Ser Lys Asp Pro Asn Glu Lys Arg
625                 630                 635                 640

Asp His Met Val Leu Leu Glu Phe Val Thr Ala Ala Gly Ile Thr Leu
                645                 650                 655

Gly Met Asp Glu Leu Tyr Lys
            660
```

<210> SEQ ID NO 16
<211> LENGTH: 639
<212> TYPE: PRT
<213> ORGANISM: Artificial Sequence
<220> FEATURE:
<223> OTHER INFORMATION: Synthetic

<400> SEQUENCE: 16

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45
```

```
Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys Arg Ser Gly Thr
225                 230                 235                 240

Gly Gln Ala Leu Ser Leu Ser Val Thr Leu Gln Leu Val Thr Asn Gln
                245                 250                 255

Val Gly His His Asp Ile Tyr Glu Thr Arg Gln Leu Leu Glu Gly Trp
            260                 265                 270

Ala Ala Leu His Ser Ser Ala Glu Arg Gly Asp Trp Asp Val Ala Glu
        275                 280                 285

Ala Leu Leu Glu Lys Met Asp Asp Pro Ser Leu Pro Leu Glu Asp Phe
    290                 295                 300

Leu Arg Phe Asp Ala Glu Phe His Val Val Ile Ser Lys Gly Ala Glu
305                 310                 315                 320

Asn Pro Leu Ile Ser Thr Leu Met Glu Ala Leu Arg Leu Ser Val Ala
                325                 330                 335

Asp His Thr Val Ala Arg Ala Arg Ala Leu Pro Asp Trp Arg Ala Thr
            340                 345                 350

Ser Ala Arg Leu Gln Lys Glu His Arg Ala Ile Leu Ala Ala Leu Arg
        355                 360                 365

Ala Gly Glu Ser Thr Val Ala Ala Thr Leu Ile Lys Glu His Ile Glu
    370                 375                 380

Gly Tyr Tyr Glu Glu Thr Ala Ala Ala Glu Ala Leu Lys Arg Ser Thr
385                 390                 395                 400

Met Val Ser Lys Gly Glu Glu Leu Phe Thr Gly Val Val Pro Ile Leu
                405                 410                 415

Val Glu Leu Asp Gly Asp Val Asn Gly His Lys Phe Ser Val Ser Gly
            420                 425                 430

Glu Gly Glu Gly Asp Ala Thr Tyr Gly Lys Leu Thr Leu Lys Leu Ile
        435                 440                 445

Cys Thr Thr Gly Lys Leu Pro Val Pro Trp Pro Thr Leu Val Thr Thr
    450                 455                 460

Leu Gly Tyr Gly Leu Gln Cys Phe Ala Arg Tyr Pro Asp His Met Lys
```

-continued

```
465                 470                 475                 480

Gln His Asp Phe Phe Lys Ser Ala Met Pro Glu Gly Tyr Val Gln Glu
                485                 490                 495

Arg Thr Ile Phe Phe Lys Asp Asp Gly Asn Tyr Lys Thr Arg Ala Glu
            500                 505                 510

Val Lys Phe Glu Gly Asp Thr Leu Val Asn Arg Ile Glu Leu Lys Gly
        515                 520                 525

Ile Asp Phe Lys Glu Asp Gly Asn Ile Leu Gly His Lys Leu Glu Tyr
    530                 535                 540

Asn Tyr Asn Ser His Asn Val Tyr Ile Thr Ala Asp Lys Gln Lys Asn
545                 550                 555                 560

Gly Ile Lys Ala Asn Phe Lys Ile Arg His Asn Ile Glu Asp Gly Gly
                565                 570                 575

Val Gln Leu Ala Asp His Tyr Gln Gln Asn Thr Pro Ile Gly Asp Gly
            580                 585                 590

Pro Val Leu Leu Pro Asp Asn His Tyr Leu Ser Tyr Gln Ser Ala Leu
        595                 600                 605

Ser Lys Asp Pro Asn Glu Lys Arg Asp His Met Val Leu Leu Glu Phe
    610                 615                 620

Val Thr Ala Ala Gly Ile Thr Leu Gly Met Asp Glu Leu Tyr Lys
625                 630                 635
```

<210> SEQ ID NO 17
<211> LENGTH: 2319
<212> TYPE: DNA
<213> ORGANISM: Artificial Sequence
<220> FEATURE:
<223> OTHER INFORMATION: Synthetic

<400> SEQUENCE: 17

```
atggtgagca agggcgagga gaccacaatg ggcgtaatca agcccgacat gaagatcaag      60

ctgaagatgg agggcaacgt gaatggccac gccttcgtga tcgagggcga gggcgagggc     120

aagccctacg acggcaccaa caccatcaac ctggaggtga aggagggagc ccccctgccc     180

ttctcctacg acattctgac caccgcgttc gcctacggca acagggcctt caccaagtac     240

cccgacgaca tccccaacta cttcaagcag tccttccccg agggctactc ttgggagcgc     300

accatgacct tcgaggacaa gggcatcgtg aaggtgaagt ccgacatctc catggaggag     360

gactccttca tctacgagat acacctcaag ggcgagaact tcccccccaa cggccccgtg     420

atgcagaaga agaccaccgg ctgggacgcc tccaccgaga ggatgtacgt gcgcgacggc     480

gtgctgaagg gcgacgtcaa gcacaagctg ctgctggagg gcggcggcca ccaccgcgtt     540

gacttcaaga ccatctacag ggccaagaag gcggtgaagc tgcccgacta tcactttgtg     600

gaccaccgca tcgagatcct gaaccacgac aaggactaca acaaggtgac cgtttacgag     660

agcgccgtgg cccgcaactc caccgacggc atggacgagc tgtacaagag atctggtacc     720

acaagtttgt acaaaaaagc aggctccgaa ttcgcccttg gtaccatgat tgttttaccc     780

agacgcctgt cagacgaggt tgccgatcgt gtgcgggcgc tgattgatga aaaaaacctg     840

gaagcgggca tgaagttgcc cgctgagcgc caactggcga tgcaactcgg cgtatcacgt     900

aattcactgc gcgaggcgct ggcaaaactg gtgagtgaag gcgtgctgct cagtcgacgc     960

ggcggcggga cgtttattcg ctggcgtcat gacacatggt cggagcaaaa catcgtccag    1020

ccgctaaaaa cactgatggc cgatgatccg gattacagtt tcgatattct ggaagcccgc    1080

tacgccattg aagccagcac cgcatggcat gcggcaatgc gcgccacacc tggcgacaaa    1140
```

```
gaaaagattc agctttgctt tgaagcaacg ctaagtgaag acccggatat cgcctcacaa   1200

gcggacgttc gttttcatct ggcgattgcc gaagcctcac ataacatcgt gctgctgcaa   1260

accatgcgcg gtttcttcga tgtcctgcaa tcctcagtga agcatagccg tcagcggatg   1320

tatctggtgc caccggtttt ttcacaactg accgaacaac atcaggctgt cattgacgcc   1380

atttttgccg gtgatgctga cggggcgcgt aaagcaatga tggcgcacct tagttttgtt   1440

cacaccacca tgaaacgatt cgatgaagat caggctcgcc acgcacggat tacccgcctg   1500

cccggtgagc ataatgagca ttcgagggag aaaaacgcac ttaagaaggg cgaattcgac   1560

ccagctttct tgtacaaagt ggtgcttaag agatctacca tggtgagcaa gggcgaggag   1620

ctgttcaccg gggtggtgcc catcctggtc gagctggacg gcgacgtaaa cggccacaag   1680

ttcagcgtgt ccggcgaggg cgagggcgat gccacctacg gcaagctgac cctgaagctg   1740

atctgcacca ccggcaagct gcccgtgccc tggcccaccc tcgtgaccac cctgggctac   1800

ggcctgcagt gcttcgcccg ctaccccgac cacatgaagc agcacgactt cttcaagtcc   1860

gccatgcccg aaggctacgt ccaggagcgc accatcttct tcaaggacga cggcaactac   1920

aagacccgcg ccgaggtgaa gttcgagggc gacaccctgg tgaaccgcat cgagctgaag   1980

ggcatcgact tcaaggagga cggcaacatc ctggggcaca agctggagta caactacaac   2040

agccacaacg tctatatcac cgccgacaag cagaagaacg gcatcaaggc caacttcaag   2100

atccgccaca acatcgagga cggcggcgtg cagctcgccg accactacca gcagaacacc   2160

cccatcggcg acggccccgt gctgctgccc gacaaccact acctgagcta ccagtccgcc   2220

ctgagcaaag accccaacga gaagcgcgat cacatggtcc tgctggagtt cgtgaccgcc   2280

gccgggatca ctctcggcat ggacgagctg tacaagtaa                          2319
```

<210> SEQ ID NO 18
<211> LENGTH: 2238
<212> TYPE: DNA
<213> ORGANISM: Artificial Sequence
<220> FEATURE:
<223> OTHER INFORMATION: Synthetic

<400> SEQUENCE: 18

```
atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420

atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660

agcgccgtgg cccgcaactc caccgacggc atggacgagc tgtacaagag atctggtacc    720

acaagtttgt acaaaaaagc aggctccgaa ttcgcccttg gtaccatgag tgtgaaagca    780

catgaatctg tcatggattg ggtcaccgag gagctccgca gcggtcgcct aaaaatcggt    840
```

```
gaccacctcc ccagcgaacg ggcgctctcc gaaaccctcg gagtttcccg aagctccctg    900

cgcgaggcgc ttcgtgtgct cgaagccctc ggcaccattt ccaccgccac cggctccggc    960

ccgcggtctg gcaccatcat cactgctgcc cctggccagg cgctttccct ctccgtgacg   1020

ctgcagttgg tcaccaacca ggtcggccac cacgatattt atgaaacccg ccaactcctt   1080

gaaggctggg ctgccctgca ttccagcgcc gaacgtggcg actgggacgt ggcagaagcg   1140

ttgctggaaa agatggacga cccctcgcta ccgctcgagg attttttgcg tttcgacgcc   1200

gaattccacg ttgttatctc caaaggcgcg gaaaaccctc tgatcagtac gctcatggaa   1260

gccctccgtt tgtccgtggc agatcacacc gttgccaggg cccgggcgct ccccgattgg   1320

cgagccacct cggcgcgtct gcagaaagaa caccgcgcaa tcctcgcagc acttcgcgca   1380

ggcgaatcca cagtggccgc aaccttgatc aaagaacaca tcgaaggcta ctacgaagaa   1440

accgctgccg ccgaggccct taagaagggc gaattcgacc cagctttctt gtacaaagtg   1500

gtgcttaaga gatctaccat ggtgagcaag ggcgaggagc tgttcaccgg ggtggtgccc   1560

atcctggtcg agctggacgg cgacgtaaac ggccacaagt tcagcgtgtc cggcgagggc   1620

gagggcgatg ccacctacgg caagctgacc ctgaagctga tctgcaccac cggcaagctg   1680

cccgtgccct ggcccaccct cgtgaccacc ctgggctacg gcctgcagtg cttcgcccgc   1740

taccccgacc acatgaagca gcacgacttc ttcaagtccg ccatgcccga aggctacgtc   1800

caggagcgca ccatcttctt caaggacgac ggcaactaca agacccgcgc cgaggtgaag   1860

ttcgagggcg acaccctggt gaaccgcatc gagctgaagg gcatcgactt caaggaggac   1920

ggcaacatcc tggggcacaa gctggagtac aactacaaca gccacaacgt ctatatcacc   1980

gccgacaagc agaagaacgg catcaaggcc aacttcaaga tccgccacaa catcgaggac   2040

ggcggcgtgc agctcgccga ccactaccag cagaacaccc ccatcggcga cggccccgtg   2100

ctgctgcccg acaaccacta cctgagctac cagtccgccc tgagcaaaga ccccaacgag   2160

aagcgcgatc acatggtcct gctggagttc gtgaccgccg ccgggatcac tctcggcatg   2220

gacgagctgt acaagtaa                                                 2238
```

```
<210> SEQ ID NO 19
<211> LENGTH: 2274
<212> TYPE: DNA
<213> ORGANISM: Artificial Sequence
<220> FEATURE:
<223> OTHER INFORMATION: Synthetic

<400> SEQUENCE: 19
```

```
atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420

atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660
```

```
agcgccgtgg cccgcaactc caccgacggc atggacgagc tgtacaagag atctggtacc    720

atgattgttt tacccagacg cctgtcagac gaggttgccg atcgtgtgcg ggcgctgatt    780

gatgaaaaaa acctggaagc gggcatgaag ttgcccgctg agcgccaact ggcgatgcaa    840

ctcggcgtat cacgtaattc actgcgcgag gcgctggcaa aactggtgag tgaaggcgtg    900

ctgctcagtc gacgcggcgg cgggacgttt attcgctggc gtcatgacac atggtcggag    960

caaaacatcg tccagccgct aaaaacactg atggccgatg atccggatta cagtttcgat   1020

attctggaag cccgctacgc cattgaagcc agcaccgcat ggcatgcggc aatgcgcgcc   1080

acacctggcg acaaagaaaa gattcagctt tgctttgaag caacgctaag tgaagacccg   1140

gatatcgcct cacaagcgga cgttcgtttt catctggcga ttgccgaagc ctcacataac   1200

atcgtgctgc tgcaaaccat gcgcggtttc ttcgatgtcc tgcaatcctc agtgaagcat   1260

agccgtcagc ggatgtatct ggtgccaccg gtttttcac aactgaccga acaacatcag    1320

gctgtcattg acgccatttt tgccggtgat gctgacgggg cgcgtaaagc aatgatggcg   1380

caccttagtt ttgttcacac caccatgaaa cgattcgatg aagatcaggc tcgccacgca   1440

cggattaccc gcctgcccgg tgagcataat gagcattcga gggagaaaaa cgcacttaag   1500

aagggcgaat tcgacccagc tttcttgtac aaagtggtgc ttaagagatc taccatggtg   1560

agcaagggcg aggagctgtt caccggggtg gtgcccatcc tggtcgagct ggacggcgac   1620

gtaaacggcc acaagttcag cgtgtccggc gagggcgagg gcgatgccac ctacggcaag   1680

ctgaccctga agctgatctg caccaccggc aagctgcccg tgccctggcc caccctcgtg   1740

accaccctgg gctacggcct gcagtgcttc gcccgctacc ccgaccacat gaagcagcac   1800

gacttcttca agtccgccat gcccgaaggc tacgtccagg agcgcaccat cttcttcaag   1860

gacgacggca actacaagac ccgcgccgag gtgaagttcg agggcgacac cctggtgaac   1920

cgcatcgagc tgaagggcat cgacttcaag gaggacggca acatcctggg gcacaagctg   1980

gagtacaact acaacagcca caacgtctat atcaccgccg acaagcagaa gaacggcatc   2040

aaggccaact tcaagatccg ccacaacatc gaggacggcg gcgtgcagct cgccgaccac   2100

taccagcaga acacccccat cggcgacggc cccgtgctgc tgcccgacaa ccactacctg   2160

agctaccagt ccgccctgag caaagacccc aacgagaagc gcgatcacat ggtcctgctg   2220

gagttcgtga ccgccgccgg gatcactctc ggcatggacg agctgtacaa gtaa         2274
```

<210> SEQ ID NO 20
<211> LENGTH: 2193
<212> TYPE: DNA
<213> ORGANISM: Artificial Sequence
<220> FEATURE:
<223> OTHER INFORMATION: Synthetic

<400> SEQUENCE: 20

```
atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420
```

```
atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660

agcgccgtgg cccgcaactc caccgacggc atggacgagc tgtacaagag atctggtacc    720

atgagtgtga aagcacatga atctgtcatg gattgggtca ccgaggagct ccgcagcggt    780

cgcctaaaaa tcggtgacca cctccccagc gaacgggcgc tctccgaaac cctcggagtt    840

tcccgaagct ccctgcgcga ggcgcttcgt gtgctcgaag ccctcggcac catttccacc    900

gccaccggct ccggcccgcg gtctggcacc atcatcactg ctgcccctgg ccaggcgctt    960

tccctctccg tgacgctgca gttggtcacc aaccaggtcg gccaccacga tatttatgaa   1020

acccgccaac tccttgaagg ctgggctgcc ctgcattcca gcgccgaacg tggcgactgg   1080

gacgtggcag aagcgttgct ggaaaagatg gacgacccct cgctaccgct cgaggatttt   1140

ttgcgtttcg acgccgaatt ccacgttgtt atctccaaag gcgcggaaaa ccctctgatc   1200

agtacgctca tggaagccct ccgtttgtcc gtggcagatc acaccgttgc cagggcccgg   1260

gcgctccccg attggcgagc cacctcggcg cgtctgcaga aagaacaccg cgcaatcctc   1320

gcagcacttc gcgcaggcga atccacagtg gccgcaacct tgatcaaaga acacatcgaa   1380

ggctactacg aagaaaccgc tgccgccgag gcccttaaga agggcgaatt cgacccagct   1440

ttcttgtaca aagtggtgct taagagatct accatggtga gcaagggcga ggagctgttc   1500

accggggtgg tgcccatcct ggtcgagctg gacggcgacg taaacggcca caagttcagc   1560

gtgtccggcg agggcgaggg cgatgccacc tacggcaagc tgaccctgaa gctgatctgc   1620

accaccggca agctgcccgt gccctggccc accctcgtga ccaccctggg ctacggcctg   1680

cagtgcttcg cccgctaccc cgaccacatg aagcagcacg acttcttcaa gtccgccatg   1740

cccgaaggct acgtccagga gcgcaccatc ttcttcaagg acgacggcaa ctacaagacc   1800

cgcgccgagg tgaagttcga gggcgacacc ctggtgaacc gcatcgagct gaagggcatc   1860

gacttcaagg aggacggcaa catcctgggg cacaagctgg agtacaacta caacagccac   1920

aacgtctata tcaccgccga caagcagaag aacggcatca aggccaactt caagatccgc   1980

cacaacatcg aggacggcgg cgtgcagctc gccgaccact accagcagaa cacccccatc   2040

ggcgacggcc ccgtgctgct gcccgacaac cactacctga gctaccagtc cgccctgagc   2100

aaagacccca acgagaagcg cgatcacatg gtcctgctgg agttcgtgac cgccgccggg   2160

atcactctcg gcatggacga gctgtacaag taa                               2193
```

```
<210> SEQ ID NO 21
<211> LENGTH: 2274
<212> TYPE: DNA
<213> ORGANISM: Artificial Sequence
<220> FEATURE:
<223> OTHER INFORMATION: Synthetic

<400> SEQUENCE: 21

atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300
```

```
accatgacct tcgaggacaa gggcatcgtg aaggtgaagt ccgacatctc catggaggag    360
gactccttca tctacgagat acacctcaag ggcgagaact tccccccaa cggccccgtg     420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagag atctggtacc    720
acaagtttgt acaaaaaagc aggctccgaa ttcgcccttg gtaccatgat tgttttaccc    780
agacgcctgt cagacgaggt tgccgatcgt gtgcgggcgc tgattgatga aaaaaacctg    840
gaagcgggca tgaagttgcc cgctgagcgc caactggcga tgcaactcgg cgtatcacgt    900
aattcactgc gcgaggcgct ggcaaaactg gtgagtgaag gcgtgctgct cagtcgacgc    960
ggcggcggga cgtttattcg ctggcgtcat gacacatggt cggagcaaaa catcgtccag   1020
ccgctaaaaa cactgatggc cgatgatccg gattacagtt tcgatattct ggaagcccgc   1080
tacgccattg aagccagcac cgcatggcat gcggcaatgc gcgccacacc tggcgacaaa   1140
gaaaagattc agctttgctt tgaagcaacg ctaagtgaag acccggatat cgcctcacaa   1200
gcggacgttc gttttcatct ggcgattgcc gaagcctcac ataacatcgt gctgctgcaa   1260
accatgcgcg gtttcttcga tgtcctgcaa tcctcagtga agcatagccg tcagcggatg   1320
tatctggtgc caccggtttt ttcacaactg accgaacaac atcaggctgt cattgacgcc   1380
atttttgccg gtgatgctga cggggcgcgt aaagcaatga tggcgcacct tagttttgtt   1440
cacaccacca tgaaacgatt cgatgaagat caggctcgcc acgcacggat tacccgcctg   1500
cccggtgagc ataatgagca ttcgagggag aaaaacgcac ttaagagatc taccatggtg   1560
agcaagggcg aggagctgtt caccggggtg gtgcccatcc tggtcgagct ggacggcgac   1620
gtaaacggcc acaagttcag cgtgtccggc gagggcgagg gcgatgccac ctacggcaag   1680
ctgaccctga agctgatctg caccaccggc aagctgcccg tgccctggcc caccctcgtg   1740
accaccctgg gctacggcct gcagtgcttc gcccgctacc ccgaccacat gaagcagcac   1800
gacttcttca agtccgccat gcccgaaggc tacgtccagg agcgcaccat cttcttcaag   1860
gacgacggca actacaagac ccgcgccgag gtgaagttcg agggcgacac cctggtgaac   1920
cgcatcgagc tgaagggcat cgacttcaag gaggacggca acatcctggg gcacaagctg   1980
gagtacaact acaacagcca caacgtctat atcaccgccg acaagcagaa gaacggcatc   2040
aaggccaact tcaagatccg ccacaacatc gaggacggcg gcgtgcagct cgccgaccac   2100
taccagcaga acacccccat cggcgacggc cccgtgctgc tgcccgacaa ccactacctg   2160
agctaccagt ccgccctgag caaagacccc aacgagaagc gcgatcacat ggtcctgctg   2220
gagttcgtga ccgccgccgg gatcactctc ggcatggacg agctgtacaa gtaa         2274
```

```
<210> SEQ ID NO 22
<211> LENGTH: 2193
<212> TYPE: DNA
<213> ORGANISM: Artificial Sequence
<220> FEATURE:
<223> OTHER INFORMATION: Synthetic

<400> SEQUENCE: 22

atggtgagca agggcgagga gaccacaatg ggcgtaatca agcccgacat gaagatcaag     60
```

```
ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420

atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660

agcgccgtgg cccgcaactc caccgacggc atggacgagc tgtacaagag atctggtacc    720

acaagtttgt acaaaaaagc aggctccgaa ttcgcccttg gtaccatgag tgtgaaagca    780

catgaatctg tcatggattg ggtcaccgag gagctccgca gcggtcgcct aaaaatcggt    840

gaccacctcc ccagcgaacg ggcgctctcc gaaaccctcg gagtttcccg aagctccctg    900

cgcgaggcgc ttcgtgtgct cgaagccctc ggcaccattt ccaccgccac cggctccggc    960

ccgcggtctg gcaccatcat cactgctgcc cctggccagg cgctttccct ctccgtgacg   1020

ctgcagttgg tcaccaacca ggtcggccac cacgatattt atgaaacccg ccaactcctt   1080

gaaggctggg ctgccctgca ttccagcgcc gaacgtggcg actgggacgt ggcagaagcg   1140

ttgctggaaa agatggacga cccctcgcta ccgctcgagg atttttgcg tttcgacgcc   1200

gaattccacg ttgttatctc caaaggcgcg gaaaaccctc tgatcagtac gctcatggaa   1260

gccctccgtt tgtccgtggc agatcacacc gttgccaggg cccgggcgct ccccgattgg   1320

cgagccacct cggcgcgtct gcagaaagaa caccgcgcaa tcctcgcagc acttcgcgca   1380

ggcgaatcca cagtggccgc aaccttgatc aaagaacaca tcgaaggcta ctacgaagaa   1440

accgctgccg ccgaggccct taagagatct accatggtga gcaagggcga ggagctgttc   1500

accggggtgg tgcccatcct ggtcgagctg gacggcgacg taaacggcca caagttcagc   1560

gtgtccggcg agggcgaggg cgatgccacc tacggcaagc tgaccctgaa gctgatctgc   1620

accaccggca agctgcccgt gccctggccc accctcgtga ccaccctggg ctacggcctg   1680

cagtgcttcg cccgctaccc cgaccacatg aagcagcacg acttcttcaa gtccgccatg   1740

cccgaaggct acgtccagga gcgcaccatc ttcttcaagg acgacggcaa ctacaagacc   1800

cgcgccgagg tgaagttcga gggcgacacc ctggtgaacc gcatcgagct gaagggcatc   1860

gacttcaagg aggacggcaa catcctgggg cacaagctgg agtacaacta caacagccac   1920

aacgtctata tcaccgccga caagcagaag aacggcatca aggccaactt caagatccgc   1980

cacaacatcg aggacggcgg cgtgcagctc gccgaccact accagcagaa cacccccatc   2040

ggcgacggcc ccgtgctgct gcccgacaac cactacctga gctaccagtc cgccctgagc   2100

aaagacccca acgagaagcg cgatcacatg gtcctgctgg agttcgtgac cgccgccggg   2160

atcactctcg gcatggacga gctgtacaag taa                                2193
```

```
<210> SEQ ID NO 23
<211> LENGTH: 2229
<212> TYPE: DNA
<213> ORGANISM: Artificial Sequence
<220> FEATURE:
<223> OTHER INFORMATION: Synthetic
```

<400> SEQUENCE: 23

```
atggtgagca agggcgagga gaccacaatg ggcgtaatca agcccgacat gaagatcaag     60
ctgaagatgg agggcaacgt gaatggccac gccttcgtga tcgagggcga gggcgagggc    120
aagccctacg acggcaccaa caccatcaac ctggaggtga aggagggagc ccccctgccc    180
ttctcctacg acattctgac caccgcgttc gcctacggca acagggcctt caccaagtac    240
cccgacgaca tccccaacta cttcaagcag tccttccccg agggctactc ttgggagcgc    300
accatgacct tcgaggacaa gggcatcgtg aaggtgaagt ccgacatctc catggaggag    360
gactccttca tctacgagat acacctcaag ggcgagaact tcccccccaa cggccccgtg    420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagag atctggtacc    720
atgattgttt tacccagacg cctgtcagac gaggttgccg atcgtgtgcg ggcgctgatt    780
gatgaaaaaa acctggaagc gggcatgaag ttgcccgctg agcgccaact ggcgatgcaa    840
ctcggcgtat cacgtaattc actgcgcgag gcgctggcaa aactggtgag tgaaggcgtg    900
ctgctcagtc gacgcggcgg cgggacgttt attcgctggc gtcatgacac atggtcggag    960
caaaacatcg tccagccgct aaaaacactg atggccgatg atccggatta cagtttcgat   1020
attctggaag cccgctacgc cattgaagcc agcaccgcat ggcatgcggc aatgcgcgcc   1080
acacctggcg acaaagaaaa gattcagctt tgctttgaag caacgctaag tgaagacccg   1140
gatatcgcct cacaagcgga cgttcgtttt catctggcga ttgccgaagc ctcacataac   1200
atcgtgctgc tgcaaaccat gcgcggtttc ttcgatgtcc tgcaatcctc agtgaagcat   1260
agccgtcagc ggatgtatct ggtgccaccg gttttttcac aactgaccga acaacatcag   1320
gctgtcattg acgccatttt tgccggtgat gctgacgggg cgcgtaaagc aatgatggcg   1380
caccttagtt ttgttcacac caccatgaaa cgattcgatg aagatcaggc tcgccacgca   1440
cggattaccc gcctgcccgg tgagcataat gagcattcga gggagaaaaa cgcacttaag   1500
agatctacca tggtgagcaa gggcgaggag ctgttcaccg ggtggtgcc catcctggtc   1560
gagctggacg gcgacgtaaa cggccacaag ttcagcgtgt ccggcgaggg cgagggcgat   1620
gccacctacg gcaagctgac cctgaagctg atctgcacca ccggcaagct gcccgtgccc   1680
tggcccaccc tcgtgaccac cctgggctac ggcctgcagt gcttcgcccg ctaccccgac   1740
cacatgaagc agcacgactt cttcaagtcc gccatgcccg aaggctacgt ccaggagcgc   1800
accatcttct tcaaggacga cggcaactac aagacccgcg ccgaggtgaa gttcgagggc   1860
gacaccctgg tgaaccgcat cgagctgaag ggcatcgact tcaaggagga cggcaacatc   1920
ctggggcaca agctggagta caactacaac agccacaacg tctatatcac cgccgacaag   1980
cagaagaacg gcatcaaggc caacttcaag atccgccaca acatcgagga cggcggcgtg   2040
cagctcgccg accactacca gcagaacacc cccatcggcg acggccccgt gctgctgccc   2100
gacaaccact acctgagcta ccagtccgcc ctgagcaaag accccaacga gaagcgcgat   2160
cacatggtcc tgctggagtt cgtgaccgcc gccgggatca ctctcggcat ggacgagctg   2220
tacaagtaa                                                           2229
```

<210> SEQ ID NO 24
<211> LENGTH: 2148
<212> TYPE: DNA
<213> ORGANISM: Artificial Sequence
<220> FEATURE:
<223> OTHER INFORMATION: Synthetic

<400> SEQUENCE: 24

```
atggtgagca agggcgagga gaccacaatg ggcgtaatca agcccgacat gaagatcaag     60
ctgaagatgg agggcaacgt gaatggccac gccttcgtga tcgagggcga gggcgagggc    120
aagccctacg acggcaccaa caccatcaac ctggaggtga aggagggagc ccccctgccc    180
ttctcctacg acattctgac caccgcgttc gcctacggca acagggcctt caccaagtac    240
cccgacgaca tccccaacta cttcaagcag tccttccccg agggctactc ttgggagcgc    300
accatgacct tcgaggacaa gggcatcgtg aaggtgaagt ccgacatctc catggaggag    360
gactccttca tctacgagat acacctcaag ggcgagaact tcccccccaa cggccccgtg    420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagag atctggtacc    720
atgagtgtga aagcacatga atctgtcatg gattgggtca ccgaggagct ccgcagcggt    780
cgcctaaaaa tcggtgacca cctccccagc gaacgggcgc tctccgaaac cctcggagtt    840
tcccgaagct ccctgcgcga ggcgcttcgt gtgctcgaag ccctcggcac catttccacc    900
gccaccggct ccggcccgcg gtctggcacc atcatcactg ctgcccctgg ccaggcgctt    960
tccctctccg tgacgctgca gttggtcacc aaccaggtcg gccaccacga tatttatgaa   1020
acccgccaac tccttgaagg ctgggctgcc ctgcattcca gcgccgaacg tggcgactgg   1080
gacgtggcag aagcgttgct ggaaaagatg gacgacccct cgctaccgct cgaggatttt   1140
ttgcgtttcg acgccgaatt ccacgttgtt atctccaaag gcgcggaaaa ccctctgatc   1200
agtacgctca tggaagccct ccgtttgtcc gtggcagatc acaccgttgc cagggcccgg   1260
gcgctccccg attggcgagc cacctcggcg cgtctgcaga aagaacaccg cgcaatcctc   1320
gcagcacttc gcgcaggcga atccacagtg gccgcaacct tgatcaaaga acacatcgaa   1380
ggctactacg aagaaaccgc tgccgccgag gccccttaaga gatctaccat ggtgagcaag   1440
ggcgaggagc tgttcaccgg ggtggtgccc atcctggtcg agctggacgg cgacgtaaac   1500
ggccacaagt tcagcgtgtc cggcgagggc gagggcgatg ccacctacgg caagctgacc   1560
ctgaagctga tctgcaccac cggcaagctg cccgtgccct ggcccaccct cgtgaccacc   1620
ctgggctacg gcctgcagtg cttcgcccgc taccccgacc acatgaagca gcacgacttc   1680
ttcaagtccg ccatgcccga aggctacgtc caggagcgca ccatcttctt caaggacgac   1740
ggcaactaca agacccgcgc cgaggtgaag ttcgagggcg acaccctggt gaaccgcatc   1800
gagctgaagg gcatcgactt caaggaggac ggcaacatcc tggggcacaa gctggagtac   1860
aactacaaca gccacaacgt ctatatcacc gccgacaagc agaagaacgg catcaaggcc   1920
aacttcaaga tccgccacaa catcgaggac ggcggcgtgc agctcgccga ccactaccag   1980
cagaacaccc ccatcggcga cggccccgtg ctgctgcccg acaaccacta cctgagctac   2040
cagtccgccc tgagcaaaga ccccaacgag aagcgcgatc acatggtcct gctggagttc   2100
```

```
gtgaccgccg ccgggatcac tctcggcatg gacgagctgt acaagtaa              2148


<210> SEQ ID NO 25
<211> LENGTH: 2082
<212> TYPE: DNA
<213> ORGANISM: Artificial Sequence
<220> FEATURE:
<223> OTHER INFORMATION: Synthetic

<400> SEQUENCE: 25

atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420

atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660

agcgccgtgg cccgcaactc caccgacggc atggacgagc tgtacaagag atctggtacc    720

acaagtttgt acaaaaaagc aggctccgaa ttcgcccttg gtaccgagca aaacatcgtc    780

cagccgctaa aaacactgat ggccgatgat ccggattaca gtttcgatat tctggaagcc    840

cgctacgcca ttgaagccag caccgcatgg catgcggcaa tgcgcgccac acctggcgac    900

aaagaaaaga ttcagctttg ctttgaagca acgctaagtg aagacccgga tatcgcctca    960

caagcggacg ttcgttttca tctggcgatt gccgaagcct cacataacat cgtgctgctg   1020

caaaccatgc gcggtttctt cgatgtcctg caatcctcag tgaagcatag ccgtcagcgg   1080

atgtatctgg tgccaccggt tttttcacaa ctgaccgaac aacatcaggc tgtcattgac   1140

gccatttttg ccggtgatgc tgacggggcg cgtaaagcaa tgatggcgca ccttagtttt   1200

gttcacacca ccatgaaacg attcgatgaa gatcaggctc gccacgcacg gattacccgc   1260

ctgcccggtg agcataatga gcattcgagg gagaaaaacg cacttaagaa gggcgaattc   1320

gacccagctt tcttgtacaa agtggtgctt aagagatcta ccatggtgag caagggcgag   1380

gagctgttca ccggggtggt gcccatcctg gtcgagctgg acggcgacgt aaacggccac   1440

aagttcagcg tgtccggcga gggcgagggc gatgccacct acggcaagct gaccctgaag   1500

ctgatctgca ccaccggcaa gctgcccgtg ccctggccca ccctcgtgac caccctgggc   1560

tacggcctgc agtgcttcgc ccgctacccc gaccacatga agcagcacga cttcttcaag   1620

tccgccatgc ccgaaggcta cgtccaggag cgcaccatct tcttcaagga cgacggcaac   1680

tacaagaccc gcgccgaggt gaagttcgag ggcgacaccc tggtgaaccg catcgagctg   1740

aagggcatcg acttcaagga ggacggcaac atcctggggc acaagctgga gtacaactac   1800

aacagccaca acgtctatat caccgccgac aagcagaaga acggcatcaa ggccaacttc   1860

aagatccgcc acaacatcga ggacggcggc gtgcagctcg ccgaccacta ccagcagaac   1920

acccccatcg gcgacggccc cgtgctgctg cccgacaacc actacctgag ctaccagtcc   1980
```

gccctgagca aagaccccaa cgagaagcgc gatcacatgg tcctgctgga gttcgtgacc 2040
gccgccggga tcactctcgg catggacgag ctgtacaagt aa 2082

<210> SEQ ID NO 26
<211> LENGTH: 2010
<212> TYPE: DNA
<213> ORGANISM: Artificial Sequence
<220> FEATURE:
<223> OTHER INFORMATION: Synthetic

<400> SEQUENCE: 26
atggtgagca agggcgagga gaccacaatg ggcgtaatca agcccgacat gaagatcaag 60
ctgaagatgg agggcaacgt gaatggccac gccttcgtga tcgagggcga gggcgagggc 120
aagccctacg acggcaccaa caccatcaac ctggaggtga aggagggagc ccccctgccc 180
ttctcctacg acattctgac caccgcgttc gcctacggca acagggcctt caccaagtac 240
cccgacgaca tccccaacta cttcaagcag tccttccccg agggctactc ttgggagcgc 300
accatgacct tcgaggacaa gggcatcgtg aaggtgaagt ccgacatctc catggaggag 360
gactccttca tctacgagat acacctcaag ggcgagaact tcccccccaa cggccccgtg 420
atgcagaaga agaccaccgg ctgggacgcc tccaccgaga ggatgtacgt gcgcgacggc 480
gtgctgaagg gcgacgtcaa gcacaagctg ctgctggagg gcggcggcca ccaccgcgtt 540
gacttcaaga ccatctacag ggccaagaag gcggtgaagc tgcccgacta tcactttgtg 600
gaccaccgca tcgagatcct gaaccacgac aaggactaca acaaggtgac cgtttacgag 660
agcgccgtgg cccgcaactc caccgacggc atggacgagc tgtacaagag atctggtacc 720
acaagtttgt acaaaaaagc aggctccgaa ttcgcccttg gtaccggcca ggcgctttcc 780
ctctccgtga cgctgcagtt ggtcaccaac caggtcggcc accacgatat ttatgaaacc 840
cgccaactcc ttgaaggctg ggctgccctg cattccagcg ccgaacgtgg cgactgggac 900
gtggcagaag cgttgctgga aaagatggac gacccctcgc taccgctcga ggattttttg 960
cgtttcgacg ccgaattcca cgttgttatc tccaaaggcg cggaaaaccc tctgatcagt 1020
acgctcatgg aagccctccg tttgtccgtg gcagatcaca ccgttgccag ggcccgggcg 1080
ctccccgatt ggcgagccac ctcggcgcgt ctgcagaaag aacaccgcgc aatcctcgca 1140
gcacttcgcg caggcgaatc cacagtggcc gcaaccttga tcaaagaaca catcgaaggc 1200
tactacgaag aaaccgctgc cgccgaggcc cttaagaagg gcgaattcga cccagctttc 1260
ttgtacaaag tggtgcttaa gagatctacc atggtgagca agggcgagga gctgttcacc 1320
ggggtggtgc ccatcctggt cgagctggac ggcgacgtaa acggccacaa gttcagcgtg 1380
tccggcgagg gcgagggcga tgccacctac ggcaagctga ccctgaagct gatctgcacc 1440
accggcaagc tgcccgtgcc ctggcccacc ctcgtgacca ccctgggcta cggcctgcag 1500
tgcttcgccc gctaccccga ccacatgaag cagcacgact tcttcaagtc cgccatgccc 1560
gaaggctacg tccaggagcg caccatcttc ttcaaggacg acggcaacta caagacccgc 1620
gccgaggtga agttcgaggg cgacaccctg gtgaaccgca tcgagctgaa gggcatcgac 1680
ttcaaggagg acggcaacat cctggggcac aagctggagt acaactacaa cagccacaac 1740
gtctatatca ccgccgacaa gcagaagaac ggcatcaagg ccaacttcaa gatccgccac 1800
aacatcgagg acggcggcgt gcagctcgcc gaccactacc agcagaacac ccccatcggc 1860
gacggccccg tgctgctgcc cgacaaccac tacctgagct accagtccgc cctgagcaaa 1920
gaccccaacg agaagcgcga tcacatggtc ctgctggagt tcgtgaccgc cgccgggatc 1980
actctcggca tggacgagct gtacaagtaa 2010

<210> SEQ ID NO 27
<211> LENGTH: 2037
<212> TYPE: DNA
<213> ORGANISM: Artificial Sequence
<220> FEATURE:
<223> OTHER INFORMATION: Synthetic

<400> SEQUENCE: 27
atggtgagca agggcgagga gaccacaatg ggcgtaatca agcccgacat gaagatcaag 60
ctgaagatgg agggcaacgt gaatggccac gccttcgtga tcgagggcga gggcgagggc 120
aagccctacg acggcaccaa caccatcaac ctggaggtga aggagggagc ccccctgccc 180
ttctcctacg acattctgac caccgcgttc gcctacggca acagggcctt caccaagtac 240
cccgacgaca tccccaacta cttcaagcag tccttccccg agggctactc ttgggagcgc 300
accatgacct tcgaggacaa gggcatcgtg aaggtgaagt ccgacatctc catggaggag 360
gactccttca tctacgagat acacctcaag ggcgagaact tcccccccaa cggccccgtg 420
atgcagaaga agaccaccgg ctgggacgcc tccaccgaga ggatgtacgt gcgcgacggc 480
gtgctgaagg gcgacgtcaa gcacaagctg ctgctggagg gcggcggcca ccaccgcgtt 540
gacttcaaga ccatctacag ggccaagaag gcggtgaagc tgcccgacta tcactttgtg 600
gaccaccgca tcgagatcct gaaccacgac aaggactaca acaaggtgac cgtttacgag 660
agcgccgtgg cccgcaactc caccgacggc atggacgagc tgtacaagag atctggtacc 720
gagcaaaaca tcgtccagcc gctaaaaaca ctgatggccg atgatccgga ttacagtttc 780
gatattctgg aagcccgcta cgccattgaa gccagcaccg catggcatgc ggcaatgcgc 840
gccacacctg gcgacaaaga aaagattcag ctttgctttg aagcaacgct aagtgaagac 900
ccggatatcg cctcacaagc ggacgttcgt tttcatctgg cgattgccga agcctcacat 960
aacatcgtgc tgctgcaaac catgcgcggt ttcttcgatg tcctgcaatc ctcagtgaag 1020
catagccgtc agcggatgta tctggtgcca ccggtttttt cacaactgac cgaacaacat 1080
caggctgtca ttgacgccat ttttgccggt gatgctgacg gggcgcgtaa agcaatgatg 1140
gcgcacctta gttttgttca caccaccatg aaacgattcg atgaagatca ggctcgccac 1200
gcacggatta cccgcctgcc cggtgagcat aatgagcatt cgagggagaa aaacgcactt 1260
aagaagggcg aattcgaccc agctttcttg tacaaagtgg tgcttaagag atctaccatg 1320
gtgagcaagg gcgaggagct gttcaccggg gtggtgccca tcctggtcga gctggacggc 1380
gacgtaaacg gccacaagtt cagcgtgtcc ggcgagggcg agggcgatgc cacctacggc 1440
aagctgaccc tgaagctgat ctgcaccacc ggcaagctgc ccgtgccctg gcccaccctc 1500
gtgaccaccc tgggctacgg cctgcagtgc ttcgcccgct accccgacca catgaagcag 1560
cacgacttct tcaagtccgc catgcccgaa ggctacgtcc aggagcgcac catcttcttc 1620
aaggacgacg gcaactacaa gacccgcgcc gaggtgaagt tcgagggcga caccctggtg 1680
aaccgcatcg agctgaaggg catcgacttc aaggaggacg gcaacatcct ggggcacaag 1740
ctggagtaca actacaacag ccacaacgtc tatatcaccg ccgacaagca gaagaacggc 1800
atcaaggcca acttcaagat ccgccacaac atcgaggacg gcggcgtgca gctcgccgac 1860
cactaccagc agaacacccc catcggcgac ggccccgtgc tgctgcccga caaccactac 1920
ctgagctacc agtccgccct gagcaaagac cccaacgaga agcgcgatca catggtcctg 1980

```
ctggagttcg tgaccgccgc cgggatcact ctcggcatgg acgagctgta caagtaa      2037


<210> SEQ ID NO 28
<211> LENGTH: 1965
<212> TYPE: DNA
<213> ORGANISM: Artificial Sequence
<220> FEATURE:
<223> OTHER INFORMATION: Synthetic

<400> SEQUENCE: 28

atggtgagca agggcgagga gaccacaatg ggcgtaatca agcccgacat gaagatcaag     60

ctgaagatgg agggcaacgt gaatggccac gccttcgtga tcgagggcga gggcgagggc    120

aagccctacg acggcaccaa caccatcaac ctggaggtga aggagggagc ccccctgccc    180

ttctcctacg acattctgac caccgcgttc gcctacggca acagggcctt caccaagtac    240

cccgacgaca tccccaacta cttcaagcag tccttccccg agggctactc ttgggagcgc    300

accatgacct tcgaggacaa gggcatcgtg aaggtgaagt ccgacatctc catggaggag    360

gactccttca tctacgagat acacctcaag ggcgagaact tcccccccaa cggccccgtg    420

atgcagaaga agaccaccgg ctgggacgcc tccaccgaga ggatgtacgt gcgcgacggc    480

gtgctgaagg gcgacgtcaa gcacaagctg ctgctggagg gcggcggcca ccaccgcgtt    540

gacttcaaga ccatctacag ggccaagaag gcggtgaagc tgcccgacta tcactttgtg    600

gaccaccgca tcgagatcct gaaccacgac aaggactaca acaaggtgac cgtttacgag    660

agcgccgtgg cccgcaactc caccgacggc atggacgagc tgtacaagag atctggtacc    720

ggccaggcgc tttccctctc cgtgacgctg cagttggtca ccaaccaggt cggccaccac    780

gatatttatg aaacccgcca actccttgaa ggctgggctg ccctgcattc cagcgccgaa    840

cgtggcgact gggacgtggc agaagcgttg ctggaaaaga tggacgaccc ctcgctaccg    900

ctcgaggatt ttttgcgttt cgacgccgaa ttccacgttg ttatctccaa aggcgcggaa    960

aaccctctga tcagtacgct catggaagcc ctccgtttgt ccgtggcaga tcacaccgtt   1020

gccagggccc gggcgctccc cgattggcga gccacctcgg cgcgtctgca gaaagaacac   1080

cgcgcaatcc tcgcagcact tcgcgcaggc gaatccacag tggccgcaac cttgatcaaa   1140

gaacacatcg aaggctacta cgaagaaacc gctgccgccg aggcccttaa gaagggcgaa   1200

ttcgacccag ctttcttgta caaagtggtg cttaagagat ctaccatggt gagcaagggc   1260

gaggagctgt tcaccggggt ggtgcccatc ctggtcgagc tggacggcga cgtaaacggc   1320

cacaagttca gcgtgtccgg cgagggcgag ggcgatgcca cctacggcaa gctgaccctg   1380

aagctgatct gcaccaccgg caagctgccc gtgccctggc ccaccctcgt gaccaccctg   1440

ggctacggcc tgcagtgctt cgcccgctac cccgaccaca tgaagcagca cgacttcttc   1500

aagtccgcca tgcccgaagg ctacgtccag gagcgcacca tcttcttcaa ggacgacggc   1560

aactacaaga cccgcgccga ggtgaagttc gagggcgaca ccctggtgaa ccgcatcgag   1620

ctgaagggca tcgacttcaa ggaggacggc aacatcctgg ggcacaagct ggagtacaac   1680

tacaacagcc acaacgtcta tatcaccgcc gacaagcaga agaacggcat caaggccaac   1740

ttcaagatcc gccacaacat cgaggacggc ggcgtgcagc tcgccgacca ctaccagcag   1800

aacaccccca tcggcgacgg ccccgtgctg ctgcccgaca accactacct gagctaccag   1860

tccgccctga gcaaagaccc caacgagaag cgcgatcaca tggtcctgct ggagttcgtg   1920

accgccgccg ggatcactct cggcatggac gagctgtaca agtaa                   1965
```

<210> SEQ ID NO 29
<211> LENGTH: 2037
<212> TYPE: DNA
<213> ORGANISM: Artificial Sequence
<220> FEATURE:
<223> OTHER INFORMATION: Synthetic

<400> SEQUENCE: 29

```
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc ccccctgccc     180
ttctcctacg acattctgac caccgcgttc gcctacggca acagggcctt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact tcccccccaa cggccccgtg     420
atgcagaaga agaccaccgg ctgggacgcc tccaccgaga ggatgtacgt gcgcgacggc     480
gtgctgaagg gcgacgtcaa gcacaagctg ctgctggagg gcggcggcca ccaccgcgtt     540
gacttcaaga ccatctacag ggccaagaag gcggtgaagc tgcccgacta tcactttgtg     600
gaccaccgca tcgagatcct gaaccacgac aaggactaca acaaggtgac cgtttacgag     660
agcgccgtgg cccgcaactc caccgacggc atggacgagc tgtacaagag atctggtacc     720
acaagtttgt acaaaaaagc aggctccgaa ttcgcccttg gtaccgagca aaacatcgtc     780
cagccgctaa aaacactgat ggccgatgat ccggattaca gtttcgatat tctggaagcc     840
cgctacgcca ttgaagccag caccgcatgg catgcggcaa tgcgcgccac acctggcgac     900
aaagaaaaga ttcagctttg ctttgaagca acgctaagtg aagacccgga tatcgcctca     960
caagcggacg ttcgttttca tctggcgatt gccgaagcct cacataacat cgtgctgctg    1020
caaaccatgc gcggtttctt cgatgtcctg caatcctcag tgaagcatag ccgtcagcgg    1080
atgtatctgg tgccaccggt tttttcacaa ctgaccgaac aacatcaggc tgtcattgac    1140
gccatttttg ccggtgatgc tgacgggggcg cgtaaagcaa tgatggcgca ccttagtttt    1200
gttcacacca ccatgaaacg attcgatgaa gatcaggctc gccacgcacg gattacccgc    1260
ctgcccggtg agcataatga gcattcgagg gagaaaaacg cacttaagag atctaccatg    1320
gtgagcaagg gcgaggagct gttcaccggg gtggtgccca tcctggtcga gctggacggc    1380
gacgtaaacg gccacaagtt cagcgtgtcc ggcgagggcg agggcgatgc cacctacggc    1440
aagctgaccc tgaagctgat ctgcaccacc ggcaagctgc ccgtgccctg gcccaccctc    1500
gtgaccaccc tgggctacgg cctgcagtgc ttcgcccgct accccgacca catgaagcag    1560
cacgacttct tcaagtccgc catgcccgaa ggctacgtcc aggagcgcac catcttcttc    1620
aaggacgacg gcaactacaa gacccgcgcc gaggtgaagt tcgagggcga caccctggtg    1680
aaccgcatcg agctgaaggg catcgacttc aaggaggacg gcaacatcct ggggcacaag    1740
ctggagtaca actacaacag ccacaacgtc tatatcaccg ccgacaagca gaagaacggc    1800
atcaaggcca acttcaagat ccgccacaac atcgaggacg gcggcgtgca gctcgccgac    1860
cactaccagc agaacacccc catcggcgac ggccccgtgc tgctgcccga caaccactac    1920
ctgagctacc agtccgccct gagcaaagac cccaacgaga agcgcgatca catggtcctg    1980
ctggagttcg tgaccgccgc cgggatcact ctcggcatgg acgagctgta caagtaa       2037
```

<210> SEQ ID NO 30

<211> LENGTH: 1965
<212> TYPE: DNA
<213> ORGANISM: Artificial Sequence
<220> FEATURE:
<223> OTHER INFORMATION: Synthetic

<400> SEQUENCE: 30
atggtgagca agggcgagga gaccacaatg ggcgtaatca agcccgacat gaagatcaag 60
ctgaagatgg agggcaacgt gaatggccac gccttcgtga tcgagggcga gggcgagggc 120
aagccctacg acggcaccaa caccatcaac ctggaggtga aggagggagc ccccctgccc 180
ttctcctacg acattctgac caccgcgttc gcctacggca acagggcctt caccaagtac 240
cccgacgaca tccccaacta cttcaagcag tccttccccg agggctactc ttgggagcgc 300
accatgacct tcgaggacaa gggcatcgtg aaggtgaagt ccgacatctc catggaggag 360
gactccttca tctacgagat acacctcaag ggcgagaact tcccccccaa cggccccgtg 420
atgcagaaga agaccaccgg ctgggacgcc tccaccgaga ggatgtacgt gcgcgacggc 480
gtgctgaagg gcgacgtcaa gcacaagctg ctgctggagg gcggcggcca ccaccgcgtt 540
gacttcaaga ccatctacag ggccaagaag gcggtgaagc tgcccgacta tcactttgtg 600
gaccaccgca tcgagatcct gaaccacgac aaggactaca acaaggtgac cgtttacgag 660
agcgccgtgg cccgcaactc caccgacggc atggacgagc tgtacaagag atctggtacc 720
acaagtttgt acaaaaaagc aggctccgaa ttcgcccttg gtaccggcca ggcgctttcc 780
ctctccgtga cgctgcagtt ggtcaccaac caggtcggcc accacgatat ttatgaaacc 840
cgccaactcc ttgaaggctg ggctgccctg cattccagcg ccgaacgtgg cgactgggac 900
gtggcagaag cgttgctgga aaagatggac gacccctcgc taccgctcga ggatttttg 960 cgtttcgacg ccgaattcca cgttgttatc tccaaaggcg cggaaaaccc tctgatcagt 1020
acgctcatgg aagccctccg tttgtccgtg gcagatcaca ccgttgccag ggcccgggcg 1080
ctccccgatt ggcgagccac ctcggcgcgt ctgcagaaag aacaccgcgc aatcctcgca 1140
gcacttcgcg caggcgaatc cacagtggcc gcaaccttga tcaaagaaca catcgaaggc 1200
tactacgaag aaaccgctgc cgccgaggcc cttaagagat ctaccatggt gagcaagggc 1260
gaggagctgt tcaccggggt ggtgcccatc ctggtcgagc tggacggcga cgtaaacggc 1320
cacaagttca gcgtgtccgg cgagggcgag ggcgatgcca cctacggcaa gctgaccctg 1380
aagctgatct gcaccaccgg caagctgccc gtgccctggc ccaccctcgt gaccaccctg 1440
ggctacggcc tgcagtgctt cgcccgctac cccgaccaca tgaagcagca cgacttcttc 1500
aagtccgcca tgcccgaagg ctacgtccag gagcgcacca tcttcttcaa ggacgacggc 1560
aactacaaga cccgcgccga ggtgaagttc gagggcgaca ccctggtgaa ccgcatcgag 1620
ctgaagggca tcgacttcaa ggaggacggc aacatcctgg ggcacaagct ggagtacaac 1680
tacaacagcc acaacgtcta tatcaccgcc gacaagcaga agaacggcat caaggccaac 1740
ttcaagatcc gccacaacat cgaggacggc ggcgtgcagc tcgccgacca ctaccagcag 1800
aacaccccca tcggcgacgg ccccgtgctg ctgcccgaca accactacct gagctaccag 1860
tccgccctga gcaaagaccc caacgagaag cgcgatcaca tggtcctgct ggagttcgtg 1920
accgccgccg ggatcactct cggcatggac gagctgtaca agtaa 1965

<210> SEQ ID NO 31
<211> LENGTH: 1992
<212> TYPE: DNA
<213> ORGANISM: Artificial Sequence
<220> FEATURE:
<223> OTHER INFORMATION: Synthetic

<400> SEQUENCE: 31

```
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc ccccctgccc     180
ttctcctacg acattctgac caccgcgttc gcctacggca acagggcctt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact tcccccccaa cggccccgtg     420
atgcagaaga agaccaccgg ctgggacgcc tccaccgaga ggatgtacgt gcgcgacggc     480
gtgctgaagg gcgacgtcaa gcacaagctg ctgctggagg gcggcggcca ccaccgcgtt     540
gacttcaaga ccatctacag ggccaagaag gcggtgaagc tgcccgacta tcactttgtg     600
gaccaccgca tcgagatcct gaaccacgac aaggactaca acaaggtgac cgtttacgag     660
agcgccgtgg cccgcaactc caccgacggc atggacgagc tgtacaagag atctggtacc     720
gagcaaaaca tcgtccagcc gctaaaaaca ctgatggccg atgatccgga ttacagtttc     780
gatattctgg aagcccgcta cgccattgaa gccagcaccg catggcatgc ggcaatgcgc     840
gccacacctg gcgacaaaga aaagattcag ctttgctttg aagcaacgct aagtgaagac     900
ccggatatcg cctcacaagc ggacgttcgt tttcatctgg cgattgccga agcctcacat     960
aacatcgtgc tgctgcaaac catgcgcggt ttcttcgatg tcctgcaatc ctcagtgaag    1020
catagccgtc agcggatgta tctggtgcca ccggtttttt cacaactgac cgaacaacat    1080
caggctgtca ttgacgccat ttttgccggt gatgctgacg gggcgcgtaa agcaatgatg    1140
gcgcacctta gttttgttca caccaccatg aaacgattcg atgaagatca ggctcgccac    1200
gcacggatta cccgcctgcc cggtgagcat aatgagcatt cgagggagaa aaacgcactt    1260
aagagatcta ccatggtgag caagggcgag gagctgttca ccggggtggt gcccatcctg    1320
gtcgagctgg acggcgacgt aaacggccac aagttcagcg tgtccggcga gggcgagggc    1380
gatgccacct acggcaagct gaccctgaag ctgatctgca ccaccggcaa gctgcccgtg    1440
ccctggccca ccctcgtgac caccctgggc tacggcctgc agtgcttcgc ccgctacccc    1500
gaccacatga agcagcacga cttcttcaag tccgccatgc ccgaaggcta cgtccaggag    1560
cgcaccatct tcttcaagga cgacggcaac tacaagaccc gcgccgaggt gaagttcgag    1620
ggcgacaccc tggtgaaccg catcgagctg aagggcatcg acttcaagga ggacggcaac    1680
atcctggggc acaagctgga gtacaactac aacagccaca acgtctatat caccgccgac    1740
aagcagaaga acggcatcaa ggccaacttc aagatccgcc acaacatcga ggacggcggc    1800
gtgcagctcg ccgaccacta ccagcagaac acccccatcg gcgacggccc cgtgctgctg    1860
cccgacaacc actacctgag ctaccagtcc gccctgagca aagaccccaa cgagaagcgc    1920
gatcacatgg tcctgctgga gttcgtgacc gccgccggga tcactctcgg catggacgag    1980
ctgtacaagt aa                                                        1992
```

<210> SEQ ID NO 32
<211> LENGTH: 1920
<212> TYPE: DNA
<213> ORGANISM: Artificial Sequence
<220> FEATURE:

<223> OTHER INFORMATION: Synthetic

<400> SEQUENCE: 32

```
atggtgagca agggcgagga gaccacaatg ggcgtaatca agcccgacat gaagatcaag     60
ctgaagatgg agggcaacgt gaatggccac gccttcgtga tcgagggcga gggcgagggc    120
aagccctacg acggcaccaa caccatcaac ctggaggtga aggagggagc ccccctgccc    180
ttctcctacg acattctgac caccgcgttc gcctacggca acagggcctt caccaagtac    240
cccgacgaca tccccaacta cttcaagcag tccttccccg agggctactc ttgggagcgc    300
accatgacct tcgaggacaa gggcatcgtg aaggtgaagt ccgacatctc catggaggag    360
gactccttca tctacgagat acacctcaag ggcgagaact tcccccccaa cggccccgtg    420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca acaaggtgac cgtttacgag    660
agcgccgtgg cccgcaactc caccgacggc atggacgagc tgtacaagag atctggtacc    720
ggccaggcgc tttccctctc cgtgacgctg cagttggtca ccaaccaggt cggccaccac    780
gatatttatg aaacccgcca actccttgaa ggctgggctg ccctgcattc cagcgccgaa    840
cgtggcgact gggacgtggc agaagcgttg ctggaaaaga tggacgaccc ctcgctaccg    900
ctcgaggatt ttttgcgttt cgacgccgaa ttccacgttg ttatctccaa aggcgcggaa    960
aaccctctga tcagtacgct catggaagcc ctccgtttgt ccgtggcaga tcacaccgtt   1020
gccagggccc gggcgctccc cgattggcga gccacctcgg cgcgtctgca gaaagaacac   1080
cgcgcaatcc tcgcagcact tcgcgcaggc gaatccacag tggccgcaac cttgatcaaa   1140
gaacacatcg aaggctacta cgaagaaacc gctgccgccg aggcccttaa gagatctacc   1200
atggtgagca agggcgagga gctgttcacc ggggtggtgc ccatcctggt cgagctggac   1260
ggcgacgtaa acggccacaa gttcagcgtg tccggcgagg gcgagggcga tgccacctac   1320
ggcaagctga ccctgaagct gatctgcacc accggcaagc tgcccgtgcc ctggcccacc   1380
ctcgtgacca ccctgggcta cggcctgcag tgcttcgccc gctaccccga ccacatgaag   1440
cagcacgact tcttcaagtc cgccatgccc gaaggctacg tccaggagcg caccatcttc   1500
ttcaaggacg acggcaacta caagacccgc gccgaggtga agttcgaggg cgacaccctg   1560
gtgaaccgca tcgagctgaa gggcatcgac ttcaaggagg acggcaacat cctggggcac   1620
aagctggagt acaactacaa cagccacaac gtctatatca ccgccgacaa gcagaagaac   1680
ggcatcaagg ccaacttcaa gatccgccac aacatcgagg acggcggcgt gcagctcgcc   1740
gaccactacc agcagaacac ccccatcggc gacggccccg tgctgctgcc cgacaaccac   1800
tacctgagct accagtccgc cctgagcaaa gaccccaacg agaagcgcga tcacatggtc   1860
ctgctggagt tcgtgaccgc cgccgggatc actctcggca tggacgagct gtacaagtaa   1920
```

<210> SEQ ID NO 33
<211> LENGTH: 258
<212> TYPE: PRT
<213> ORGANISM: Escherichia coli

<400> SEQUENCE: 33

```
Met Ile Val Leu Pro Arg Arg Leu Ser Asp Glu Val Ala Asp Arg Val
1               5                   10                  15
```

```
Arg Ala Leu Ile Asp Glu Lys Asn Leu Glu Ala Gly Met Lys Leu Pro
            20                  25                  30

Ala Glu Arg Gln Leu Ala Met Gln Leu Gly Val Ser Arg Asn Ser Leu
        35                  40                  45

Arg Glu Ala Leu Ala Lys Leu Val Ser Glu Gly Val Leu Leu Ser Arg
    50                  55                  60

Arg Gly Gly Gly Thr Phe Ile Arg Trp Arg His Asp Thr Trp Ser Glu
65                  70                  75                  80

Gln Asn Ile Val Gln Pro Leu Lys Thr Leu Met Ala Asp Asp Pro Asp
                85                  90                  95

Tyr Ser Phe Asp Ile Leu Glu Ala Arg Tyr Ala Ile Glu Ala Ser Thr
            100                 105                 110

Ala Trp His Ala Ala Met Arg Ala Thr Pro Gly Asp Lys Glu Lys Ile
        115                 120                 125

Gln Leu Cys Phe Glu Ala Thr Leu Ser Glu Asp Pro Asp Ile Ala Ser
    130                 135                 140

Gln Ala Asp Val Arg Phe His Leu Ala Ile Ala Glu Ala Ser His Asn
145                 150                 155                 160

Ile Val Leu Leu Gln Thr Met Arg Gly Phe Phe Asp Val Leu Gln Ser
                165                 170                 175

Ser Val Lys His Ser Arg Gln Arg Met Tyr Leu Val Pro Pro Val Phe
            180                 185                 190

Ser Gln Leu Thr Glu Gln His Gln Ala Val Ile Asp Ala Ile Phe Ala
        195                 200                 205

Gly Asp Ala Asp Gly Ala Arg Lys Ala Met Met Ala His Leu Ser Phe
    210                 215                 220

Val His Thr Thr Met Lys Arg Phe Asp Glu Asp Gln Ala Arg His Ala
225                 230                 235                 240

Arg Ile Thr Arg Leu Pro Gly Glu His Asn Glu His Ser Arg Glu Lys
                245                 250                 255

Asn Ala


<210> SEQ ID NO 34
<211> LENGTH: 231
<212> TYPE: PRT
<213> ORGANISM: Corynebacterium glutamicum

<400> SEQUENCE: 34

Met Ser Val Lys Ala His Glu Ser Val Met Asp Trp Val Thr Glu Glu
1               5                   10                  15

Leu Arg Ser Gly Arg Leu Lys Ile Gly Asp His Leu Pro Ser Glu Arg
            20                  25                  30

Ala Leu Ser Glu Thr Leu Gly Val Ser Arg Ser Ser Leu Arg Glu Ala
        35                  40                  45

Leu Arg Val Leu Glu Ala Leu Gly Thr Ile Ser Thr Ala Thr Gly Ser
    50                  55                  60

Gly Pro Arg Ser Gly Thr Ile Ile Thr Ala Ala Pro Gly Gln Ala Leu
65                  70                  75                  80

Ser Leu Ser Val Thr Leu Gln Leu Val Thr Asn Gln Val Gly His His
                85                  90                  95

Asp Ile Tyr Glu Thr Arg Gln Leu Leu Glu Gly Trp Ala Ala Leu His
            100                 105                 110

Ser Ser Ala Glu Arg Gly Asp Trp Asp Val Ala Glu Ala Leu Leu Glu
        115                 120                 125
```

-continued

```
Lys Met Asp Asp Pro Ser Leu Pro Leu Glu Asp Phe Leu Arg Phe Asp
    130                 135                 140

Ala Glu Phe His Val Val Ile Ser Lys Gly Ala Glu Asn Pro Leu Ile
145                 150                 155                 160

Ser Thr Leu Met Glu Ala Leu Arg Leu Ser Val Ala Asp His Thr Val
                165                 170                 175

Ala Arg Ala Arg Ala Leu Pro Asp Trp Arg Ala Thr Ser Ala Arg Leu
            180                 185                 190

Gln Lys Glu His Arg Ala Ile Leu Ala Ala Leu Arg Ala Gly Glu Ser
        195                 200                 205

Thr Val Ala Ala Thr Leu Ile Lys Glu His Ile Glu Gly Tyr Tyr Glu
    210                 215                 220

Glu Thr Ala Ala Ala Glu Ala
225                 230
```